US009034814B2

(12) United States Patent
Peled et al.

(10) Patent No.: US 9,034,814 B2
(45) Date of Patent: May 19, 2015

(54) CXCR4 ANTAGONISTS FOR WOUND HEALING AND RE-EPITHELIALIZATION

(75) Inventors: Amnon Peled, Tel Aviv (IL); Nobutaka Fujii, Shiga (JP)

(73) Assignees: Hadasit Medical Research Services and Development Ltd., Jerusalem (IL); Kyoto University, Kyoto (JP)

( * ) Notice: Subject to any disclaimer, the term of this patent is extended or adjusted under 35 U.S.C. 154(b) by 1896 days.

(21) Appl. No.: 11/915,428

(22) PCT Filed: May 21, 2006

(86) PCT No.: PCT/IL2006/000596
§ 371 (c)(1),
(2), (4) Date: Nov. 6, 2009

(87) PCT Pub. No.: WO2006/126188
PCT Pub. Date: Nov. 30, 2006

(65) Prior Publication Data
US 2010/0055088 A1     Mar. 4, 2010

Related U.S. Application Data

(60) Provisional application No. 60/684,160, filed on May 25, 2005.

(51) Int. Cl.
*A61K 38/10* (2006.01)
*A61K 38/04* (2006.01)
*C07K 16/28* (2006.01)

(52) U.S. Cl.
CPC .................. *A61K 38/04* (2013.01); *A61K 38/10* (2013.01); *C07K 16/2866* (2013.01); *C07K 2316/96* (2013.01)

(58) Field of Classification Search
None
See application file for complete search history.

(56) References Cited

U.S. PATENT DOCUMENTS

| 4,760,051 | A | * | 7/1988 | Pickart | 514/9.4 |
| 6,491,906 | B1 | | 12/2002 | Strieter et al. | |
| 7,138,488 | B2 | | 11/2006 | Fujii | |
| 7,423,007 | B2 | * | 9/2008 | Fujii et al. | 512/14 |
| 8,017,585 | B2 | * | 9/2011 | Fujii et al. | 514/21.5 |
| 2001/0006640 | A1 | | 7/2001 | Grainger | |
| 2002/0004489 | A1 | * | 1/2002 | Shi et al. | 514/44 |
| 2004/0209921 | A1 | | 10/2004 | Bridger | |
| 2009/0181897 | A1 | | 7/2009 | Fujii | |

FOREIGN PATENT DOCUMENTS

| EP | 1323730 A1 | 7/2003 | |
| WO | 99/47158 A2 | 9/1999 | |
| WO | WO 0222599 A2 * | 3/2002 | C07D 401/12 |
| WO | WO 2004020462 A1 * | 3/2004 | C07K 7/08 |
| WO | 2004/087068 A2 | 10/2004 | |

OTHER PUBLICATIONS

Davis et al., "A Comparison of Biomechanical Properties of Excised Mature Scars from HIV Patients and Non-HIV Controls", The American Journal of Surgery, 2000, pp. 217-222.*
Gillitzer et al., "Chemokines in cutaneous wound healing", Journal of Leukocyte Biology, 2001, pp. 513-521.*
Avniel et al., "Involvement of the CXCL12/CXCR4 Pathway in the Recovery of Skin Following Burns", Journal of Investigative Dermatology, 2006, pp. 468-476.*
Zeelenberg et al., "The Role of Chemokine Receptors, in Particular CXCR4, in Lymphoma and Carcinoma Metastasis", 2005, Integration/Interaction of Oncologic Growth, p. 233-244.*
WO2004/020462 A1, translation,pp. 1-69, translation obtained att http://worldwide.espacenet.com on Jul. 2014.*
Tamamura, H., Synthesis of potent CXCR4 inhibitors possessing low cytotoxicity and improved biostability based on T140 derivatives, Org. Biomol. Chem. 2003, vol. 1, pp. 3656-3662.
Tamamura, H., Enhancement of the T140-based pharmacophores leads to the development of more potent bio-stable CXCR4 antagonists, Org. Biomol. Chem. 2003, vol. 1, pp. 3663-3669.
Tamamura, H., T140 analogs as CXCR4 antagonists identified as anti-metastatic agents in the treatment of breast cancer, FEBS Letter 2003, vol. 550, pp. 79-83.
A. Aiuti et al., (1997) The chemokine SDF-1 is a chemoattractant for human CD34+ hematopoietic progenitor cells and provides a new mechanism to explain the mobilization of CD34+ progenitors to peripheral blood. J. Exp. Med. 185(1):111-20.
A. Askari et al., (2003) Effect of stromal-cell-derived factor 1 on stem-cell homing and tissue regeneration in ischaemic cardiomyopathy. Lancet 362:697-703.
S. Avniel et al., (2006) Involvement of the CXCL12/CXCR4 pathway in the recovery of skin following burns. J Invest Dermatol 126:468-76.
C. Hitchon et al., (2002) Hypoxia-induced production of stromal cell-derived factor 1 (CXCL12) and vascular endothelial growth factor by synovial fibroblasts. Arthritis Rheum. 46: 2587-97.
N. Lack et al., (2005) A pharmacokinetic-pharmacodynamic model for the mobilization of CD34+ hematopoietic progenitor cells by AMD3100. Clin. Pharmacol. Ther. 77(5):427-36.
T. Nagasawa et al., (1996) Defects of B-cell lymphopoiesis and bone-marrow myelopoiesis in mice lacking the CXC chemokine PBSF/SDF-1. Nature 382:635-38.
J. Pablos et al., (1999) Stromal-cell derived factor is expressed by dendritic cells and endothelium in human skin. Am. J. Pathol. 155(5): 1577-86.
A. Peled et al., (1999) Dependence of human stem cell engraftment and repopulation of NOD/SCID mice on CXCR4. Science 283:845-8.

(Continued)

*Primary Examiner* — Karlheinz R Skowronek
*Assistant Examiner* — Lianko Garyu
(74) *Attorney, Agent, or Firm* — Rothwell, Figg, Ernst & Manbeck, P.C.

(57) ABSTRACT

The present invention provides novel uses for CXCR4 antagonists, including specifically peptides of the T-140 family, in the treatment of skin burns and other injuries. The invention further provides methods for increasing epithelialization in a subject in need thereof, and for preventing or inhibiting fibrosis and excessive scar formation, using peptide inhibitors of the T-140 family as well as other CXCR4 antagonists.

18 Claims, 11 Drawing Sheets

(56) References Cited

OTHER PUBLICATIONS

R. Phillips et al., (2004) Circulating fibrocytes traffic to the lungs in response to CXCL12 and mediate fibrosis. J Clin Invest 114(3):438-46.

T. Ponomaryov et al., (2000) Induction of the chemokine stromal-derived factor-1 following DNA damage improves human stem cell function. J. Clin. Invest. 106(11):1331-9.

T. Schioppa et al., (2003) Regulation of the chemokine receptor CXCR4 by hypoxia. J. Exp. Med. 198(9):1391-402.

J. Smith et al., (2005) CXCL12 activation of CXCR4 regulates mucosal host defense through stimulation of epithelial cell migration and promotion of intestinal barrier integrity. Am J Physiol Gastrointest Liver Physiol 288:G316-26.

P. Staller et al., (2003) Chemokine receptor CXCR4 downregulated by von Hippel-Lindau tumour suppressor pVHL. Nature 425:307-11.

J. Strizki et al., (1997) A monoclonal antibody (12G5) directed against CXCR-4 inhibits infection with the dual-tropic human immunodeficiency virus type 1 isolate HIV-1(89.6) but not the T-tropic isolate HIV-1(HxB). J Virol 71(7):5678-83.

H. Tamamura et al., (1998) A low-molecular-weight inhibitor against the chemokine receptor CXCR4: a strong anti-HIV peptide T140. Biochemical and Biophysical Research Commun. 253:877-82.

L. Wei et al., (2007) Effects of anti-CXCR4 monoclonal antibody 12G5 on proliferation and apoptosis of human acute myelocytic leukemia cell line HL-60. Journal of Medical Colleges of PLA, Shanghai, CN 22(1):17-22.

Y. Zou et al., (1998) Function of the chemokine receptor CXCR4 in haematopoiesis and in cerebellar development. Nature 393:595-9.

Ceradini, Daniel J. et al., (2004) Progenitor cell trafficking is regulated by hypoxic gradients through HIF-1 induction of SDF-1. Nat Med 10(8):858-864.

* cited by examiner

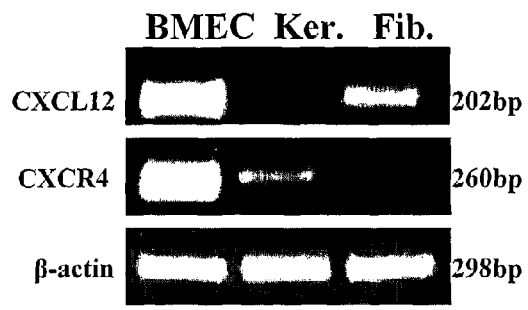
Figure 7A
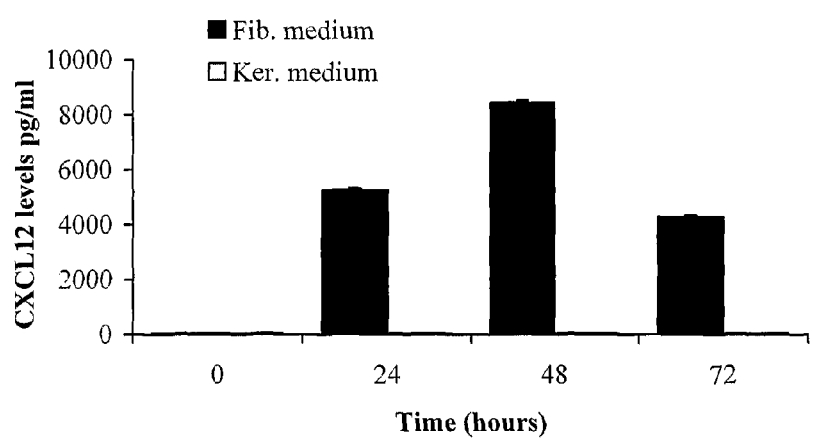
Figure 7B
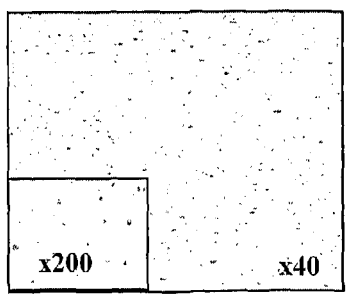 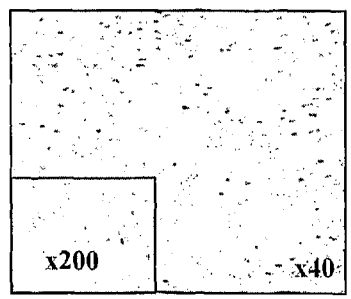 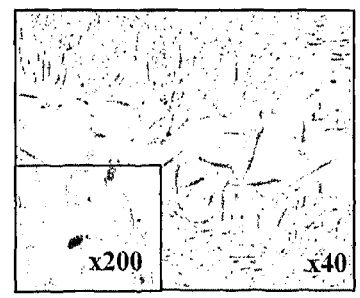
Figure 7C          Figure 7D          Figure 7E

CXCR4 ANTAGONISTS FOR WOUND HEALING AND RE-EPITHELIALIZATION

This application is a National Phase of International Application No. PCT/IL2006/000596, filed 21 May 2006 and further claims the benefit of U.S. Provisional Application No. 60/684,160, filed May 25, 2005.

FIELD OF THE INVENTION

The present invention relates to the use of CXCR4 antagonists for the treatment of skin lesions including burn injuries and for promoting wound healing and re-epithelialization.

BACKGROUND OF THE INVENTION

Skin integrity is of importance for the protection and separation of body tissues from the surrounding environment. The loss of skin due to burns or trauma exposes the body to severe stress, impairing or even eliminating the many vital functions this organ performs. The skin contains two main layers of cells: a thin outer layer, the epidermis, and a thicker inner layer, the dermis. Full thickness skin tissue is comprised of keratinocytes lined on a basement membrane, produced by fibroblasts. Deeper layers of the skin include, in addition to fibroblasts, fat cells and multiple subsets of immune cells such as dendritic cells, lymphocytes and polymorphonuclear cells. The complex organization of normal skin is designed to support the numerous functions of this organ as both an immunologic and a physical barrier. Nevertheless, not much is known about the factors responsible for the complex architecture of this organ under physiologic and pathologic conditions.

Chemokines and Chemokine Inhibitors

Cytokines are, generally, small protein or polypeptide-based molecules that modulate the activity of certain cell types following binding to cell surface receptors. Chemokines are a subgroup of cytokines that mediate a range of proinflammatory effects on leukocytes, such as chemotaxis, degranulation, and integrin activation. The CXC chemokines are a group of chemokines so named due to the conserved Cys-Xaa-Cys sequence element located towards their N-terminus. Among this group of chemokines is stromal-derived factor-1 (SDF-1, also known as CXCL12).

CXCL12 controls many aspects of stem cell function. CXCL12 has been identified as a powerful chemoattractant for immature hematopoietic stem cells (Aiuti et al., 1997). Mice that lack either CXCL12 or its receptor CXCR4 exhibit many defects, including impaired hematopoiesis in the fetal bone marrow (Nagasawa et al., 1996; Zou et al., 1998). Recently, it was shown that mobilization, homing and engraftment of hematopoietic stem cells as well as the trafficking of neuronal and primordial germ cells is dependent on the expression of CXCL12 and CXCR4 (Peled et al., 1999). It was also shown that the expression of CXCL12 is upregulated following irradiation and hypoxia and that CXCL12 can induce the recruitment of endothelial progenitor cells in a regeneration model for myocardial infarction (Askari et al., 2003; Ceradini et al., 2004; Ponomaryov et al., 2000). The regulation of CXCL12 and its physiological role in peripheral tissue repair remain incompletely understood. A recent study showed that CXCL12 gene expression is regulated by the transcription factor hypoxia-inducible factor-1 (HIF-1) in endothelial cells, resulting in the selective in vivo expression of CXCL12 in ischemic tissue in direct proportion to reduced oxygen tension (Hitchon et al., 2002; Schioppa et al., 2003). HIF-1-induced CXCL12 expression increases the adhesion, migration and homing of circulating CXCR4-positive progenitor cells to ischemic tissue. Other studies have shown that the von Hippel-Lindau tumor suppressor protein, pVHL, negatively regulates CXCR4 expression owing to its capacity to target HIF for degradation under normoxic conditions (Staller et al., 2003).

Thus, CXCL12 plays an important role in the organization of tissues during development and following irradiation and hypoxia. CXCL12 is expressed by dendritic cells, fibroblasts and endothelial cells in human skin (Pablos et al., 1999).

Various chemokine receptor inhibitors, including CXCR4 inhibitors, have been described in the art. For example, a bicyclam drug termed AMD3100, originally discovered as an anti-HIV compound and which specifically interacts with CXCR4, is currently undergoing clinical trials to evaluate its ability to increase stem cells available for transplant (Lack et al., 2005).

The involvement of chemokines in various aspects of leukocyte activity has prompted different speculations regarding the possibility of regulating wound healing by modulating chemokine activity. For instance, U.S. Patent Application Publication No. 2001/0006640 discloses peptides derived from various chemokines, which peptides are homologous to residues 46-67 or 27-45 of mature human MCP-1 and may act as antagonists or agonists of chemokine activity, and uses thereof for immunomodulation. Certain particular peptides derived from CXCL12 were disclosed in the specification. The '640 application further suggests that peptide chemokine inhibitors derived from chemokines such as MCP-1 and IL-8 may inhibit recruitment of neutrophil or macrophage accumulation at the site of the wound, and thereby enhance wound healing.

U.S. Patent Application Publication No. 2004/0209921 discloses heterocyclic compounds that bind to chemokine receptors, including CXCR4 and CCR5, which may possess protective effects against infection of target cells by a human immunodeficiency virus (HIV). Other potential uses for these compounds suggested by '921 are enhancing the population of progenitor and/or stem cells, stimulating the production of white blood cells, and/or effecting regeneration of cardiac tissue. The '921 application speculates that elevated white blood cell counts may be beneficial for wound healing.

T-140 Analogs

T-140 is a 14-residue synthetic peptide developed by some of the inventors of the present invention as a specific CXCR4 antagonist which suppress T-cell line-tropic HIV-1 (X4-HIV-1) entry through specific binding to CXCR4 (Tamamura et al., 1998). Subsequently, peptide analogs of T-140 were developed by some of the inventors of the present invention as specific CXCR4 antagonist peptides with inhibitory activity at nanomolar levels (see Tamamura et al., 2003, WO 2002/020561 and WO 2004/020462).

WO 2002/020561 discloses novel peptide analogs and derivatives of T-140. The '561 publication demonstrates that the claimed peptides are potent CXCR4 inhibitors, manifesting high anti-HIV virus activity and low cytotoxicity.

WO 2004/020462 discloses additional novel peptide analogs and derivatives of T-140. The '462 publication further discloses novel preventive and therapeutic compositions and methods of using same utilizing T-140 analogs for the treatment of cancer and chronic rheumatoid arthritis. The specification of '462 demonstrates the ability of these peptides to inhibit cancer cell migration, including breast cancer and leukemia cells, and to inhibit mastasis formation in vivo. Further demonstrated therein is inhibition of delayed-type hypersensitivity reaction in mice and collagen-induced arthritis, an animal model of rheumatoid arthritis.

None of the background art discloses or demonstrates that CXCR4 antagonists, particularly T-140 analogs, may be effectively used for the treatment of skin burns and for promoting wound healing while inhibiting fibrosis. There exists a need for improved treatments of skin lesions effective to promote the healing process of wounds and skin burns, and to prevent scar formation and other diseases associated with fibrosis.

SUMMARY OF THE INVENTION

The present invention provides compositions and methods using CXCR4 antagonists for promoting wound healing, for the treatment of skin burns, and for preventing scar formation, promoting epithelialization and inhibiting fibrosis. Particularly, the invention provides methods of treating wounds and skin lesions, including skin burns, and other conditions associated with excessive fibrosis and scar formation, using peptide inhibitors of the T-140 family as well as other CXCR4 antagonists.

The invention is based, in part, on the unexpected discovery that following burns, the level of CXCL12 was markedly increased first in the burn blister and then in the junction tissues surrounding the burn, hair follicles, blood vessel endothelium, and fibroblasts in the recovering dermis. CXCL12 levels have also been surprisingly found to be upregulated in fibroblasts following trauma or wound formation.

The present invention discloses for the first time the surprising discovery that treatment of partial thickness burns in a rat model with a small peptide CXCR4 antagonist of the T-140 family, namely 4F-benzoyl-TN14003 (SEQ ID NO:52), or with an anti-CXCR4 monoclonal antibody (mAb), resulted in improved epithelialization and reduced eosinophilia. As exemplified herein, the peptide antagonist was more potent than the neutralizing mAb in improving wound healing in vivo.

According to a first aspect, the present invention provides methods of treating wounds and promoting wound healing in a subject in need thereof, comprising administering to the subject a pharmaceutical composition comprising a therapeutically effective amount of a CXCR4 inhibitor.

In various embodiments, the CXCR4 inhibitor includes, but is not limited to, polypeptides, peptides, antibodies and fragments thereof, and small organic molecules. In certain particular embodiments, the inhibitor is an antibody or an antibody fragment having CXCR4 inhibitory activity, e.g. single-chain antibodies (scFvs) and single antibody domain proteins (dAbs). In a particular embodiment, said inhibitor is mAb 12G5 or an active fragment thereof having CXCR4 inhibitory activity.

According to certain embodiments, CXCR4 inhibitors particularly useful for practicing the methods of the present invention are analogs and derivatives of T-140, a known peptide having the amino acid sequence H-Arg-Arg-Nal-Cys-Tyr-Arg-Lys-DLys-Pro-Tyr-Arg-Cit-Cys-Arg-OH (SEQ ID NO:69, Tamamura et al., 1998). The preferable peptides of the invention include analogs and derivatives disclosed in patent applications WO 2002/020561 and WO 2004/020462, as detailed hereinbelow.

In one embodiment, the CXCR4 inhibitor is a peptide having the following formula (I) or a salt thereof:

$$\underset{A_1-A_2-A_3-Cys-Tyr-A_4-A_5-A_6-A_7-A_8-A_9-A_{10}-Cys-A_{11}}{1\ \ 2\ \ 3\ \ 4\ \ 5\ \ 6\ \ 7\ \ 8\ \ 9\ \ 10\ 11\ 12\ 13\ 14} \quad (I)$$

wherein:
$A_1$ is an arginine, lysine, ornithine, citrulline, alanine or glutamic acid residue or a N-α-substituted derivative of these amino acids, or $A_1$ is deleted;
$A_2$ represents an arginine or glutamic acid residue if $A_1$ is present, or $A_2$ represents an arginine or glutamic acid residue or a N-α-substituted derivative of these amino acids if $A_1$ is deleted;
$A_3$ represents an aromatic amino acid residue;
$A_4$, $A_5$ and $A_9$ each independently represents an arginine, lysine, ornithine, citrulline, alanine or glutamic acid residue;
$A_6$ represents a proline, glycine, ornithine, lysine, alanine, citrulline, arginine or glutamic acid residue;
$A_7$ represents a proline, glycine, ornithine, lysine, alanine, citrulline or arginine residue;
$A_8$ represents a tyrosine, phenylalanine, alanine, naphthylalanine, citrulline or glutamic acid residue;
$A_{10}$ represents a citrulline, glutamic acid, arginine or lysine residue;
$A_{11}$ represents an arginine, glutamic acid, lysine or citrulline residue wherein the C-terminal carboxyl may be derivatized;
and the cysteine residue of the 4-position or the 13-position can form a disulfide bond, and the amino acids can be of either L or D form (SEQ ID NO: 80).

In another embodiment, the composition comprises a peptide having an amino acid sequence as set forth in formula (I) as defined hereinabove, wherein:
$A_1$ is an arginine, citrulline, alanine or glutamic acid residue or a N-α-substituted derivative of these amino acids, or $A_1$ is deleted;
$A_2$ represents an arginine or glutamic acid residue if $A_1$ is an arginine, citrulline, alanine or glutamic acid residue or a N-α-substituted derivative of these amino acids, or $A_2$ represents an arginine or glutamic acid residue or a N-α-substituted derivative of these amino acids if A1 is deleted;
$A_4$ represents an arginine, citrulline, alanine or glutamic acid residue;
$A_5$ represents an arginine, lysine, citrulline, alanine or glutamic acid residue;
$A_6$ represents a lysine, alanine, citrulline or glutamic acid residue;
$A_7$ represents a proline or alanine residue;
$A_8$ represents a tyrosine, alanine or glutamic acid residue;
$A_9$ represents an arginine, citrulline or glutamic acid residue;
$A_{10}$ represents a citrulline or glutamic acid residue;
$A_{11}$ represents an arginine or glutamic acid residue wherein the C-terminal carboxyl may be derivatized.

In another embodiment, the composition comprises a peptide having an amino acid sequence as set forth in formula (I) as defined hereinabove, wherein $A_1$ is a glutamic acid residue or is deleted.

In another embodiment, the composition comprises a peptide having an amino acid sequence as set forth in formula (I) as defined hereinabove, wherein $A_2$ is a glutamic acid residue.

In another embodiment, the composition comprises a peptide having an amino acid sequence as set forth in formula (I) as defined hereinabove, wherein $A_4$ is a glutamic acid residue.

In another embodiment, the composition comprises a peptide having an amino acid sequence as set forth in formula (I) as defined hereinabove, wherein $A_6$ is a glutamic acid residue.

In another embodiment, the composition comprises a peptide having an amino acid sequence as set forth in formula (I) as defined hereinabove, wherein $A_8$ is a glutamic acid residue.

In another embodiment, the composition comprises a peptide having an amino acid sequence as set forth in formula (I) as defined hereinabove, wherein $A_9$ is a glutamic acid residue.

In another embodiment, the composition comprises a peptide having an amino acid sequence as set forth in formula (I) as defined hereinabove, wherein $A_5$ is an arginine or glutamic acid residue.

In another embodiment, the composition comprises a peptide having an amino acid sequence as set forth in formula (I) as defined hereinabove, wherein $A_{10}$ is a glutamic acid, arginine or lysine residue.

In another embodiment, the composition comprises a peptide having an amino acid sequence as set forth in formula (I), wherein: $A_1$ is an arginine, alanine or citrulline residue; $A_2$ is an arginine residue; $A_3$ is a tryptophan or naphthylalanine residue; $A_4$ is an arginine, alanine or citrulline residue; $A_5$ is a lysine, alanine or citrulline residue; $A_6$ and $A_7$ collectively represent a dipeptide selected from the group consisting of: D-lysyl-proline, D-alanyl-proline, D-lysyl-alanine and D-citrullyl-proline; $A_8$ is a tyrosine or alanine residue; $A_9$ is an arginine, alanine or citrulline residue; $A_{10}$ is a citrulline residue; and $A_{11}$ is an arginine residue.

Exemplary peptides according to formula (I) are peptides having an amino acid sequence as set forth in any one of SEQ ID NOS:1-71, as presented in Table 1 hereinbelow.

In a preferable embodiment, the peptide has an amino acid sequence as set forth in SEQ ID NO:65 (H-Arg-Arg-Nal-Cys-Tyr-Cit-Lys-DLys-Pro-Tyr-Arg-Cit-Cys-Arg-OH; TC14003) or is an analog or a derivative thereof.

In certain particular embodiments, said peptide has an amino acid sequence as set forth in any one of:

```
                                          (SEQ ID NO: 1)
Ac-Arg-Arg-Nal-Cys-Tyr-Cit-Lys-DLys-Pro-Tyr-Arg-
Cit-Cys-Arg-OH, (SEQ ID NO: 2)
Ac-Arg-Arg-Nal-Cys-Tyr-Arg-Lys-DCit-Pro-Tyr-Arg-
Cit-Cys-Arg-OH, (SEQ ID NO: 3)
Ac-Arg-Arg-Nal-Cys-Tyr-Cit-Lys-DCit-Pro-Tyr-Arg-
Cit-Cys-Arg-OH, (SEQ ID NO: 9)
Ac-Arg-Arg-Nal-Cys-Tyr-Cit-Lys-DCit-Pro-Tyr-Arg-
Cit-Cys-Arg-NH2, (SEQ ID NO: 45)
TMguanyl-Arg-Arg-Nal-Cys-Tyr-Cit-Lys-DCit-Pro-Tyr-
Arg-Cit-Cys-Arg-NH2;, (SEQ ID NO: 46)
ACA-Arg-Arg-Nal-Cys-Tyr-Cit-Lys-DCit-Pro-Tyr-Arg-
Cit-Cys-Arg-NH2, (SEQ ID NO: 50)
Ac-Arg-Arg-Nal-Cys-Tyr-Cit-Lys-DLys-Pro-Tyr-Arg-
Cit-Cys-Arg-NH2, (SEQ ID NO: 51)
Ac-Arg-Arg-Nal-Cys-Tyr-Arg-Lys-DCit-Pro-Tyr-Arg-
Cit-Cys-Arg-NH2, (SEQ ID NO: 52)
4F-benzoyl-Arg-Arg-Nal-Cys-Tyr-Cit-Lys-DLys-Pro-
Tyr-Arg-Cit-Cys-Arg-NH2, (SEQ ID NO: 53)
4F-benzoyl-Arg-Arg-Nal-Cys-Tyr-Cit-Lys-DGlu-Pro-
Tyr-Arg-Cit-Cys-Arg-NHMe, (SEQ ID NO: 54)
4F-benzoyl-Arg-Arg-Nal-Cys-Tyr-Cit-Lys-DGlu-Pro-
Tyr-Arg-Cit-Cys-Arg-NHEt, (SEQ ID NO: 55)
4F-benzoyl-Arg-Arg-Nal-Cys-Tyr-Cit-Lys-DGlu-Pro-
Tyr-Arg-Cit-Cys-Arg-NHiPr, (SEQ ID NO: 56)
4F-benzoyl-Arg-Arg-Nal-Cys-Tyr-Cit-Lys-DGlu-Pro-
Tyr-Arg-Cit-Cys-Arg-tyramine, (SEQ ID NO: 65)
H-Arg-Arg-Nal-Cys-Tyr-Cit-Lys-DLys-Pro-Tyr-Arg-
Cit-Cys-Arg-OH, (SEQ ID NO: 66)
H-Arg-Arg-Nal-Cys-Tyr-Cit-Lys-DLys-Pro-Tyr-Arg-
Cit-Cys-Arg-NH2

(SEQ ID NO: 68)
H-Arg-Arg-Nal-Cys-Tyr-Cit-Lys-DCit-Pro-Tyr-Arg-
Cit-Cys-Arg-NH2, (SEQ ID NO: 70)
H-Arg-Arg-Nal-Cys-Tyr-Cit-Lys-DCit-Pro-Tyr-Arg-
Cit-Cys-Arg-OH,
and
                                         (SEQ ID NO: 71)
H-Arg-Arg-Nal-Cys-Tyr-Arg-Lys-DCit-Pro-Tyr-Arg-
Cit-Cys-Arg-OH.
```

In other particular embodiments, said peptide has an amino acid sequence as set forth in any one of SEQ ID NOS:3, 9, 45, 46, 68 and 70. In further particular embodiments, said peptide has an amino acid sequence as set forth in any one of SEQ ID NOS:1, 50, 52, 65 and 66. In other particular embodiments, said peptide has an amino acid sequence as set forth in any one of SEQ ID NOS:53-56.

In another preferable particular embodiment, the peptide has an amino acid sequence as set forth in SEQ ID NO:52.

In another embodiment, the composition comprises a peptide having an amino acid sequence as set forth in the following formula (II) or a salt thereof:

$$\begin{array}{cccccccccccccc}
& 1 & 2 & 3 & 4 & 5 & 6 & 7 & 8 & 9 & 10 & 11 & 12 & 13 \\
& A_1\text{-Arg-}A_2\text{-Cys-Tyr-}A_3\text{-}A_4\text{-X-}A_5\text{-}A_6\text{-Cit-Cys-}A_7 & & & & & & & & & & & &
\end{array} \quad (II)$$

wherein:
$A_1$ represents a hydrogen atom, or an arginine, lysine, ornithine, citrulline or alanine residue or a residue of N-α-substituted derivative of these amino acids;
$A_2$ represents an aromatic amino acid residue;
$A_3$, $A_4$ and $A_6$ each independently represent an arginine, lysine, ornithine, citrulline or alanine residue;
$A_5$ represents a tyrosine, phenylalanine, alanine, naphthylalanine or citrulline residue;
$A_7$ represents a lysine or arginine residue in which a carboxyl group may be amidated or esterified;
X is selected from the group consisting of:
(i) a peptide represented by the following formula (III):

$$\begin{array}{cccccc}
1' & 2' & 3' & 4' & 5' & 6' \\
-A_8\text{-}A_9\text{-}A_{10}\text{-Gly-}A_{11}\text{-}A_{12}\text{-} & & & & &
\end{array} \quad (III)$$

wherein $A_8$ and $A_{12}$ each independently represents an alanine, valine, leucine, isoleucine, serine, cysteine or methionine residue;
$A_9$ represents an aromatic amino acid residue, $A_{10}$ is selected from the same amino acid residues as in $A_3$, $A_{11}$ represents a tyrosine, phenylalanine, tryptophan, alanine, valine, leucine, isoleucine, serine, cysteine or methionine residue, provided that when both $A_8$ and $A_{12}$ are cysteine residues, they may form a disulfide bond, and the cysteine residues at the 4-position and the 17-position may form a disulfide bond (SEQ ID NO: 94);

provided that, in the above peptide or a salt thereof, at least one of the amino acid residues of A1, A3, A4, A5, A6 and A7 is an alanine or citrulline residue;

(ii) a peptide selected from the group consisting of a D-ornithyl-proline, prolyl-D-ornithine, D-lysyl-proline, prolyl-D-lysine, D-arginyl-proline, prolyl-D-arginine, D-citrullyl-proline, D-citrullyl-alanine, D-alanyl-citrulline, prolyl-D-citrulline, glycyl-ornithine, ornithyl-glycine, glycyl-lysine, lysyl-glycine, glycyl-arginine, arginyl-glycine, glycyl-citrulline, citrullyl-glycine, D-alanyl-proline, and D-lysyl-alanine, wherein a hydrogen atom of a side chain w-amino group of D-arginine, L-arginine, D-lysine, L-lysine, D-ornithine or L-ornithine which are constitutional amino acids of said peptide residues may be substituted by a ω-aminoacyl group, and the cysteine residues at the 4-position and the 12-position may form a disulfide bond (SEQ ID NO: 93);

provided that, in the above peptide or a salt thereof, at least one of the amino acid residues of $A_1$, $A_3$, $A_4$, $A_5$, $A_6$ and $A_7$ is an alanine or citrulline residue; and (iii) a single amino acid residue selected from the group consisting of D-citrulline, D-alanine, citrulline and alanine (SEQ ID NO: 92).

In formula II as defined herein, the amino acid of $A_7$ is preferably one in which the carboxyl group is amidated or esterified, for improving in vivo stability of the polypeptide.

The terms "the T-140 analog peptides" or "T-140 analogs" as used herein refer to any peptide analog or derivative of T-140 retaining its active properties with respect to wound treatment as described herein. According to certain currently preferred embodiments, these terms refer to the peptides indicated by formulas (I) and (II), as presented herein.

In another embodiment, the wound is a dermal wound. In another embodiment, said wound is a partial thickness dermal wound.

In other aspects, the present invention provides methods of treating skin burns in a subject in need thereof, comprising administering to the subject a pharmaceutical composition comprising a therapeutically effective amount of a CXCR4 inhibitor.

In various embodiments, the CXCR4 inhibitor includes, but is not limited to, polypeptides, peptides, antibodies and fragments thereof, and small organic molecules. In certain particular embodiments, the inhibitor is an antibody or an antibody fragment having CXCR4 inhibitory activity.

In a preferable embodiment, the inhibitor is a T-140 analog peptide of the invention or a salt thereof.

In other aspects, the present invention provides methods for the prevention or reduction of scarring in a subject in need thereof, comprising administering to the subject a pharmaceutical composition comprising a therapeutically effective amount of a CXCR4 inhibitor.

In various embodiments, the CXCR4 inhibitor includes, but is not limited to, polypeptides, peptides, antibodies and fragments thereof, and small organic molecules. In certain particular embodiments, the inhibitor is an antibody or an antibody fragment having CXCR4 inhibitory activity.

In a preferable embodiment, the inhibitor is a T-140 analog peptide of the invention or a salt thereof.

In one embodiment, the method is useful for preventing or reducing scarring of the skin. In other embodiments, the present invention can also be used therapeutically to control diseases associated with excessive scarring, including, but not limited to cirrhosis of the liver, constrictive pericarditis, Dupuytren's disease of the hand, plantar fibrosis of the foot and various other fibromatoses.

According to further aspects, the invention provides methods of promoting epithelialization in a subject in need thereof, comprising administering to the subject a pharmaceutical composition comprising a therapeutically effective amount of a CXCR4 inhibitor.

In various embodiments, the CXCR4 inhibitor includes, but is not limited to, polypeptides, peptides, antibodies and fragments thereof, and small organic molecules. In certain particular embodiments, the inhibitor is an antibody or an antibody fragment having CXCR4 inhibitory activity.

In a preferable embodiment, the inhibitor is a T-140 analog peptide of the invention or a salt thereof.

According to other aspects, the invention provides methods of inhibiting or preventing fibrosis in a subject in need thereof, comprising administering to the subject a pharmaceutical composition comprising a therapeutically effective amount of a CXCR4 inhibitor.

In various embodiments, the CXCR4 inhibitor includes, but is not limited to, polypeptides, peptides, antibodies and fragments thereof, and small organic molecules. In certain particular embodiments, the inhibitor is an antibody or an antibody fragment having CXCR4 inhibitory activity.

In a preferable embodiment, the inhibitor is a T-140 analog peptide of the invention or a salt thereof.

In certain embodiments, the fibrosis includes, but is not limited to, fibrosis in the skin, in the lung, in the liver, in the kidney, of the central nervous system, in bone or bone marrow, in the cardiovascular system, in an endocrine organ or in the gastro-intestinal system. In a particular embodiment, the method is useful for treating skin fibrosis.

In other embodiments, the compositions of the invention may be administered by various local and systemic administration routes, depending on the particular condition or disease to be treated. In certain particular embodiments, said compositions are administered topically, intralesionally, transdermally, subcutaneously, intravenously, intrarectally or orally.

In another aspect, the invention provides topical pharmaceutical compositions comprising as an active ingredient a therapeutically effective amount of a CXCR4 inhibitor and a pharmaceutically acceptable carrier, excipient or diluent.

In various embodiments, the CXCR4 inhibitor includes, but is not limited to, polypeptides, peptides, antibodies and active fragments thereof, and small organic molecules. In certain particular embodiments, the inhibitor is an antibody or an antibody fragment having CXCR4 inhibitory activity.

In a preferable embodiment, the inhibitor is a T-140 analog peptide of the invention or a salt thereof.

In various embodiments, the topical pharmaceutical compositions may be formulated, for example, as non-washable (water-in-oil) creams or washable (oil-in-water) creams, ointments, lotions, gels, suspensions, aqueous or cosolvent solutions, salves, emulsions, wound dressings, coated bandages or other polymer coverings, sprays, aerosols, or liposomes.

A-F: Immunohistochemistry staining results using monoclonal antibody against the chemokine CXCL12 on rat normal skin sections. A—Cells stained in the basal layer of the epidermis. B—Scattered cells stained in the papillary dermis. C—Endothelial cells and pericytes stained in blood vessel. D—Axons and blood vessels stained in nerve tissue. E—Fibrous sheet stained in the hair follicle. F—Epidermis and papillary dermis control staining, without the primary antibody. (Original magnification ×400).

G-L: Immunohistochemistry staining results using monoclonal antibody against the chemokine CXCL12 on swine normal skin sections. G—Cells stained in the basal layer of the epidermis and the papillary dermis. H—Scattered cells stained in the papillary dermis. I—Endothelial cells and pericytes stained in blood vessel. J—Fibrous sheet stained in the hair follicle. K—Sweat glands staining. L—control staining, without the primary antibody. (Original magnification ×200, ×400).

FIG. 4: IL-8 (A) and CXCL12 (B) mean levels (pg/ml) in human burn wound fluid collected from blisters of patients with second-degree burns. Fluids were collected 0-5 days after burn as a medical treatment protocol. Samples were measured for the chemokines by ELISA assays. Each point represents one patient.

Figure 5A:
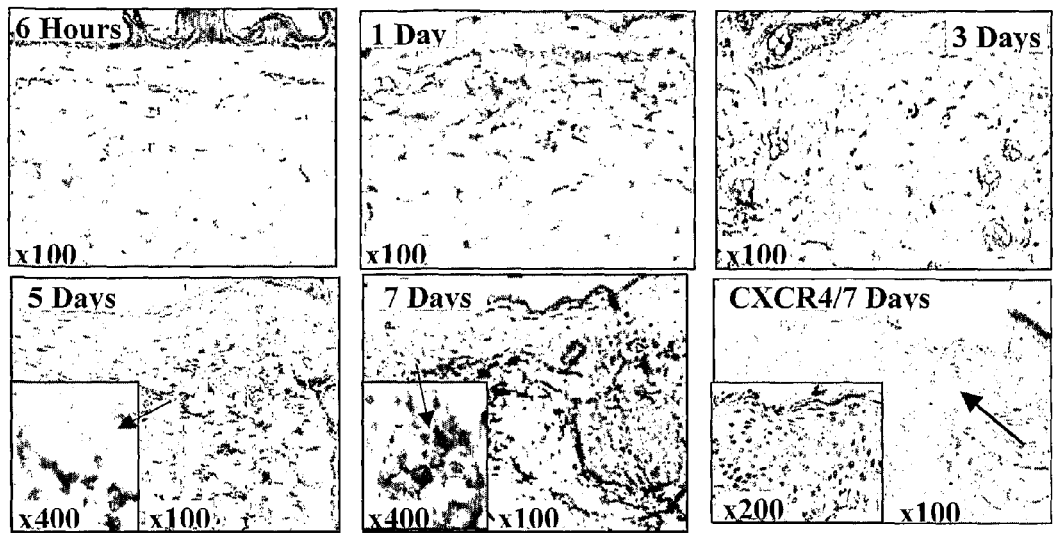
Figure 5B:
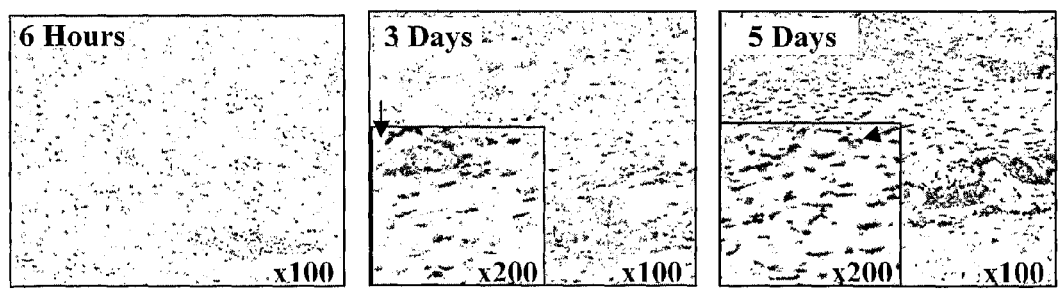

FIG. 5: The involvement of CXCL12 in rat and swine burn wound healing. Expression of CXCL12 in rat burn wound healing. A—Immunohistochemistry staining of CXCL12 of rat epidermis burned skin sections, at 6 hr (upper left panel), 1 day (upper middle panel), 3 days (upper right panel), 5 days (lower left panel) and 7 days (lower middle panel) after the burn. Staining for CXCR4 is shown at 7 days after the burn (lower right panel). (Original magnification of ×100, ×200, ×400. B—Immunohistochemistry staining of CXCL12 of rat dermis burned skin sections, at 6 hr (left panel) 72 hr (middle panel) and 120 hr (right panel) after the burn. Original magnification of ×100, ×200. C—Expression of CXCL12 in swine skin after second degree burn. Immunohistochemical staining of CXCL12 at 4 days (middle panel), 10 days (right panel) after the burn and at time 0 in normal skin (left panel). (Original magnification of ×100, ×400).

FIG. 6: Co expression of vimentin and CXCL12 in burned skin. A., Immunohistochemical staining for Vimentin of rat burned skin dermis 5 days after burn. B, CXCL12 immunohistochemical staining of consecutive tissue section of rat burned skin section 5 days after burn. (Original magnification of ×400, arrow indicates the staining for CXCL12 and Vimentin). Co-expression of GPF and CXCL12 in heterozygous mice bearing a GFP reporter knocked-in to the CX3CR1 locus burned skin. C-D, Accumulation of GFP$^+$ monocyte/dendritic cells in the dermis of injured skin. E-H, Co-expression of GFP$^+$ CXCL12 in monocyte/dendritic cells in parallel sections from dermis of injured skin, arrow indicates the staining for CXCL12 (E, G) and GFP (F, H).

FIG. 7: CXCL12 is expressed in primary cultures of fibroblasts, but not keratinocytes. A—In vitro expression of CXCL12 and CXCR4 in keratinocytes and fibroblasts. Expression of CXCL12 and CXCR4 measured by RT-PCR in primary human keratinocytes and fibroblasts. B—Expression of CXCL12 in keratinocytes and fibroblasts conditioned medium as measured by ELISA assay. C—Immunostaining of human primary fibroblasts with anti Cytokeratin antibodies as control. D—Immunostaining of human primary fibroblasts with anti CXCL12 antibodies. E—Immunostaining of human primary fibroblasts with anti CXCL12 of human primary fibroblast 2 days after wounding the fibroblasts monolayer. (Original magnification of ×200).

Figure 8:
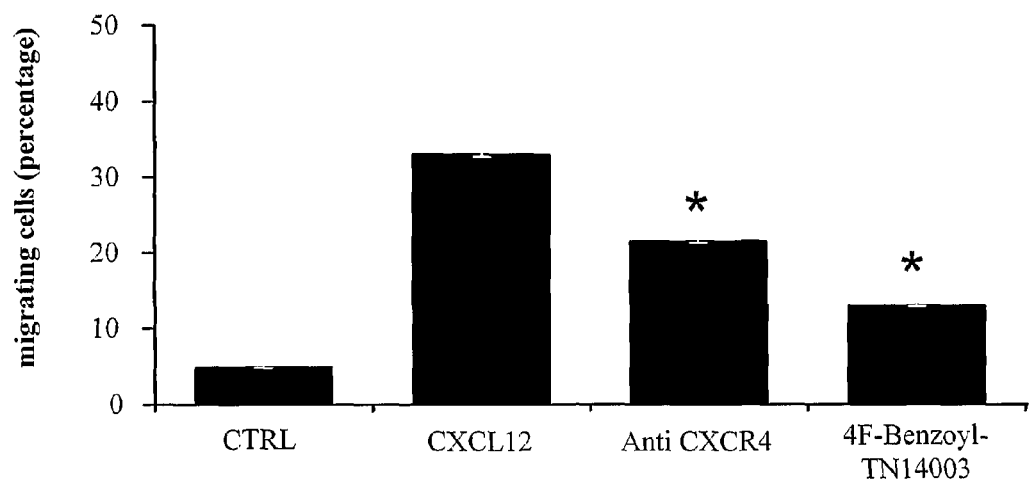

FIG. 8: Effect of neutralizing antibodies to CXCR4 and the small peptide inhibitor of CXCR4 on inflammation and regeneration of skin following burns. Migration of rat lymphocytes in response to CXCL12 (100 ng/ml) was tested in the absence and presence of neutralizing antibodies to CXCR4 (NA), or the CXCR4 antagonist-4F-benzoyl-TN14003. The results are the average of two experiments; for each experiment at least 5 rats were tested ($p<0.05$).

Figure 9A:
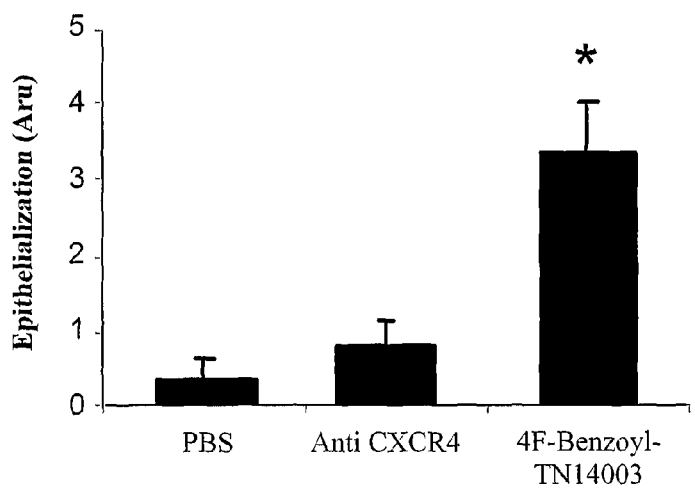
Figure 9B:
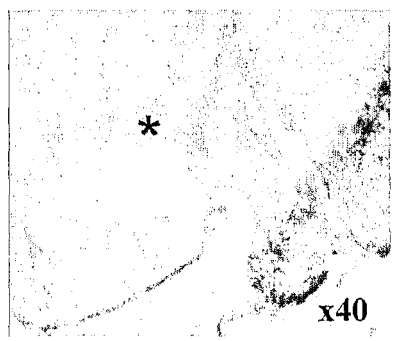
Figure 9C:
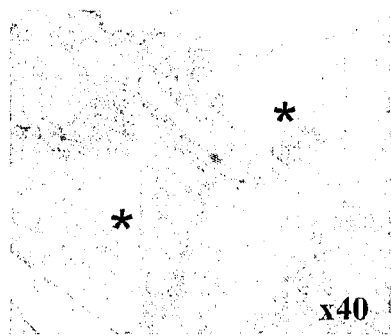

FIG. 9: Effect of neutralizing antibodies to CXCR4 and the small peptide inhibitor of CXCR4 on inflammation and regeneration of skin following burns. The effect of CXCR4 antagonists on re-epithelialization is shown in A. The results are the average of two experiments; for each experiment at least 5 rats were tested ($P<0.05$). B depicts the epithelialization of burn skin in mice treated with PBS, (Stars indicate the sites of novel epithelialization). C depicts the epithelialization of burn skin in mice treated with 4F-benzoyl-TN14003, (Stars indicate the sites of novel epithelialization).

Figure 10:
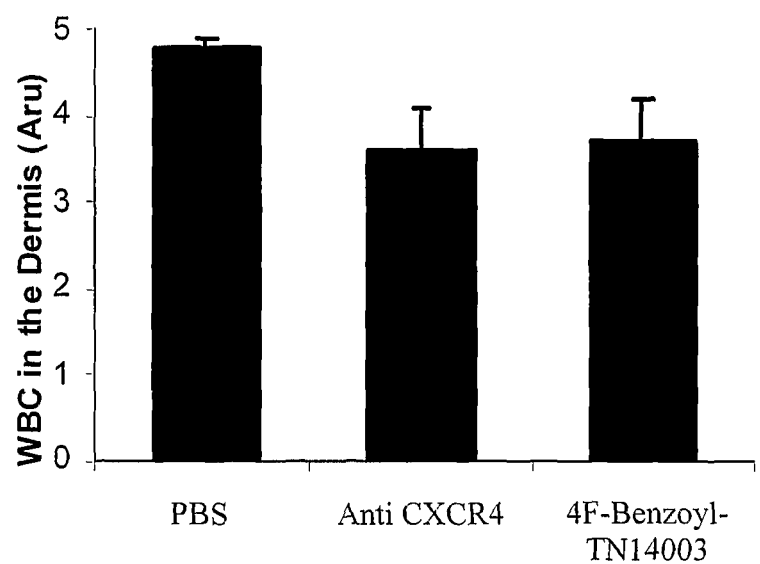

FIG. 10: Effect of neutralizing antibodies to CXCR4 and the small peptide inhibitor of CXCR4 on inflammation and regeneration of skin following burns. The number of lymphocytes in the dermis is indicated. The results are the average of two experiments; for each experiment at least 5 rats were tested ($p<0.05$).

Figure 11A:
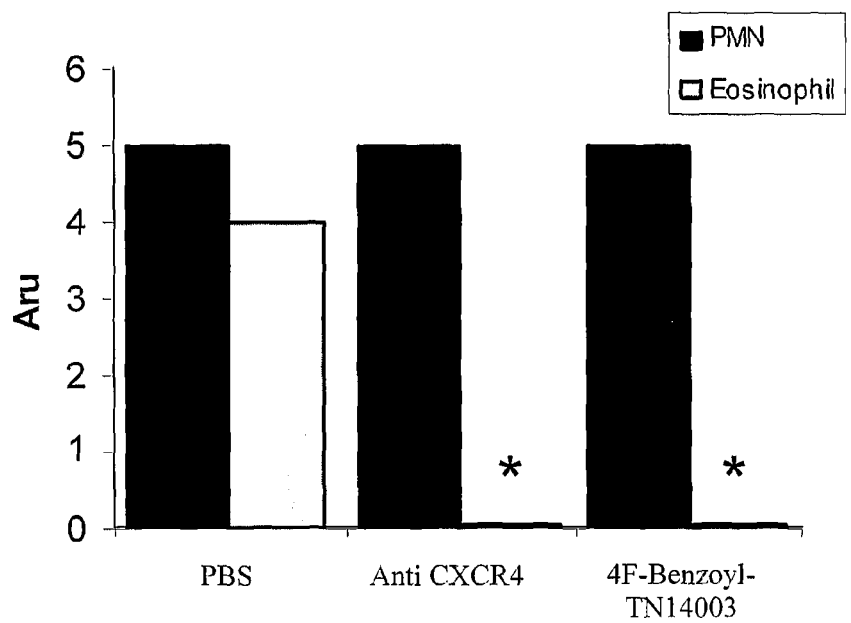
Figure 11B:
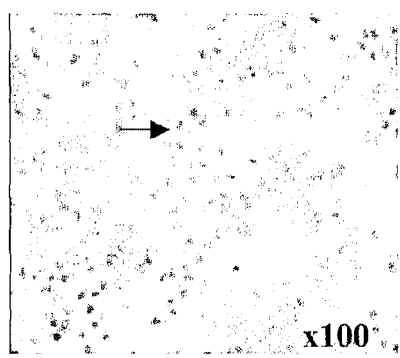
Figure 11C:
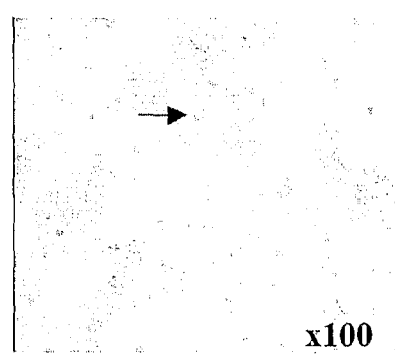

FIG. 11: Effect of neutralizing antibodies to CXCR4 and the small peptide inhibitor of CXCR4 on inflammation and regeneration of skin following burns. The number of polymorphonuclear cells (PMN) in the epidermis (black histograms) and eosinophils in the dermis (gray histograms) 5 days after burn is shown in A. B depicts the eosinophils in the dermis of mice treated with PBS, (Arrow indicate the site of eosinophilia). C depicts the eosinophils in the dermis of mice treated with 4F-benzoyl-TN14003, (A row indicate the site of eosinophilia). The results are the average of two experiments; for each experiment at least 5 rats were tested ($p<0.05$).

DETAILED DESCRIPTION OF THE INVENTION

The present invention relates to the use of inhibitors of CXCR4 for the treatment of burns and other skin lesions, as well as other conditions associated with excessive fibrosis and scar formation. Particularly, the invention provides methods of treating wounds and skin lesions, including skin burns, and other conditions associated with excessive fibrosis and scar formation, using peptide inhibitors of the T-140 family as well as other CXCR4 antagonists.

The present inventors have discovered unexpectedly, that while the presence of CXCL12 in burn blisters is involved in protecting the skin during a short period of time following skin burn injury, thereafter CXCL12 expressed on fibroblasts and endothelial cells induces the accumulation of eosinophils which in turn slow the epithelialization.

The present invention discloses for the first time the surprising discovery that treatment of partial thickness burns in a rat model with a small peptide CXCR4 antagonist of the T-140 family, namely 4F-benzoyl-TN14003, or with an anti-CXCR4 monoclonal antibody (mAb), resulted in improved epithelialization and reduced eosinophilia. It is further disclosed, that that the peptide antagonist was more potent than the neutralizing mAb in improving wound healing in vivo.

A fine balance between fibrotic tissue deposition and neovascularization on one hand and fibrotic tissue degradation and epithelization on the other should be maintained in order to assure successful wound healing. Immune cell subpopulations recruited to the burned site are involved in orchestrating these events. Unbalanced proliferation and activation of fibroblasts may lead to inadequate granulation and the formation of a fibrotic tissue. Reduced angiogenesis and blood flow into the burn wound can prevent successful epithelialization and wound repair. With regard to the CXCL12/CXCR4 axis, the inventors have unexpectedly demonstrated that upon treatment with a T-140 analog, a decrease in eosinophil migration into the wounded tissue occurs, accompanied by increased epithelization and healing of the burn wounds. The decrease in eosinophil migration into the wounded tissue and the increased epithelization observed in mice treated with the T-140 analog CXCR4 antagonist indicate that CXCL12/CXCR4 interactions are involved in shaping the balance between fibrosis and epithelialization. The invention provides compositions and methods utilizing T-140 analogs for modulating conditions associated with fibrosis and epithelialization.

T-140 Analogs

The peptides described in this specification have N-terminal (amino-terminal) at the left extremity and C-terminal (carboxyl-terminal) at the right extremity in accordance with the customary practice of peptide notations.

In this specification and drawings, the representations of amino acids, etc. by brevity codes are made by the use of the codes prescribed by IUPAC-IUB Commission on Biochemical Nomenclature or by the codes customarily used in the relevant art. Examples of such codes are shown as below. If an optical isomer exists with respect to an amino acid, it preferably represents the L form unless otherwise expressly specified.

Gly or G: glycine; Ala or A: alanine; Val or V: valine; Leu or L: leucine; Ile or I: isoleucine; Ser or S: serine; Thr or T: threonine; Cys or C: cysteine; Met or M: methionine; Glu or E: glutamic acid; Asp or D: aspartic acid; Lys or K: lysine; Arg or R: arginine; His or H: histidine; Phe or F: phenylalanine; Tyr or Y: tyrosine; Trp or W: tryptophan; Pro or P: proline; Asn or N: asparagine; Gln or Q: glutamine; pGlu: pyroglutamic acid; Nal: 3-(2-naphthyl) alanine; Cit: citrulline; DLys: D-lysine; DCit: D-citrulline; DGlu: D-glutamic acid; Me: methyl group; Et: ethyl group; Bu: butyl group; Ph: phenyl group.

The substituents, protective group and reagents often used in this specification are indicated by the following codes.

| | |
|---|---|
| BHA: | benzhydrylamine |
| pMBHA: | p-methylbenzhydrylamine |
| Tos: | p-toluenesulphonyl |
| CHO: | formyl |
| HONB: | N-hydroxy-5-norbornene-2,3-dicarboximide |
| OcHex: | cyclohexyl ester |
| Bzl: | benzyl |
| $Cl_2$-Bzl: | dichloro-benzyl |
| Bom: | benzyloxymethyl |
| Z: | benzyloxycarbonyl |
| Br-Z: | 2-bromobenzyloxycarbonyl |
| Boc: | t-butyloxycarbonyl |
| DCM: | dichloromethane |
| HOBt: | 1-hydroxybenzotriazole |
| DCC: | N,N'-dicyclohexylcarbodiimide |
| TFA: | trifluoroacetic acid |
| DIEA: | diisopropylethylamine |
| Fmoc: | N-9-fluorenylmethoxycarbony |
| DNP: | dinitrophenyl |
| Bum | tertiarybutoxymethyl |
| Trt: | trityl |
| Ac: | acetyl |
| Guanyl: | guanyl |
| Succinyl: | succinyl |
| glutaryl: | glutaryl |
| TMguanyl: | tetramethylguanyl |
| 2F-benzoyl: | 2-fluorobenzoyl |
| 4F-benzoyl: | 4-fluorobenzoyl |
| APA: | 5-aminopentanoyl |
| ACA: | 6-aminohexanoyl |
| desamino-Arg: | 2-desamino-arginyl | deamino TMG-APA: the following formula (IV):

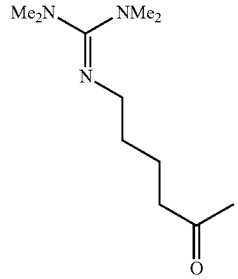

(IV)

R—CH2: the following formula (V):

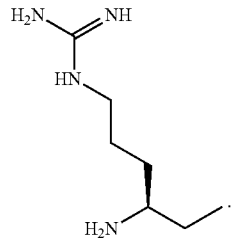

(V)

In amino acids of N-terminal peptide, [H-] indicates that the terminal amino group is not derivatized, and in amino acids of C-terminal peptide, [—OH] indicates that the terminal carboxyl group is not derivatized.

The preferable peptide inhibitors according to the invention are analogs and derivatives of T-140, a known peptide having the amino acid sequence H-Arg-Arg-Nal-Cys-Tyr-Arg-Lys-DLys-Pro-Tyr-Arg-Cit-Cys-Arg-OH (SEQ ID NO:69, Tamamura et al., 2003).

The preferable peptides of the invention include analogs and derivatives disclosed in patent applications WO2002/020561 and WO 2004/020462.

In one aspect, the present invention relates to the use of pharmaceutical compositions comprising as an active ingredient a peptide indicated by the following formula (I) or a salt thereof:

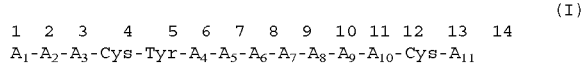

$$A_1\text{-}A_2\text{-}A_3\text{-}Cys\text{-}Tyr\text{-}A_4\text{-}A_5\text{-}A_6\text{-}A_7\text{-}A_8\text{-}A_9\text{-}A_{10}\text{-}Cys\text{-}A_{11} \quad (I)$$

wherein:

$A_1$ in the above-mentioned formula (I) represents an arginine, lysine, ornithine, citrulline, alanine or glutamic acid residue (either L or D form) which may be derivatized at the N-terminal, or $A_1$ is deleted, or it is preferable that $A_1$ is an arginine, citrulline, alanine or D-glutamic acid residue, or $A_1$ is deleted.

Examples of "N-terminal derivatized peptides" or "N-α-substituted derivatives" include, but are not limited to, those protected by formyl group; acyl group, e.g., acetyl group, propionyl group, butyryl group, pentanoyl group, C2-6alkanoyl group e.g. hexanoyl group, benzoyl group, arylcarbonyl group e.g. substituted benzoyl group (e.g.: 2-fluorobenzoyl, 3-fluorobenzoyl group, 4-fluorobenzoyl group, 2-bromobenzoyl group, 3-bromobenzoyl group, 4-bromobenzoyl group, 2-nitrobenzoyl group, 3-nitrobenzoyl group, 4-nitrobenzoyl group), succinyl group, glutaryl group; nicotinyl group; isonicotinyl group; alkylsulfonyl group (e.g.: methanesulfonyl group, ethanesulfonyl group, propanesulfonyl group, camphorsulfonyl group); arylsulfonyl group (e.g.: p-toluenesulfonyl group, 4-fluorobenzenesulfonyl group, mesitylenesulfonyl group, 4-aminobenzenesulfonyl group, dansyl group, 4-bromobenzenesulfonyl group) etc. Or, the amino acid group of N-terminal may be deleted.

$A_2$ in the above-mentioned formula (I) represents an arginine or glutamic acid residue (either L or D form) if A1 is an arginine, lysine, ornithine, citrulline, alanine or glutamic acid residue (either L or D form) which may be derivatized at the N-terminal, or $A_2$ represents an arginine or glutamic acid residue (either L or D form) which may be derivatized at the N-terminal if $A_1$ is deleted, or it is preferable that $A_2$ is an arginine or glutamic acid residue if $A_1$ is an arginine, citrulline, alanine or glutamic acid residue which may be derivatized at the N-terminal, or $A_2$ is an arginine or glutamic acid residue which may be derivatized at N-terminal if $A_1$ is deleted. Examples of "peptides derivatized at the N-terminal" include, but are not limited to, the same ones as those mentioned in A1.

$A_3$ in the above-mentioned formula (I) represents an aromatic amino acid residue (e.g., phenylalanine, tryptophan, 3-(2-naphthyl)alanine, tyrosine, 4-fluorophenylalanine, 3-(1-naphthyl)alanine (either L or D form), or preferably, $A_3$ represents phenylalanine, tryptophan or 3-(2-naphthyl)alanine.

$A_4$ in the above-mentioned formula (I) represents an arginine, lysine, ornithine, citrulline, alanine or glutamic acid residue (either L or D form), or it is preferable that $A_4$ is an arginine, citrulline, alanine or L- or D-glutamic acid residue.

$A_5$ in the above-mentioned formula (I) represents an arginine, lysine, ornithine, citrulline, alanine or glutamic acid residue (either L or D form), or it is preferable that $A_5$ is an arginine, citrulline, alanine, lysine or glutamic acid residue.

$A_6$ in the above-mentioned formula (I) represents a proline, glycine, ornithine, lysine, alanine, citrulline, arginine or glutamic acid residue (either L or D form), or it is preferable that $A_6$ is a D-lysine, D-alanine, D-citrulline or D-glutamic acid residue.

$A_7$ in the above-mentioned formula (I) represents a proline, glycine, ornithine, lysine, alanine, citrulline or arginine residue (either L or D form), or it is preferable that $A_7$ is a proline or alanine residue.

$A_8$ in the above-mentioned formula (I) represents a tyrosine, phenylalanine, alanine, naphthylalanine, citrulline or glutamic acid residue (either L or D form), or it is preferable that $A_8$ is a tyrosine, alanine or D-glutamic acid residue.

$A_9$ in the above-mentioned formula (I) represents an arginine, lysine, ornithine, citrulline, alanine or glutamic acid residue (either L or D form), or it is preferable that $A_9$ is an arginine, citrulline or glutamic acid residue.

$A_{10}$ in the above-mentioned formula (I) represents a citrulline, glutamic acid, arginine or lysine residue (either L or D form), or it is preferable that $A_{10}$ is a citrulline or D-glutamic acid residue.

$A_{11}$ in the above-mentioned formula (I) represents an arginine, glutamic acid, lysine or citrulline residue (either L or D form) which may be derivatized at C-terminal, or it is preferable that $A_{11}$ is an arginine or glutamic acid residue which may be derivatized at C-terminal.

"C-terminal derivatization" or "C-terminal carboxyl derivatization" includes, without limitation, amidation (—$CONH_2$, —CONHR, —CONRR') and esterification (—COOR). Herein, R and R' in amides and esters include, for example, $C_{1-6}$ alkyl group e.g. methyl, ethyl, n-propyl, iso-propyl, or n-butyl, $C_{3-8}$ cycloalkyl group e.g. cyclopentyl, cyclohexyl, $C_{6-12}$ aryl group e.g. phenyl and α-naphthyl, phenyl-$C_{1-2}$ alkyl group e.g. benzyl, phenethyl or $C_{7-14}$ aralkyl group e.g. $C_{1-2}$ alkyl group e.g. α-naphthyl methyl group, and additionally, pivaloyloxymethyl group which is generally used as an oral bioavailable ester.

If a peptide of the present invention has carboxy groups (or carboxylates) at side-chain terminals other than C-terminal, the peptide having amidated or esterificated carboxy groups at side-chain terminals is included in the peptides of the present invention. As the amides and esters in this case, for example, the amides and esters exemplified in $A_{11}$ are similarly used. Also, the peptides of the present invention include peptides in which substituents (e.g. —OH, —SH, amino group, imidazole group, indole group, guanidino group, etc.) on the intramolecular amino acid side chains are protected by suitable protective group (e.g. C1-6 acyl group, C2-6 alkanoyl such as formyl group, acetyl group, etc.), or complex peptides such as glycopeptides combined with sugar chain in the above-mentioned peptides.

Salts of the peptides of the present invention include physiologically acceptable salts of acids or bases and particularly, physiologically acceptable acid addition salts are preferable. Such salts are exemplified by salts of inorganic acids (e.g. hydrochloric acid, phosphoric acid, hydrobromic acid, sulfuric acid), or salts of organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

In one embodiment, the composition comprises a peptide as set forth in formula (I) as defined hereinabove, wherein $A_1$ is a glutamic acid residue or is deleted.

In another embodiment, the composition comprises a peptide as set forth in formula (I) as defined hereinabove, wherein $A_4$ is a glutamic acid residue.

In another embodiment, the composition comprises a peptide as set forth in formula (I) as defined hereinabove, wherein $A_6$ is a glutamic acid residue.

In another embodiment, the composition comprises a peptide as set forth in formula (I) as defined hereinabove, wherein $A_8$ is a glutamic acid residue.

In another embodiment, the composition comprises a peptide as set forth in formula (I) as defined hereinabove, wherein $A_9$ is a glutamic acid residue.

In another embodiment, the composition comprises a peptide as set forth in formula (I) as defined hereinabove, wherein $A_5$ is an arginine or glutamic acid residue.

In another embodiment, the composition comprises a peptide as set forth in formula (I) as defined hereinabove, wherein $A_{10}$ is a glutamic acid, arginine or lysine residue.

In another embodiment, the composition comprises a peptide as set forth in formula (I) as defined hereinabove, wherein $A_{11}$ is a glutamic acid, lysine or citrulline residue.

In another embodiment, the peptide has an amino acid sequence as set forth in any one of SEQ ID NOS:1-71 presented in Table 1 herein:

TABLE 1

T-140 and currently preferred T-140 analogs

| Analog | SEQ ID NO: | Amino acid sequence |
|---|---|---|
| AcTC14003 | 1 | Ac-Arg-Arg-Nal-Cys-Tyr-Cit-Lys-DLys-Pro-Tyr-Arg-Cit-Cys-Arg-OH |
| AcTC14005 | 2 | Ac-Arg-Arg-Nal-Cys-Tyr-Arg-Lys-DCit-Pro-Tyr-Arg-Cit-Cys-Arg-OH |
| AcTC14011 | 3 | Ac-Arg-Arg-Nal-Cys-Tyr-Cit-Lys-DCit-Pro-Tyr-Arg-Cit-Cys-Arg-OH |
| AcTC14013 | 4 | Ac-Arg-Arg-Nal-Cys-Tyr-Cit-Lys-DLys-Pro-Tyr-Cit-Cys-Arg-OH |
| AcTC14015 | 5 | Ac-Cit-Arg-Nal-Cys-Tyr-Cit-Lys-DLys-Pro-Tyr-Arg-Cit-Cys-Arg-OH |
| AcTC14017 | 6 | Ac-Cit-Arg-Nal-Cys-Tyr-Arg-Lys-DCit-Pro-Tyr-Arg-Cit-Cys-Arg-OH |
| AcTC14019 | 7 | Ac-Arg-Arg-Nal-Cys-Tyr-Arg-Lys-DCit-Pro-Tyr-Cit-Cys-Arg-OH |
| AcTC14021 | 8 | Ac-Cit-Arg-Nal-Cys-Tyr-Arg-Lys-DLys-Pro-Tyr-Cit-Cys-Arg-OH |
| AcTC14012 | 9 | Ac-Arg-Arg-Nal-Cys-Tyr-Cit-Lys-DCit-Pro-Tyr-Arg-Cit-Cys-Arg-NH$_2$ |
| AcTC14014 | 10 | Ac-Arg-Arg-Nal-Cys-Tyr-Cit-Lys-DLys-Pro-Tyr-Cit-Cys-Arg-NH$_2$ |
| AcTC14016 | 11 | Ac-Cit-Arg-Nal-Cys-Tyr-Cit-Lys-DLys-Pro-Tyr-Arg-Cit-Cys-Arg-NH$_2$ |
| AcTC14018 | 12 | Ac-Cit-Arg-Nal-Cys-Tyr-Arg-Lys-DCit-Pro-Tyr-Arg-Cit-Cys-Arg-NH$_2$ |
| AcTC14020 | 13 | Ac-Arg-Arg-Nal-Cys-Tyr-Arg-Lys-DCit-Pro-Tyr-Cit-Cys-Arg-NH$_2$ |
| AcTC14022 | 14 | Ac-Cit-Arg-Nal-Cys-Tyr-Arg-Lys-DLys-Pro-Tyr-Cit-Cys-Arg-NH$_2$ |
| TE14001 | 15 | H-DGlu-Arg-Nal-Cys-Tyr-Arg-Lys-DLys-Pro-Tyr-Arg-Cit-Cys-Arg-OH |
| TE14002 | 16 | H-Arg-Glu-Nal-Cys-Tyr-Arg-Lys-DLys-Pro-Tyr-Arg-Cit-Cys-Arg-OH |
| TE14003 | 17 | H-Arg-Arg-Nal-Cys-Tyr-Glu-Lys-DLys-Pro-Tyr-Arg-Cit-Cys-Arg-OH |
| TE14004 | 18 | H-Arg-Arg-Nal-Cys-Tyr-Arg-Glu-DLys-Pro-Tyr-Arg-Cit-Cys-Arg-OH |
| TE14005 | 19 | H-Arg-Arg-Nal-Cys-Tyr-Arg-Lys-DGlu-Pro-Tyr-Arg-Cit-Cys-Arg-OH |
| TE14006 | 20 | H-Arg-Arg-Nal-Cys-Tyr-Arg-Lys-DLys-Pro-Tyr-Glu-Cit-Cys-Arg-OH |
| TE14007 | 21 | H-Arg-Arg-Nal-Cys-Tyr-Arg-Lys-DLys-Pro-Tyr-Arg-Cit-Cys-Glu-OH |
| TE14011 | 22 | H-Arg-Arg-Nal-Cys-Tyr-Cit-Lys-DGlu-Pro-Tyr-Arg-Cit-Cys-Arg-NH$_2$ |
| TE14012 | 23 | H-Arg-Arg-Nal-Cys-Tyr-DGlu-Lys-DCit-Pro-Tyr-Arg-Cit-Cys-Arg-NH$_2$ |
| TE14013 | 24 | H-Arg-Arg-Nal-Cys-Tyr-DGlu-Lys-DGlu-Pro-Tyr-Arg-Cit-Cys-Arg-NH$_2$ |
| TE14014 | 25 | H-DGlu-Arg-Nal-Cys-Tyr-Cit-Lys-DGlu-Pro-Tyr-Arg-Cit-Cys-Arg-NH$_2$ |
| TE14015 | 26 | H-Arg-Arg-Nal-Cys-Tyr-Cit-Lys-DGlu-Pro-DGlu-Arg-Cit-Cys-Arg-NH$_2$ |
| TE14016 | 27 | H-Arg-Arg-Nal-Cys-Tyr-Cit-Lys-DGlu-Pro-Tyr-DGlu-Cys-Arg-NH$_2$ |
| AcTE14014 | 28 | Ac-DGlu-Arg-Nal-Cys-Tyr-Cit-Lys-DGlu-Pro-Tyr-Arg-Cit-Cys-Arg-NH$_2$ |
| AcTE14015 | 29 | Ac-Arg-Arg-Nal-Cys-Tyr-Cit-Lys-DGlu-Pro-DGlu-Arg-Cit-Cys-Arg-NH$_2$ |
| AcTE14016 | 30 | Ac-Arg-Arg-Nal-Cys-Tyr-Cit-Lys-DGlu-Pro-Tyr-DGlu-Cys-Arg-NH$_2$ |
| TF1: AcTE14011 | 31 | Ac-Arg-Arg-Nal-Cys-Tyr-Cit-Lys-DGlu-Pro-Tyr-Arg-Cit-Cys-Arg-NH$_2$ |
| TF2: guanyl-TE14011 | 32 | guanyl-Arg-Arg-Nal-Cys-Tyr-Cit-Lys-DGlu-Pro-Tyr-Arg-Cit-Cys-Arg-NH$_2$ |
| TF3: TMguanyl-TE14011 | 33 | TMguanyl-Arg-Arg-Nal-Cys-Tyr-Cit-Lys-DGlu-Pro-Tyr-Arg-Cit-Cys-Arg-NH$_2$ |
| TF4: TMguanyl-TE1011 (2-14) | 34 | TMguanyl-Arg-Nal-Cys-Tyr-Cit-Lys-DGlu-Pro-Tyr-Arg-Cit-Cys-Arg-NH$_2$ |
| TF5: 4F-benzoyl-TE14011 | 35 | 4F-benzoyl-Arg-Arg-Nal-Cys-Tyr-Cit-Lys-DGlu-Pro-Tyr-Arg-Cit-Cys-Arg-NH$_2$ |
| TF6: 2F-benzoyl-TE14011 | 36 | 2F-benzoyl-Arg-Arg-Nal-Cys-Tyr-Cit-Lys-DGlu-Pro-Tyr-Arg-Cit-Cys-Arg-NH$_2$ |
| TF7: APA-TE14011 (2-14) | 37 | APA-Arg-Nal-Cys-Tyr-Cit-Lys-DGlu-Pro-Tyr-Arg-Cit-Cys-Arg-NH$_2$ |
| TF8: desamino-R-TE14011 (2-14) | 38 | desamino-R-Arg-Nal-Cys-Tyr-Cit-Lys-DGlu-Pro-Tyr-Arg-Cit-Cys-Arg-NH$_2$ |
| TF9: guanyl-TE14011 (2-14) | 39 | Guanyl-Arg-Nal-Cys-Tyr-Cit-Lys-DGlu-Pro-Tyr-Arg-Cit-Cys-Arg-NH$_2$ |

TABLE 1-continued

T-140 and currently preferred T-140 analogs

| Analog | SEQ ID NO: | Amino acid sequence |
|---|---|---|
| TF10: succinyl-TE14011 (2-14) | 40 | succinyl-Arg-Nal-Cys-Tyr-Cit-Lys-DGlu-Pro-Tyr-Arg-Cit-Cys-Arg-NH$_2$ |
| TF11: glutaryl-TE14011 (2-14) | 41 | glutaryl-Arg-Nal-Cys-Tyr-Cit-Lys-DGlu-Pro-Tyr-Arg-Cit-Cys-Arg-NH$_2$ |
| TF12: deaminoTMG-APA-TE14011 (2-14) | 42 | deaminoTMG-APA-Arg-Nal-Cys-Tyr-Cit-Lys-DGlu-Pro-Tyr-Arg-Cit-Cys-Arg-NH$_2$ |
| TF15: H-Arg-CH2NH-RTE14011 (2-14) | 43 | R—CH2-Arg-Nal-Cys-Tyr-Cit-Lys-DGlu-Pro-Tyr-Arg-Cit-Cys-Arg-NH$_2$ |
| TF17: TE14011 (2-14) | 44 | H-Arg-Nal-Cys-Tyr-Cit-Lys-DGlu-Pro-Tyr-Arg-Cit-Cys-Arg-NH$_2$ |
| TF18: TMguanyl-TC14012 | 45 | TMguanyl-Arg-Arg-Nal-Cys-Tyr-Cit-Lys-DCit-Pro-Tyr-Arg-Cit-Cys-Arg-NH$_2$ |
| TF19: ACA-TC14012 | 46 | ACA-Arg-Arg-Nal-Cys-Tyr-Cit-Lys-DCit-Pro-Tyr-Arg-Cit-Cys-Arg-NH$_2$ |
| TF20: ACA-T140 | 47 | ACA-Arg-Arg-Nal-Cys-Tyr-Arg-Lys-DLys-Pro-Tyr-Arg-Cit-Cys-Arg-OH |
| TZ14011 | 48 | H-Arg-Arg-Nal-Cys-Tyr-Cit-Arg-DLys-Pro-Tyr-Arg-Cit-Cys-Arg-NH$_2$ |
| AcTZ14011 | 49 | Ac-Arg-Arg-Nal-Cys-Tyr-Cit-Arg-DLys-Pro-Tyr-Arg-Cit-Cys-Arg-NH$_2$ |
| AcTN14003 | 50 | Ac-Arg-Arg-Nal-Cys-Tyr-Cit-Lys-DLys-Pro-Tyr-Arg-Cit-Cys-Arg-NH$_2$ |
| AcTN14005 | 51 | Ac-Arg-Arg-Nal-Cys-Tyr-Arg-Lys-DCit-Pro-Tyr-Arg-Cit-Cys-Arg-NH$_2$ |
| 4F-benzoyl-TN14003 | 52 | 4F-benzoyl-Arg-Arg-Nal-Cys-Tyr-Cit-Lys-DLys-Pro-Tyr-Arg-Cit-Cys-Arg-NH$_2$ |
| 4F-benzoyl-TN14011-Me | 53 | 4F-benzoyl-Arg-Arg-Nal-Cys-Tyr-Cit-Lys-DGlu-Pro-Tyr-Arg-Cit-Cys-Arg-NHMe |
| 4F-benzoyl-TN14011-Et | 54 | 4F-benzoyl-Arg-Arg-Nal-Cys-Tyr-Cit-Lys-DGlu-Pro-Tyr-Arg-Cit-Cys-Arg-NHEt |
| 4F-benzoyl-TN14011-iPr | 55 | 4F-benzoyl-Arg-Arg-Nal-Cys-Tyr-Cit-Lys-DGlu-Pro-Tyr-Arg-Cit-Cys-Arg-NHiPr |
| 4F-benzoyl-TN14011-tyramine | 56 | 4F-benzoyl-Arg-Arg-Nal-Cys-Tyr-Cit-Lys-DGlu-Pro-Tyr-Arg-Cit-Cys-Arg-tyramine |
| TA14001 | 57 | H-Ala-Arg-Nal-Cys-Tyr-Arg-Lys-DLys-Pro-Tyr-Arg-Cit-Cys-Arg-OH |
| TA14005 | 58 | H-Arg-Nal-Cys-Tyr-Ala-Lys-DLys-Pro-Tyr-Arg-Cit-Cys-Arg-OH |
| TA14006 | 59 | H-Arg-Arg-Nal-Cys-Tyr-Arg-Ala-DLys-Pro-Tyr-Arg-Cit-Cys-Arg-OH |
| TA14007 | 60 | H-Arg-Arg-Nal-Cys-Tyr-Arg-Lys-DALa-Pro-Tyr-Arg-Cit-Cys-Arg-OH |
| TA14008 | 61 | H-Arg-Arg-Nal-Cys-Tyr-Arg-Lys-DLys-Ala-Tyr-Arg-Cit-Cys-Arg-OH |
| TA14009 | 62 | H-Arg-Arg-Nal-Cys-Tyr-Arg-Lys-DLys-Pro-Ala-Arg-Cit-Cys-Arg-OH |
| TA14010 | 63 | H-Arg-Arg-Nal-Cys-Tyr-Arg-Lys-DLys-Pro-Tyr-Ala-Cit-Cys-Arg-OH |
| TC14001 | 64 | H-Cit-Arg-Nal-Cys-Tyr-Arg-Lys-DLys-Pro-Tyr-Arg-Cit-Cys-Arg-OH |
| TC14003 | 65 | H-Arg-Arg-Nal-Cys-Tyr-Cit-Lys-DLys-Pro-Tyr-Arg-Cit-Cys-Arg-OH |
| TN14003 | 66 | H-Arg-Arg-Nal-Cys-Tyr-Cit-Lys-DLys-Pro-Tyr-Arg-Cit-Cys-Arg-NH$_2$ |
| TC14004 | 67 | H-Arg-Arg-Nal-Cys-Tyr-Arg-Cit-DLys-Pro-Tyr-Arg-Cit-Cys-Arg-OH |
| TC14012 | 68 | H-Arg-Nal-Cys-Tyr-Cit-Lys-DCit-Pro-Tyr-Arg-Cit-Cys-Arg-NH$_2$ |
| T-140 | 69 | H-Arg-Arg-Nal-Cys-Tyr-Arg-Lys-DLys-Pro-Tyr-Arg-Cit-Cys-Arg-OH |
| TC14011 | 70 | H-Arg-Arg-Nal-Cys-Tyr-Cit-Lys-DCit-Pro-Tyr-Arg-Cit-Cys-Arg-OH |
| TC14005 | 71 | H-Arg-Arg-Nal-Cys-Tyr-Arg-Lys-DCit-Pro-Tyr-Arg-Cit-Cys-Arg-OH |

In each one of SEQ ID NOS:1-71, two cysteine residues are preferably coupled in a disulfide bond.

Currently preferred peptide inhibitors according to the present invention are peptides having an amino acid sequence as set forth in any one of SEQ ID NOS:1-71. It has been previously reported that the T-140 derivatives having an amino acid sequence as set forth in any one of SEQ ID NOS:1-68 and 70-71 presented in Table 1 may have improved stability in serum and reduced cytotoxicity relative to T-140 (SEQ ID NO:69). However, T-140 may be suitable for use in the methods of the present invention, e.g. when applied topically or by other local administration routes.

In one particular embodiment, said peptide has an amino acid sequence as set forth in SEQ ID NO:65 or an analog or derivative thereof retaining its active properties with respect to wound treatment as described herein.

In another particular embodiment, said peptide has an amino acid sequence as set forth in any one of SEQ ID NOS:1-3, 9, 45, 46, 50-56, 65, 66, 68, 70 and 71. In another particular embodiment, said peptide has an amino acid sequence as set forth in any one of SEQ ID NOS:3, 9, 45, 46, 68 and 70. In another particular embodiment, said peptide has an amino acid sequence as set forth in any one of SEQ ID NOS:1, 50, 52, 65 and 66. In another particular embodiment, said peptide has an amino acid sequence as set forth in any one of SEQ ID NOS:53-56.

In a preferable particular embodiment, said peptide has an amino acid sequence as set forth in SEQ ID NO:52.

In another particular embodiment, said peptide has an amino acid sequence as set forth in SEQ ID NO:1.

In another particular embodiment, said peptide has an amino acid sequence as set forth in SEQ ID NO:50.

In another particular embodiment, said peptide has an amino acid sequence as set forth in SEQ ID NO:66.

In another aspect, the invention relates to the use of a pharmaceutical composition comprising a peptide indicated by the following formula (II) or a salt thereof:

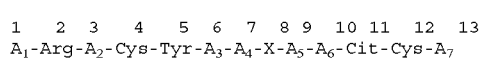

wherein:

$A_1$ represents a hydrogen atom, or an arginine, lysine, ornithine, citrulline or alanine residue or a residue of N-α-substituted derivative of these amino acids;

$A_2$ represents an aromatic amino acid residue;

$A_3$, $A_4$ and $A_6$ each independently represent an arginine, lysine, ornithine, citrulline or alanine residue;

$A_5$ represents a tyrosine, phenylalanine, alanine, naphthylalanine or citrulline residue;

$A_7$ represents a lysine or arginine residue in which a carboxyl group may be amidated or esterified;

X is selected from the group consisting of:
(i) a peptide residue represented by the following formula (III):

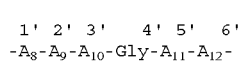

wherein $A_8$ and $A_{12}$ each independently represents an alanine, valine, leucine, isoleucine, serine, cysteine or methionine residue;

$A_9$ represents an aromatic amino acid residue, $A_{10}$ is selected from the same amino acid residues as in $A_3$, $A_{11}$ represents a tyrosine, phenylalanine, tryptophan, alanine, valine, leucine, isoleucine, serine, cysteine or methionine residue, provided that when both of the 1'-position and the 6'-position are cysteine residues, they may be bonded in a disulfide bond, (ii) a peptide selected from the group consisting of a D-ornithyl-proline, prolyl-D-ornithine, D-lysyl-proline, prolyl-D-lysine, D-arginyl-proline, prolyl-D-arginine, D-citrullyl-proline, D-citrullyl-alanine, D-alanyl-citrulline, prolyl-D-citrulline, glycyl-ornithine, ornithyl-glycine, glycyl-lysine, lysyl-glycine, glycyl-arginine, arginyl-glycine, glycyl-citrulline, citrullyl-glycine, D-alanyl-proline, and D-lysyl-alanine, and a hydrogen atom of a side chain ω-amino group of D-arginine, L-arginine, D-lysine, L-lysine, D-ornithine or L-ornithine which are constitutional amino acids of said peptide residues may be substituted by a ω-aminoacyl group, and the peptide residues of (i) and (ii) represent a peptide residue which binds amino acid residues at the 7-position and the 9-position through a peptide bond;

and the cysteine residues at the 4-position and the 12-position may be bonded in a disulfide bond;

provided that, in the above polypeptide or a salt thereof, either of the amino acid residues of $A_1$, $A_3$, $A_4$, $A_5$, $A_6$ and $A_7$ is an alanine or citrulline residue; or (iii) a peptide residue containing a D-citrulline, D-alanine, citrulline, or alanine residue) or a salt thereof.

In the polypeptides of the formula (II) of the present invention, $A_1$ is preferably an arginine, alanine or citrulline residue; $A_2$ is preferably a tryptophan or naphthylalanine residue; $A_3$ is preferably arginine, alanine or citrulline residue; $A_4$ is preferably a lysine, alanine or citrulline residue; X is preferably a D-lysyl-proline, D-alanyl-proline, D-lysyl-alanine or D-citrullyl-proline residue; $A_5$ is preferably a tyrosine or alanine residue; $A_6$ is preferably an arginine, alanine or citrulline residue; $A_7$ is preferably an arginine residue.

Exemplary peptides of the formula (II) are peptides wherein $A_1$, $A_6$ and $A_7$ are arginine residues, $A_2$ is a naphthylalanine residue, $A_3$ is a citrulline residue, $A_4$ is a lysine residue, X is a D-lysyl-proline residue, and $A_5$ is a tyrosine residue, a polypeptide of the formula (II) wherein $A_1$, $A_3$, $A_6$ and $A_7$ are arginine residues, $A_2$ is a naphthylalanine residue, $A_4$ is a lysine residue, X is a D-citrullyl-proline residue, and $A_5$ is a tyrosine residue, a polypeptide of the formula (II) wherein $A_1$, $A_6$ and $A_7$ are arginine residues, $A_2$ is a naphthylalanine residue, $A_3$ is a citrulline residue, $A_4$ is a lysine residue, X is a D-citrullyl-proline residue, $A_5$ is a tyrosine residue, and a polypeptide of the formula (II) wherein $A_1$ is a citrulline residue, $A_2$ is a naphthylalanine residue, $A_3$, $A_6$ and $A_7$ are arginine residues, $A_4$ is a lysine residue, X is a D-citrullyl-proline residue, $A_5$ is a tyrosine residue.

The peptides of formula (II) may be exemplified in another embodiment by a peptide of the formula (II) wherein $A_1$, $A_6$ and $A_7$ are arginine residues, $A_2$ is a naphthylalanine residue, $A_3$ is a alanine residue, $A_4$ is a lysine residue, X is a D-lysyl-proline residue, and $A_4$ is a tyrosine residue, a polypeptide of the formula (II) wherein $A_1$ is a citrulline residue, $A_2$ is a naphthylalanine residue, $A_3$, $A_6$ and $A_7$ are arginine residues, $A_4$ is a lysine residue, X is a D-lysyl-proline residue, and $A_5$ is a tyrosine residue, a polypeptide of the formula (II) wherein $A_1$, $A_3$ and $A_7$ are arginine residues, $A_2$ is a naphthylalanine residue, $A_4$ is a lysine residue, X is a D-lysyl-proline residue, $A_5$ is a tyrosine residue, and $A_6$ is a citrulline residue, a polypeptide of the formula (II) wherein $A_1$ and $A_3$ are citrulline residues, $A_2$ is a naphthylalanine residue, $A_4$ is a lysine residue, X is a D-lysyl-proline residue, $A_5$ is a tyrosine residue, $A_6$ and $A_7$ are arginine residues, and a polypeptide of the formula (II) wherein $A_1$, $A_3$ and $A_7$ are arginine residues, $A_2$ is a naphthylalanine residue, $A_4$ is a lysine residue, X is a D-citrullyl-proline residue, $A_5$ is a tyrosine residue, and $A_6$ is a citrulline residue.

The amino acid of $A_7$ as presented in formula II herein is preferably one in which the carboxyl group is amidated for improving stability of the polypeptide in vivo such as in serum, etc.

A peptide of the present invention includes a peptide or its amide, ester or salt containing the amino acid sequence which is the substantially same amino acid sequence as the sequence of any of the above-mentioned peptides. Here, "the substantially same amino acid sequence" means the amino acid sequence qualitatively identical in the activity of the peptide (e.g. the inhibitory activity on the interaction of a ligand and a receptor) or the biological activity of the peptide with respect to wound healing (e.g. increased epithelialization) or the like. Accordingly, quantitative variances are acceptable to some extent (e.g. about 0.01 to 100 times, preferably 0.5 to 20 times, or more preferably 0.5 to 2 times). Therefore, one or more of the amino acids in the amino acid sequences indicated in any of the above-mentioned formula (I), (II) and SEQ ID NOS:1-71 can have variances, so far as they have any of the above-mentioned properties. That is to say, in the present invention, any peptide (variant peptide) resulting from the variance in the amino acid sequence such as substitution, deletion or insertion (addition) etc. which brings about any serious (significant) change (i.e. a qualitatively different change, or a qualitatively identical but quantitatively significantly different change) in the physiological property or chemical property of the original (non-variant) peptide is deemed as substantially same as the original (non-variant) peptide having no such variance, and, the amino acid sequence of such variant peptide is deemed as substantially same as the amino acid sequence of the original (non-variant) peptide.

It is a well-known fact that generally, the change such as substitution, deletion or insertion (addition) of an amino acid in a peptide sequence often does not make a great (notable) change to physiological property or chemical property of such peptide. Such substitution is exemplified by the substitution of a certain amino acid by another amino acid of similar nature (property), and generally, it is considered that if the substitution is made between amino acids having greater similarity in their properties, so much smaller the changes caused by such substitution is in the properties of pre-substituted peptides.

Amino acids are classified, using the similarity of their properties as to one of the criteria, into the following classes, for example: (i) nonpolar (hydrophobic) amino acids (examples: alanine, leucine, isoleucine, valine, proline, phenylalanine, tryptophan, methionine, etc.); (ii) polar (neutral) amino acids (examples: glycine, serine, threonine, cysteine, tyrosine, asparagine, glutamine, etc.); (iii) basic amino acids carrying positive electric charge (examples: arginine, lysine, histidine, etc.); (iv) acidic amino acids carrying negative electric charge (examples: aspartic acid, glutamic acid, etc.), and accordingly, amino acid substitution within each class can be conservative with regard to the property of a peptide (namely, substitution generating "substantially same" amino acid sequences).

In other words, "substantially same amino acid sequences" may include:

(i) amino acid sequences wherein 1 or more, or, in other embodiments, 1 to 3 amino acids were substituted by other amino acids in the amino acid sequences indicated in the above-mentioned formula (I), (II) and SEQ ID NOS:1-71;

(ii) amino acid sequences wherein 1 or more, or, in other embodiments, 1 to 3 amino acids were deleted in the amino acid sequences indicated in the above-mentioned formula (I), (II) and SEQ ID NOS:1-71;

(iii) amino acid sequences wherein 1 or more or, in other embodiments, 1 to 3 amino acids were added (inserted) in the amino acid sequences indicated in the above-mentioned formula (I), (II) and SEQ ID NOS:1-71; or (iv) peptides including modifications to amino acids (particularly, the side chains thereof) among the peptides having the amino acid sequences indicated in above (i), (ii) or (iii), or esters, amides or salts thereof.

A peptide of the present invention, if and when the substitution, deletion, insertion (addition), modification, etc. of above (i) to (iv) is intentionally or incidentally provided in the amino acid sequence thereof, can be varied to a stable peptide against heat or protease or a high-activity peptide having more enhanced inhibitory activity. The peptides of the present invention include also these variant peptides or amides thereof, esters thereof or salts thereof.

Furthermore, among the peptides of the present invention are the peptide consisting of the amino acid sequence indicated in any of the above-mentioned formula (I), (II) and SEQ ID NOS:1-71, and the peptide containing the amino acid sequence sharing the homology of about 50 to 99.9% (preferably, 70 to 99.9%, more preferably 90 to 99.9%) with the foregoing amino acid sequence and having the activities of substantially same nature as the peptide consisting of the amino acid sequence indicated in any of the above-mentioned formula (I), (II) and SEQ ID NOS:1-71, or amides thereof, esters thereof or salts thereof. Such activities include, for example, inhibitory activities of the peptides such as an inhibitory activity on the binding of a ligand to its receptor, a signaling inhibitory activity. The inhibitory activities of "substantially same nature" mean that the properties such as the inhibitory activity on the ligand binding to the receptor are of the same nature. Therefore, it is acceptable even if non-significant effectiveness levels of the inhibitory activity on the ligand binding to the receptor are found, and it does not matter even if there are differences in molecular weights.

The amides, esters or salts of the peptide having the amino acid sequence indicated in any of the above-mentioned SEQ ID NOS:1-71 include the same ones as are exemplified for the peptide indicated in the above-mentioned formula (I). Preferably, the peptide having the amino acid sequence indicated in any of the above-mentioned SEQ ID NOS:1-71 is amidated at the carboxyl group of the C-terminal amino acid residue.

The peptides of the present invention including the peptide containing the amino acid sequence indicated in any of the above-mentioned SEQ ID NOS:1-71 can be produced by conventionally known methods of synthesizing peptides. For the syntheses of peptides, either solid phase peptide synthesis or liquid phase synthesis may be utilized. Namely, an expected peptide can be produced by condensing a partial peptide able to constitute a peptide or an amino acid with remaining portions, and if the product has a protecting group, by eliminating the protecting group. As the known condensation methods and elimination of protecting groups, the following examples (1) to (5) are included:

(1) M. Bodanszky and M. A. Ondetti, Peptide Synthesis, Interscience Publishers, New York (1966).

(2) Schroeder and Luebke, The Peptide, Academic Press, New York (1965).

(3) N. Izumiya, et. al., Peptide Synthesis, Basics and Practice, Maruzen, Tokyo (1975).

(4) H. Yajima and S. Sakakibara, Seikagaku-Jikken-Koza I, Protein Chemistry IV, Tokyo Kagakudojin, Tokyo, pp 205 (1977).

(5) H. Yajima, Zoku-Iyakuhin-no-Kaihatsu, Vol. 14, Peptide Synthesis, Hirokawa Publishing Co., Tokyo (1991).

As practical methods for syntheses of peptides, the following examples can be given:

Generally, commercially available resins for synthesis of polypeptides can be used. Such resins include, for example, chloromethyl resin, hydroxymethyl resin, benzhydroxylamine resin, aminomethyl resin, 4-hydroxybenzylalcohol resin, 4-methylbenzhydroxylamine resin, PAM resin, 4-hydroxymethylmethylphenylacetoamidomethyl resin, polyacrylamide resin, 4-(2',4'-dimetoxyphenyl-hydroxymethyl) phenoxy resin, 4-2',4'-dimetoxyphenyl-Fmoc aminoethylphenoxy resin, etc. Using such resin, an amino acid with suitably protected α-amino group and side chain functional group is condensed on the resin to the sequence of the expected polypeptide in accordance with conventionally known condensation methods. In the last stage of the reaction, the polypeptide is cleared from the resin and simultaneously various protective groups are removed, and then, by carrying out intramolecular disulfide bond-forming reaction in highly diluted solution, the expected polypeptide or amide thereof is obtained. For the above-mentioned condensation of the protected amino acid, various activated reagents usable for the syntheses of polypeptides can be used, but it is particularly better to use carboxyimides. Among such carboxyimides are DCC, N,N'-diisopropylcarbodiimide, N-ethyl-N'-(3-dimethylaminopropyl)cabodiimde, etc. For the activation by these, together with racemization inhibitory additives (for example, HOBt, HOOBt), a protected amino acid is added directly to the resin, or after activating the protected amino acid as symmetric acid anhydride or HOBt ester or HOOBt ester, it can be added to ester resin.

Solvents used for the activation of protected amino acids and the condensation with resins can be chosen from among the solvents known to be usable for polypeptide condensation reactions. For example, acid amides such as N,N-dimethylformamide, N,N-dimethylacetoamide and N-methylpyrrolidone, halogenated hydrocarbons such as methylene chloride and chloroform, alcohols such as trifluoroethanol, sulfoxides such as methyl sulfoxide, ethers such as pyridine, dioxane and tetrahydrofuran, nitriles such as acetonitrile and propionitrile, esters such as methyl acetate and ethyl acetate, or appropriated mixtures of the foregoings are used. A solvent used for activation of a protected amino acid or its condensation with resin can be selected from among the solvents known to be usable for condensing reactions of polypeptides. The reaction temperature is appropriately set within the scope known to be applicable to polypeptide bond forming reactions, usually, at −20° C. to 50° C. Activated amino acid derivatives are usually used at 1.5 to 4 times excess. According to the result of tests adopting ninhydrin reaction, if the condensation is insufficient, the repetition of condensation reactions without eliminating protective groups can lead to sufficient condensation. If sufficient condensation is attained by the repetition of reactions, unreacted amino acids can be acetylated by the use of acetic anhydride or acetylimidazole.

The protective group of the amino group used as ingredients include, for example, Z, Boc, tertialypentyloxycarbony, isobornyloxycarbonyl, 4-methoxybenzyloxycabonyl, Cl—Z, Br—Z, adamantyloxycabonyl, trifluoroacetyl, phtaloyl, formyl, 2-nitrophenylsulphenyl, diphenylphosphinothioyl, Fmoc, etc. Carboxyl group can be protected, for example, by alkyl esterification (e.g. straight-chain, branching or circular alkyl esterification of methyl, ethyl, propyl, butyl, tertialbutyl, cyclopentyl, cyclohexyl, cycloheptyl, cyclooctyl, 2-adamantyl, etc.), aralkyl esterification (e.g. benzylester, 4-nitrobenzylester, 4-methoxybenzylester, 4-chlorbenzylester, benzhydryl esterification), phenacylesterification, benzylcarbonylhydrazidation, tertialybutoxycarbonylhydrazidation, tritylhydrazidation, etc. The hydroxyl group of serine can be protected, for example, by esterification or etherification. The groups suitable for this eterification include, for example, groups derivatized from carboxylic acid such as lower alkanoyl group such as acetyl group, aroyl group such as benzoyl group, benzyloxycarbonyl group, ethoxycarbonyl group. The groups suitable for etherification include, for example, benzyl group, tetrahydropiranyl group, tertiarybutyl group, etc. As the protective groups of phenolic OH group of tyrosine, for example, Bzl, Cl2-Bzl, 2-nitrobenzyl, Br—Z, tertiarlybutyl, etc. are used. As the protective groups of imidazole of histidine, for example, Tos, 4-methoxy-2,3,6-trimethylbenzenesulfonyl, DNP, benzyloxymethyl, Bum, Boc, Trt, Fmoc etc. are used.

Ingredients with activated carboxyl groups include, for example, corresponding acid anhydride, azide, active ester [ester of alcohol (e.g. pentachlorophenol, 2,4,5-trichlorophenol, 2,4-dinitrophenol, cyanomethylalcohol, p-nitrophenol, HONB, N-hydroxysuccimide, N-hydroxyphtalimide, HOBt)] are used. Ingredients with activated amino group include, for example, corresponding phosphoric amide. As the methods to remove (elimiate) protective groups, for example, catalytic reduction in hydrogen airstream in the presence of a catalyst such as Pd-black or Pd-carbon, acid treatment by anhydrous hydrogen fluoride, methanesulfonic acid, trifluoromethanesulfonic acid, trifluoroacetic acid or a mixture thereof, etc, base treatment by diisopropylethylamine, triethylamine, piperidine, piperadine, etc., and reduction by natrium in liquid ammonia are used. Elimination reaction by the above-mentioned acid treatment is done generally at the temperature of about −20° C. to 40° C., but in the acid treatment, it is effective to add a cation trapping agent such as anisole, phenol, thioanisole, m-cresol, p-cresol, dimethylsulfide, 1,4-butanedithiol, 1,2-ethanedithiol. 2,4-dinitrophenyl group used as the protective group of imidazole of histidine is removed by thiophenol treatment. Formyl group used as the protective group of indole of tryptophan is removed by elimination of protection by the above-mentioned acid treatment in the presence of 1,2-ethanedithiol, 1,4-butanedithiol, etc. and also is removed by alkaline treatment by dilute sodium hydroxide solution, dilute ammonia, etc.

Protection and protective group of functional groups not to be involved in the reaction of ingredients, and elimination of such protective group, and activation of functional groups to be involved in the reaction, etc. can be appropriately selected from among conventionally known groups or conventionally known measures. As alternative methods to obtain amides of polypeptides, there is, for example, a method to manufacture, after amidating and protecting α-carboxyl group of carboxyterminal amino acid and then extending the peptide chain to the desired chain length on the side of amino group, a polypeptide eliminating the protective group of α-amino group of N-terminal of such peptide chain and a polypeptide eliminating the protective group of carboxyl group of C-terminal, and then these two peptides are condensed in the above-mentioned mixed solvent. The details of the condensation reaction are the same as described above. After purifying the protected polypeptide obtained by the condensation, the desired raw polypeptide can be obtained by eliminating all the protective groups by the above-mentioned method. Having purified this raw polypeptide using various known purification methods, if the main fraction is freeze-dried, an amide type of the desired polypeptide can be obtained. To get an ester type of the polypeptide, for example, make an amino acid ester by condensing α-carboxyl group of carboxy-terminal amino acid with the desired alcohols, and then, the ester type of the desired polypeptide can be obtained in the same way as the amide type of the polypeptide.

After the reaction, the peptides of the present invention can be purified and isolated by combining usual purification methods such as solvent extraction, distillation, column chromatography, liquid chromatography, re-crystallization, etc. If a peptide obtained by the above-mentioned methods is a salt-free type, it can be converted to a suitable salt by known methods, or if such peptide is a salt, it can be converted to a salt-free type by known methods.

Other CXCR4 Inhibitors

In another embodiment, the CXCR4 inhibitor is an antibody-based moiety directed against the CXCR4 receptor, which antibody-based moiety is capable of acting as a CXCL12 antagonist. Such molecules include, but are not limited to: monoclonal antibodies, polyclonal antibodies, and antibody fragments such as recombinant antibody fragments, single-chain antibodies (scFv), single antibody variable domains, and the like. Single-chain antibodies are small recognition units consisting of the variable regions of the immunoglobulin heavy ($V_H$) and light ($V_L$) chains which are connected by a synthetic linker sequence. Single antibody domain proteins (dAbs) are minimized antibody fragments comprising either an individual $V_L$ domain or an individual $V_H$ domain.

Methods of generating monoclonal and polyclonal antibodies are well known in the art. Antibodies may be generated via any one of several known methods, which may employ induction of in vivo production of antibody molecules, screening of immunoglobulin libraries, or generation of monoclonal antibody molecules by continuous cell lines in culture. These include, but are not limited to, the hybridoma technique, the human B-cell hybridoma technique, and the Epstein-Barr virus (EBV)-hybridoma technique. Antibody fragments may be obtained using methods well known in the art, including, but not limited to by proteolytic hydrolysis of the antibody or by expression in E. Coli or mammalian cells (e.g., Chinese hamster ovary (CHO) cell culture or other protein expression systems) of DNA encoding the fragment. F(ab')$_2$ antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. Other methods of cleaving antibodies, such as separation of heavy chains to form monovalent light-heavy chain fragments, further cleavage of fragments, or other enzymatic, chemical, or genetic techniques may also be used, so long as the fragments retain the ability to bind to the antigen that is recognized by the intact antibody. An Fv is composed of paired heavy chain variable and light chain variable domains. This association may be non-covalent. Alternatively, as described hereinabove, the variable domains may be linked to generate a single-chain Fv by an intermolecular disulfide bond, or alternately such chains may be cross-linked by chemicals such as glutaraldehyde. Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains. In addition, techniques may be utilized to change a "murine" antibody to a "human" antibody, without altering the binding specificity of the antibody.

An antibody "reactive fragment", as used herein, denotes any molecule comprising the antigen-binding reactive fraction of an antibody. An "antibody or active fragment thereof" as used herein includes, but is not limited to, intact immunoglobulin molecules of any isotype and generated by any animal cell line or microorganism, the antigen-binding reactive fraction thereof, including, but not limited to, the Fab fragment, the Fab' fragment, the F(ab')$_2$ fragment, the variable portion of the heavy and/or light chains thereof, Fab miniantibodies (see e.g. WO 93/15210, U.S. patent application Ser. No. 08/256,790, WO 96/13583, U.S. patent application Ser. No. 08/817,788, WO 96/37621, U.S. patent application Ser. No. 08/999,554, the entire contents of which are incorporated herein by reference), dimeric bispecific miniantibodies and chimeric or single-chain antibodies incorporating such reactive fraction, as well as any other type of molecule or cell in which such antibody reactive fraction has been physically inserted, such as a chimeric T-cell receptor. Such molecules may be provided by any known technique, including, but not limited to, enzymatic cleavage, peptide synthesis or recombinant techniques.

Anti CXCR4 Abs capable of inhibiting CXCL12 activity are known in the art. A non-limitative example of treating dermal wounds with the CXCR4 neutralizing Ab 12G5 is presented in the Examples hereinbelow.

In other embodiments, the inhibitor is a polypeptide, a peptide, a small organic molecule and the like, which is able to selectively bind CXCR4 and act as a CXCL12 antagonist. Preparation and use of such inhibitors is within the abilities of those of skill in the art.

Pharmaceutical Compositions and Therapeutic Use

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein, the term "active ingredient" refers to the CXCR4 inhibitor molecule, preferably the T-140 analogs described herein, accountable for the intended biological effect.

Hereinafter, the phrases "physiologically acceptable carrier" and "pharmaceutically acceptable carrier", which may be used interchangeably, refer to a carrier or a diluent that does not cause significant irritation to an organism and does not abrogate the biological activity and properties of the administered compound.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences", Mack Publishing Co., Easton, Pa., which is herein fully incorporated by reference.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

The pharmaceutical compositions of the invention are suitable for administration systemically or in a local manner, for example, via injection of the pharmaceutical composition directly into a tissue region of a patient (e.g. intralesional injection).

For injection, the active ingredients of the pharmaceutical composition may be formulated in aqueous solutions, preferably in physiologically compatible buffers such as Hank's solution, Ringer's solution, or physiological salt buffer.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical compositions of the invention are also useful for topical and intralesional application. As used herein, the term "topical" means pertaining to a particular surface area and the topical agent applied to a certain area of said surface will affect only the area to which it is applied. The present invention provides, in some embodiments, topical compositions comprising CXCR4 inhibitors as active ingredients. In some embodiments, the invention provides compositions consisting essentially of said CXCR4 inhibitors, e.g. the T-140 analogs of the invention.

Topical pharmaceutical compositions may comprise, without limitation, non-washable (water-in-oil) creams or washable (oil-in-water) creams, ointments, lotions, gels, suspensions, aqueous or cosolvent solutions, salves, emulsions, wound dressings, coated bandages or other polymer coverings, sprays, aerosols, liposomes and any other pharmaceutically acceptable carrier suitable for administration of the drug topically. In certain particular embodiments, wound dressing formulations are provided.

As is well known in the art the physico-chemical characteristics of the carrier may be manipulated by addition a variety of excipients, including but not limited to thickeners, gelling agents, wetting agents, flocculating agents, suspending agents and the like. These optional excipients will determine the physical characteristics of the resultant formulations such that the application may be more pleasant or convenient. It will be recognized by the skilled artisan that the excipients selected, should preferably enhance and in any case must not interfere with the storage stability of the formulations.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

For example, a cream formulation may comprise in addition to the active compound: (a) a hydrophobic component; (b) a hydrophilic aqueous component; and (c) at least one emulsifying agent. The hydrophobic component of the cream is exemplified by the group consisting of mineral oil, yellow soft paraffin (Vaseline), white soft paraffin (Vaseline), paraffin (hard paraffin), paraffin oil heavy, hydrous wool fat (hydrous lanolin), wool fat (lanolin), wool alcohol (lanolin alcohol), petrolatum and lanolin alcohols, beeswax, cetyl alcohol, almond oil, arachis oil, castor oil, hydrogenated castor oil wax, cottonseed oil, ethyl oleate, olive oil, sesame oil, and mixtures thereof. The hydrophilic aqueous component of the cream is exemplified by water alone, propylene glycol or alternatively any pharmaceutically acceptable buffer or solution. Emulsifying agents are added to the cream in order to stabilize the cream and to prevent the coalescence of the droplets. The emulsifying agent reduces the surface tension and forms a stable, coherent interfacial film. A suitable emulsifying agent may be exemplified by but not limited to the group consisting of cholesterol, cetostearyl alcohol, wool fat (lanolin), wool alcohol (lanolin alcohol), hydrous wool fat (hydrous lanolin), and mixtures thereof.

A topical suspension, for example, may comprise in addition to the active compound: (a) an aqueous medium; and (b) suspending agents or thickeners. Optionally additional excipients are added. Suitable suspending agent or thickeners may be exemplified by but not limited to the group consisting of cellulose derivatives like methylcellulose, hydroxyethylcellulose and hydroxypropyl cellulose, alginic acid and its derivatives, xanthan gum, guar gum, gum arabic, tragacanth, gelatin, acacia, bentonite, starch, microcrystalline cellulose, povidone and mixture thereof. The aqueous suspensions may optionally contain additional excipients e.g. wetting agents, flocculating agents, thickeners, and the like. Suitable wetting agents are exemplified by but not limited to the group consisting of glycerol polyethylene glycol, polypropylene glycol and mixtures thereof, and surfactants. The concentration of the wetting agents in the suspension should be selected to achieve optimum dispersion of the pharmaceutical powders within the suspension with the lowest feasible concentration of the wetting agent. Suitable flocculating agents are exemplified by but not limited to the group consisting of electrolytes, surfactants, and polymers. The suspending agents, wetting agents and flocculating agents are provided in amounts that are effective to form a stable suspension of the pharmaceutically effective agent.

Topical gel formulation, for example, may comprise in addition to the active compound, at least one gelling agent and an acid compound. Suitable gelling agents may be exemplified by but not limited to the group consisting of hydrophilic polymers, natural and synthetic gums, crosslinked proteins and mixture thereof. The polymers may comprise for example hydroxyethylcellulose, hydroxyethyl methylcellulose, methyl cellulose, hydroxypropylcellulose, hydroxypropyl methylcellulose, carboxymethyl cellulose, and similar derivatives of amylose, dextran, chitosan, pullulan, and other polysaccharides; Crosslinked proteins such as alburnin, gelatin and collagen; acrylic based polymer gels such as Carbopol, Eudragit and hydroxyethyl methacrylate based gel polymers, polyurethane based gels and mixtures thereof.

Topical pharmaceutical compositions of the present invention may additionally be formulated as a solution. Such a solution comprises, in addition to the active compound, at least one co-solvent exemplified but not limited to the group consisting of water, buffered solutions, organic solvents such as ethyl alcohol, isopropyl alcohol, propylene glycol, polyethylene glycol, glycerin, glycoforol, Cremophor, ethyl lactate, methyl lactate, N-methylpyrrolidone, ethoxylated tocopherol and mixtures thereof.

The active ingredients can also be delivered via iontophoresis, e.g., as disclosed in U.S. Pat. No. 4,140,122, 4,383,529, or 4,051,842.

The composition of the invention may be used for transmucosal, e.g. transdermal delivery. The term "transdermal" delivery as used herein refers to the site of delivery of a pharmaceutical agent. Typically, the delivery is intended to the blood circulation. However, the delivery can include intraepidermal or intradermal delivery, i.e., to the epidermis or to the denial layers, respectively, beneath the stratum corneum. For transmucosal administration, penetrants appropriate to the barrier to be permeated are used in the formulation. Such penetrants are generally known in the art.

There are two prevalent types of transdermal patch designs, namely the reservoir type where the drug is contained within a reservoir having a basal surface that is permeable to the drug, and a matrix type, where the drug is dispersed in a polymer layer affixed to the skin. Both types of designs also typically include a backing layer and an inner release liner layer that is removed prior to use. Preparation of such transdermal patches is within the ability of those of skill in the art; see, for example, U.S. Pat. Nos. 5,560,922, 4,559,222, 5,230, 898 and 4,668,232 for examples of patches suitable for transdermal delivery of a therapeutic agent.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

Pharmaceutical compositions suitable for use in the context of the present invention include compositions wherein the active ingredients are contained in an amount effective to achieve the intended purpose. Determination of a therapeutically effective amount is well within the capability of those skilled in the alt, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

For example, a preferred dose of the T-140 analogs of the invention or anti-CXCR4 Abs for human subcutaneous injection for the treatment of a partial-thickness burn is between about 20-10,000 μg per kg per day. A preferred dose for intravenous (i.v.) administration is between about 20-10,000 μg per kg per day. When applied topically, a preferred dose may be between about 1-1,000 μg per ml.

In one aspect, the compositions of the invention are useful for treating skin burns in a subject in need thereof.

In the present context the term "skin" relates to the outermost surface of the body of an animal including a human and embraces intact or almost intact skin as well as an injured skin surface. The term "skin" further includes all external mucous body surfaces such as oral, nasal conjunctival, vaginal and anal. The inhibitors of the invention may be formulated for e.g. intravaginal or intrarectal use, for example, as pessaries, creams or foams. Suppositories for intrarectal administration can be produced by admixing a drug with a suitable nonirritative excipient, such as cocoa butter and polyethylene glycols, and the like that are solid at normal temperature but become liquid at the temperature in the intestine and melt in rectum to release the drug.

In another aspect, the compositions of the invention are useful for promoting wound healing in a subject in need thereof.

In the present context the term "wound" denotes a bodily injury with disruption of the normal integrity of tissue structures. As used herein, the term "treating wounds" further includes prevention or reduction of scarring, inhibiting or preventing fibrosis and promoting epithelialization in a subject in need thereof.

In one embodiment, the wound is a skin injury. Such wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The term "partial thickness wound" refers to wounds that encompass Grades I-III; examples of partial thickness wounds include, but are not limited to, burn wounds, pressure sores, venous stasis ulcers, and diabetic ulcers. The present invention contemplates treating all wound types In one particular embodiment, the wound is a partial thickness dermal wound.

In another aspect, the compositions of the invention may be used for prevention or reduction of scarring in a subject in need thereof.

In one embodiment, the method is useful for preventing or reducing scarring of the skin. In other embodiments, the present invention can also be used therapeutically to control diseases associated with excessive scarring, including, but not limited to cirrhosis of the liver, constrictive pericarditis, Dupuytren's disease of the hand, plantar fibrosis of the foot and various other fibromatoses.

In yet another aspect, the compositions of the invention may be used for inhibiting or preventing fibrosis in a subject in need thereof.

In certain embodiments, the fibrosis includes, but is not limited to, fibrosis in the skin, in the lung, in the liver, in the kidney, of the central nervous system, in bone or bone marrow, in the cardiovascular system, in an endocrine organ or in the gastrointestinal system.

The compositions of the present invention may be used to treat diseases or conditions associated with fibrosis alone or in combination with other established or experimental therapeutic regimens for such disorders.

In another aspect, the invention is directed to the use of a CXCR4 inhibitor for the preparation of a medicament useful for promoting wound healing.

In various embodiments, the CXCR4 inhibitor includes, but is not limited to, proteins, peptides, antibodies or active fragments thereof, nucleic acids, organic molecules and inorganic compounds. In certain particular embodiments, the inhibitor is an antibody or an antibody fragment, e.g. single-chain antibodies (scFvs) and single antibody domain proteins (dAbs). In a preferable embodiment, the inhibitor is a T-140 analog peptide of the invention or a salt thereof.

In one embodiment, the wound is a dermal wound or lesion. In another embodiment, the wound is a skin burn.

In other aspects, the invention is directed to the use of a CXCR4 inhibitor for the preparation of a medicament useful for promoting epithelialization in a subject in need thereof, for prevention or reduction of scarring or for inhibiting and/or preventing fibrosis.

Whilst the above considerations mainly apply to conditions, disorders or diseases of man it will be appreciated that wound healing, scarring and fibrotic disorders can also be problematic in other animals, particularly veterinary or domestic animals (e.g. horses, cattle, dogs, cats etc). For instance abdominal wounds or adhesions are a major reason for having to put down horses (particularly race horses), as are tendon and ligament damage leading to scarring or fibrosis.

The following examples are presented in order to more fully illustrate some embodiments of the invention. They should, in no way be construed, however, as limiting the broad scope of the invention.

EXAMPLES

Materials And Methods

Human Cell Lines

Human skin fibroblasts and keratinocytes were obtained from skin biopsies. Fibroblasts were grown in Dulbecco's Modified Eagle's medium (DMEM) containing 10% fetal calf serum SFCS) and keratinocytes were cultured in H. Green keratinocyte specific medium (Green et al., 1979). Keratinocytes and fibroblasts were kindly provided by Prof. Ben-Bassat's laboratory at Hadassah University Hospital, Jerusalem. Cells were passaged weekly by trypsinization. Bone marrow endothelial cells (BMEC) are microvascular endothelial cells isolated from human bone marrow aspirates. The BMEC-1 cell line was kindly provided by S. Rafii. This cell line was generated by introducing the SV40-large T antigen into an early passage of primary BMEC, and it has retained the morphology, phenotype and function of the primary BMEC. The BMEC-1 cells were cultured in a complete DMEM medium and were passaged weekly by trypsinization.

Immunohistochemistry and In Vitro Scratch Assay

Skin tissue samples were routinely fixed with formalin and embedded in paraffin. Antigen retrieval was performed in EDTA buffer for 15 minutes in microwave, and sections were stained with monoclonal antibody (mAb) against CXCL12 (MAB 350, R&D, 1:100), mAb against cytokeratin (M0630, DAKO) and mAb anti vimentin (M7020, DAKO), mAb against Rat CXCR4 (Torrey Pines Biolabs, Calif.), using biotinalated secondary polymer (87-9963, Zymed) based on a standard indirect avidin-biotin horseradish peroxidase method, according to the manufacturer's instructions. 3-amino-9-ethylcarbazole (AEC) was used for color development and sections were counterstained with Hematoxylin.

In other experiments, keratinocyte and fibroblast monolayers were grown in a tissue culture 6 mm plates. Then cells were scratched using a 200 µl pipette, washed three times with PBS and grown in DMEM medium with 1% FCS. After 2 days, cells were fixed using 4% PFA and stained for the chemokine CXCL12 as previously described.

ELISA Assay and RT-PCR

ELISA assays for CXCL12 and IL-8 in burn fluids of fibroblasts and keratinocytes medium were performed using the Quantikine kit (R&D Systems, Inc Minneapolis Minn. 55413 USA), according to the manufacturer's instructions.

The expression levels of the chemokine CXCL12 and the chemokine receptor CXCR4 were determined by RT-PCR analysis. Total RNA was isolated from primary fibroblasts (Fib.) and keratinocytes (Ker.) cultures or bone marrow endothelial cells (BMEC). Each RNA sample was subjected to cDNA synthesis, and then semi-quantitative PCR was performed with specific primers as presented in Table 2 at appropriate annealing temperatures. The resulting PCR products were separated on 1% agarose gel.

TABLE 2

| PCR primers | | | |
|---|---|---|---|
| | Sense Primer (SEQ ID NO:) | Antisense Primer (SEQ ID NO:) | Product (bp) |
| Chemokine Receptors | | | |
| Human CXCR4 | AGCTGTTGGCTGAAAAGGTGGTCT ATG (72) | GCGCTTCTGGTGGCCCTTGGAGT GTG (73) | 260 |
| Chemokines | | | |
| Human CXCL12α | ATGAACGCCAAGGTCGTGGTCG (74) | TGTTGTTGTTCTTCAGCCG (75) | 202 |
| Human CXCL12β | ATGAACGCCAAGGTCGTGGTCG (76) | CGGGTCAATGCACACTTGTC (77) | 222 |
| Housekeeping gene | | | |
| β-actin | CCCTGGACTTCGAGCAAGAG (78) | TCTCCTTCTGCATCCTGTCG (79) | 298 |

Transwell Migration Assays

Rat peripheral blood cells were loaded on Ficoll-Histopaque gradient (Histopaque-1077-1, Sigma) and the peripheral blood mononuclear cells (PBMC) were isolated. Rat PBMC migration was assessed in 24-well chemotaxis chambers (6.5-mm diameter, 5-µm pore polycarbonate transwell culture insert; Costar, Cambridge, Mass.). 600 µl RPMI 1640 with 1% BSA (migration buffer) with or without 100 ng/ml of CXCL12α (Peprotech) were added to the lower wells, and $2 \times 10^5$ cells suspended in 100 µl of RPMI 1640 with 1% BSA were added to the upper wells. After three hours of incubation, the membrane was removed and migrating cells were counted for 1 min using fluorescence activated cell sorting (FACS).

Tissue Collection, Histological Evaluation of the Burn Lesion.

Human skin tissue samples were obtained from the Plastic Surgery Department, Souraski Medical Center, Tel-Aviv.

In order to examine the different phases in burn wound healing and the involvement of the chemokine CXCL12 and the receptor CXCR4, the following experiments were done. Wistar female rats were anesthetized and their back was shaved. 1 cm² burns were inflicted with a metal rod that has been immersed in a hot boiling water bath and laid on the posterior part of the hip and back for 2-3 seconds. All experiments were approved by the Animal care committee of the Medical Center, Tel-Aviv and the Hebrew University. Heterozygous mice bearing a GFP reporter knocked-in allele to the CX3CR1 locus (Qu et al. 2004) were maintained at the Weizmann Institute of Science Animal Facility, and burns were inflicted as described above. Each group of 3 animals was injected subcutaneously to the burned area with PBS. Animals were sacrificed at the indicated times after burn infliction: 0, 6 hr, 1 day, 3 days, 5 days and 7 days. Histopathological diagnosis was confirmed for each specimen. Histological sections were prepared from formalin-fixed, paraffin-embedded tissues stained with Hematoxylin and Eosin. Evaluation to the level of epithelialization and white blood cells (WBC) in the epidermis and dermis was made to each section by a scale from 1-5. The sections were scored by two independent pathologists.

In other experiments, treated rats were injected subcutaneously to the burned area with one of the following: PBS, mAb against Rat CXCR4 (12G5 clone, R&D Systems Inc., Minneapolis, Minn.), or the small peptide CXCR4 inhibitor 4F-benzoyl-TN14003 (4F-benzoyl-Aig-Arg-Nal-Cys-Tyr-Cit-Lys-DLys-Pro-Tyr-Arg-Cit-Cys-Arg-NH$_2$, SEQ ID NO:52; Tamamura et al., 2003). All animals were sacrificed 120 hr after injury. Histopathological diagnosis was confirmed for each specimen. Histological sections were prepared from formalin-fixed, paraffin-embedded tissues stained with Hematoxylin and Eosin. Evaluation to the level of epithelialization and white blood cells (WBC) in the dermis was made to each section by a scale from 1-5. The grading scale was as follows: 0=No inflammation or epithelialization; 1=Low inflammation or epithelialization; 2=Low to moderate inflammation or epithelialization; 3 Moderate inflammation or epithelialization; 4=High inflammation or epithelialization; 5=Very high inflammation or epithelialization. Each section was evaluated by two independent pathologists.

Swine burned skin paraffin embedded sections were provided by the Laboratory of Experimental Surgery, Hadassah university hospital, Jerusalem. All experiments were approved by the animal care committee of the Hebrew University. Burn blister fluid collection was collected at the Plastic Surgery Department, Souraski Medical Center, Tel-Aviv as a medical procedure. The blister fluid was examined for CXCL12 and IL-8 levels by ELISA assay.

Statistical Analysis

Results are expressed as mean±SD. Statistical differences were determined by an analysis of two-tailed Student's test.

Manufacturing of 4F-benzoyl-TN14003

1. Synthesis of 4F-benzoyl-TN14003 protected polypeptide resin:

After removing Fmoc group from Fmoc-Rink amide resin (0.34 mmol/g) 2.94 g (1 mmol) by 20% piperidine/DMF, Fmoc-Arg(Pbf)-OH (2.5 eq) corresponding to the 14-position was added, and condensation reaction by DIPCDI-HOBt method was conducted in DMF. The progress of the condensation reaction was monitored by ninhydrin test of Kaiser, E. et al. (Anal. Biochem. 34: 595 (1970)).

2. Introduction of Amino Acids of the 13-Position to 1 Position:

Similarly to the foregoing, Cys(Trt), Cit, Arg(Pbf), Tyr(t-Bu), Pro, DLys(Boc), Lys(Boc), Cit, Tyr(t-Bu), Cys(Trt), Nal, Arg(Pbf), Arg(Pbf) residue was sequentially introduced into Rink amide resin, 4-fluorobenzoic acid (2.5 eq) was condensed at the last N-terminal by DIPCDI-HOBt method and the protected polypeptide resin was obtained.

3. Deprotection and Clearage of Polypeptide from Resin and Purification:

The protected polypeptide resin(1 mmol) was treated by 270 mL of 1 M TMSBr-thioanisole/TFA(trifluoroacetic acid) mixture (in the presence of m-cresol (100 eq), ethanedithiol (300 eq)) at 25° C. for 3 hours. The resin was separated by filtration from the reaction mixture, washed with TFA 5 mL twice, the mixture of the filtrate and the wash solution was subjected to concentration in vacuo. The remaining residue was added with 300 mL of water-cooled dry ether, the resultant sediment was separated from supernatant liquid by centrifugal sedimentation and decantation. The obtained residue was cleansed by cold ether, dissolved into 500 mL of 1 N acetic acid, and diluted to 2.5 L by distilled water.

4. Cyclization by Air Oxidation:

Diluted water solution of the above-mentioned polypeptide was adjusted to pH 7.5 by concentrated ammonia water, and was cyclized by ventilated air oxidation. This water solution was purified by preparative HPLC (COSMOSIL 5C8 AR-II column: acetonitrile water) and gel filtration chromatography (Sephadex G-15, eluate: 0.1 N AcOH), a polypeptide of a single peak was obtained and freeze-dried. The purity was confirmed by HPLC.

Example 1

CXCL12 is Similarly Expressed in Human, Swine, and Rat Normal Skin

Figure 1A:
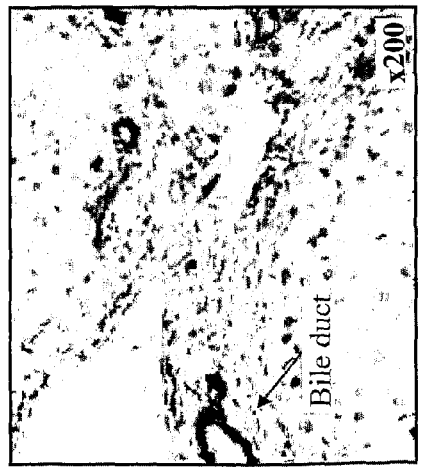
FIG. 1: Immunohistochemical staining of mouse (A), human (B), and rat (C) liver sections for CXCL12. Immunohistochemical staining was performed using a monoclonal antibody against the chemokine CXCL12. Control staining is shown in D, E and F, respectively. The black arrows indicate bile duct epithelial cells that were positively stained for the chemokine. (Original magnification ×200).
Figure 1B:
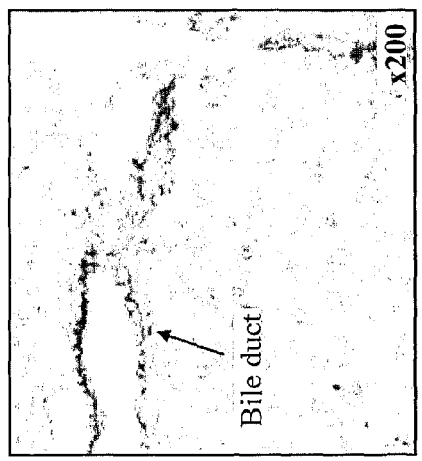
Figure 1C:
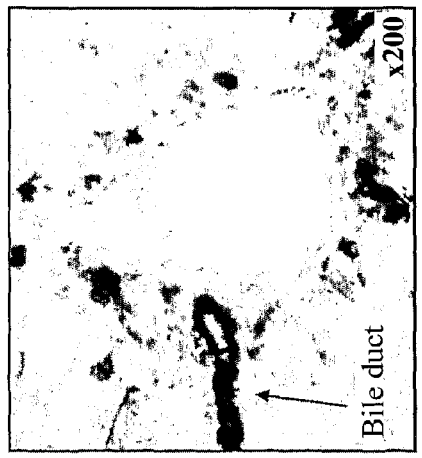
Figure 1D:
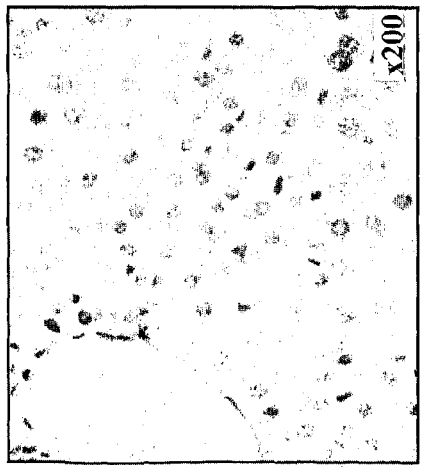
Figure 1E:
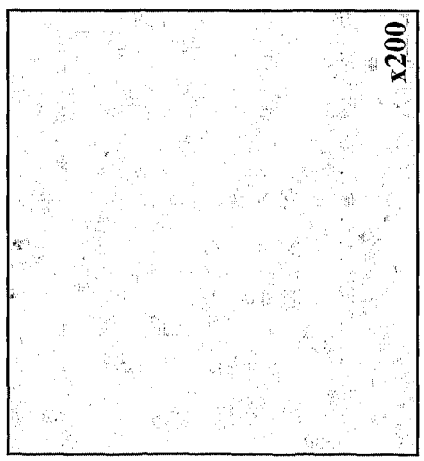
Figure 1F:
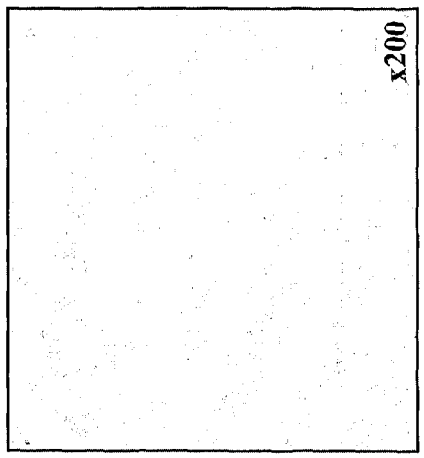
Figure 2A:
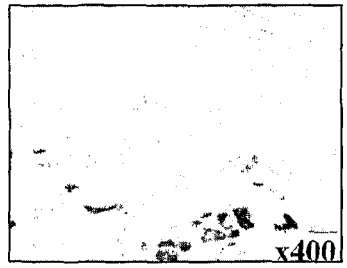
FIG. 2: Expression of CXCL12 in normal human skin. Immunohistochemistry staining results using a monoclonal antibody against the chemokine CXCL12 on human normal skin section. A—Stained cells in the basal layer of the epidermis. B—Scattered cells stained in the papillary dermis. C—Endothelial cells and pericytes stained in blood vessel. D—Fibrous sheet stained in the hair follicle. E—Sweat glands stained not uniformly. F—Axons and blood vessels stained in nerve tissue. G-I Control staining. Sections were stained without the primary antibody ensuring that no background staining is received from the second antibody. G—Epidermis and papillary dermis, H—blood vessel, I—Sweat glands. J-L Control staining. Sections were stained with the primary antibody after incubation with both of the ligands, CXCL12 α and CXCL12β. J—Epidermis and papillary dermis, K—Blood vessel, L—Hair follicle. (Original magnification ×400).
Figure 2B:
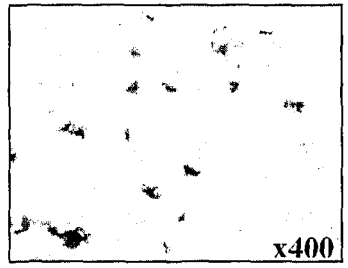
Figure 2C:
Figure 2D:
Figure 2E:
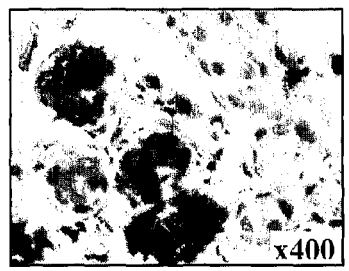
Figure 2F:
Figure 2G:
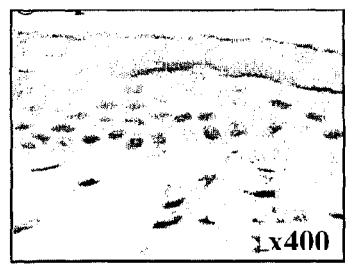
Figure 2H:
Figure 2I:
Figure 2J:
Figure 2K:
Figure 2L:
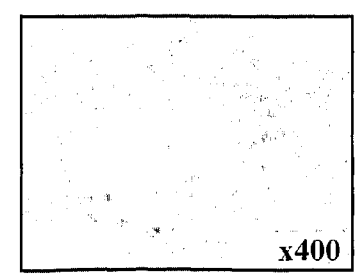
Figure 3A:
FIG. 3: Expression of CXCL12 in normal rat and swine skin.
Figure 3B:
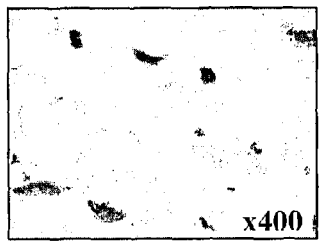
Figure 3C:
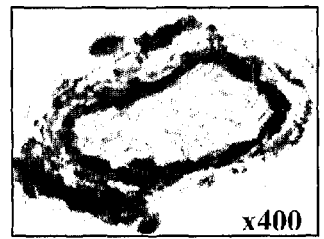
Figure 3D:
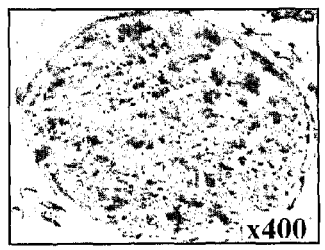
Figure 3E:
Figure 3F:
Figure 3G:
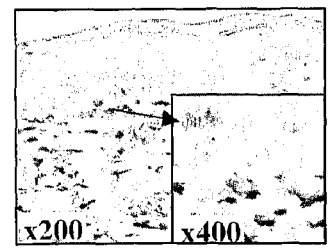
Figure 3H:
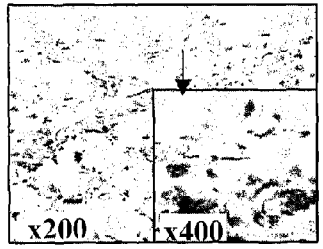
Figure 3I:
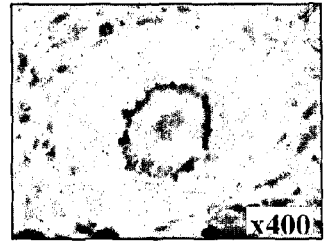
Figure 3J:
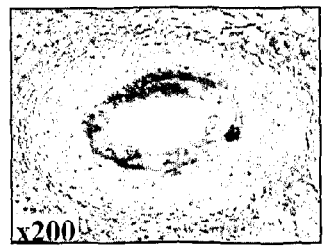
Figure 3K:
Figure 3L:

The expression of CXCL12 in normal skin was examined by immunohistochemical staining using anti-CXCL12 mAb (mAb350). The inventors first examined the antibody cross reactivity of CXCL12 staining on liver sections of mouse, human, and rat since previous studies have shown that CXCL12 is specifically expressed in the bile ducts and blood vessels of human liver (Wald et al., 2004). Mouse, human, and rat liver bile ducts were specifically stained with monoclonal antibody mAb350 for CXCL12 (FIGS. 1A, 1B and 1C, respectively). A negative control stain performed without the primary Ab showed no staining (FIG. 1D-1F). Using the same monoclonal antibody staining for CXCL12 in human, swine and rat normal skin showed similar expression patterns. CXCL12 in human normal skin (FIG. 2) was detected in the basal layer of the epidermis (FIG. 2A), on scattered cells in the papillary dermis (FIG. 2B), in pericytes and in the endothelial layer of blood vessels (FIG. 2C). The fibrous sheet of hair follicles (FIG. 2D), sweat glands (not uniformly) (FIG. 2E), axons and small blood vessels in the nerve tissue (FIG. 2F) also expressed CXCL12. No staining was detected with a control antibody used to stain identical skin sections (FIG. 2G-L). CXCL12 was detected in rat normal skin on the basal layer of the epidermis (FIG. 3A), on scattered cells in the papillary dermis (FIG. 3B), and on pericytes and the endothelial layer of blood vessels (FIG. 3C). The chemokine CXCL12 was also expressed by axons and small blood vessels in the nerve tissue (FIG. 3D) and by fibrous sheet of hair follicles (FIG. 3E). No staining was detected with control antibody used to stain the same skin sections (FIG. 3F). The chemokine CXCL12 was similarly expressed by swine normal skin cells in the basal layer of the epidermis (FIG. 3G), by scattered cells in the papillary dermis (3H), in pericytes and by the endothelial layer of blood vessels (3I). The chemokine CXCL12 was also expressed by fibrous sheets of hair follicles (FIG. 3J) and by sweat glands (FIG. 3K). No staining was detected with control antibody used to stain the same skin sections (FIG. 3L). Overall, CXCL12 is similarly expressed in human, swine, and rat skin by dendritic cells, pericyte and endothelial cells, fibrous sheet, fibroblasts, and axons in the dermis, whereas keratinocytes from all species were not stained. This unique and conserved expression pattern suggests a role for CXCR4/CXCL12 axis in the organization of skin tissue.

Example 2

Figure 4A:
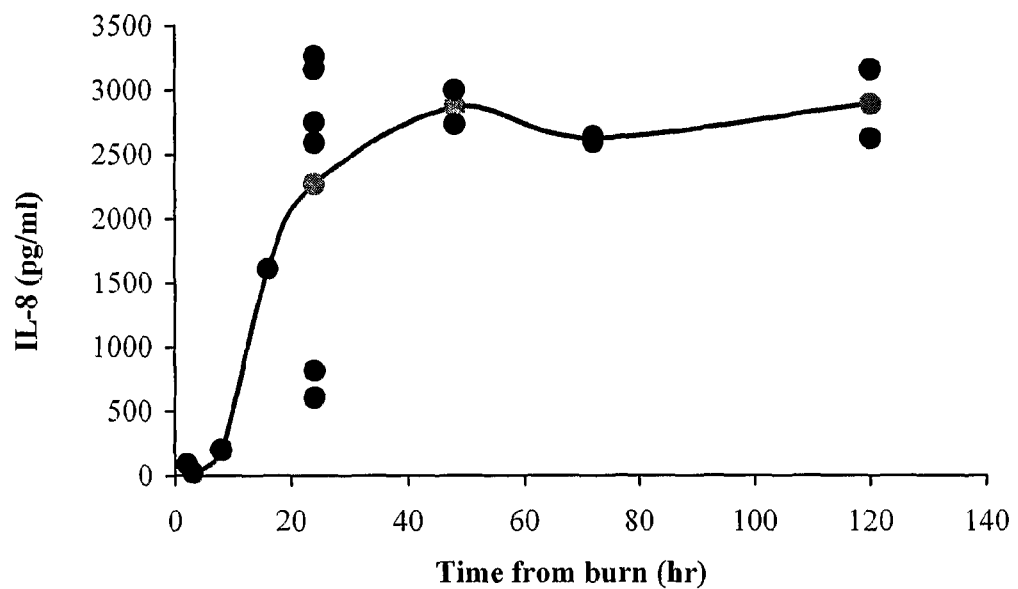
Figure 4B:
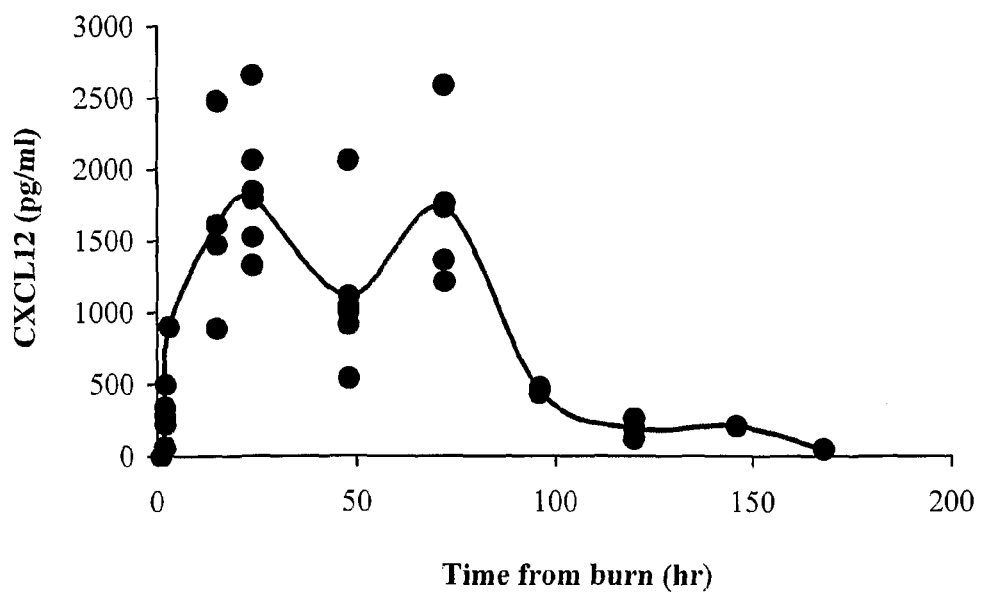

Following Burns, the Level of CXCL12 was Markedly Increased in Human Burn Blister Fluids, Hair Follicles, Blood Vessels Endothelium and Fibroblasts in the Recovering Dermis of Rat, Swine and Human Skin In order to study the effect of burn injury on CXCL12 expression in the skin, the inventors first collected burn wound fluids and CXCL12 levels were measured by ELISA assay and compared to the levels of IL-8 (FIG. 4A, 4B). The results indicate a unique pattern of the chemokine CXCL12 expression compared to IL-8. IL-8 appeared first in the burn fluid a few hours after injury, reached a plateau level after 1 day and remained at the same level for the next 4 days. CXCL12, however, appeared a few hours after injury, reached a plateau level after 1 day, and remained at the same level for an additional 2 days; then the level of CXCL12 decreased exponentially. The consistent overexpression of IL-8 in burn wound fluids and skin tissue has been also reported by others (Iocono et al., 2000). These authors suggested that IL-8 has a role in stimulating neutrophil migration and accelerating the angiogenic process within the burn wound.

The expression of the chemokine CXCL12 following burn infliction was further examined by immunohistochemical staining of rat skin sections. The results shown in FIG. 5A-5B indicate accumulation of CXCL12 in the rat burned skin in correlation with time. Six hours and one day after injury, CXCL12 was not detected in the burned tissue. Three days post burn, CXCL12 was detected in endothelium blood vessels, in the hair follicles and also in scattered cells accumulated in the dermis. Five days and seven days post burn, a higher expression of the chemokine was detected in blood vessels and in fibroblast-like cells accumulated in the dermis. As was shown before for human normal skin (Example 1), CXCR4 was detected in normal and proliferating rat epithelial cells and endothelial cells after burn injury. In the dermis of injured skin CXCR4 expression was also detected in mononuclear cells as well as infiltrating eosinophils.

Figure 5C:
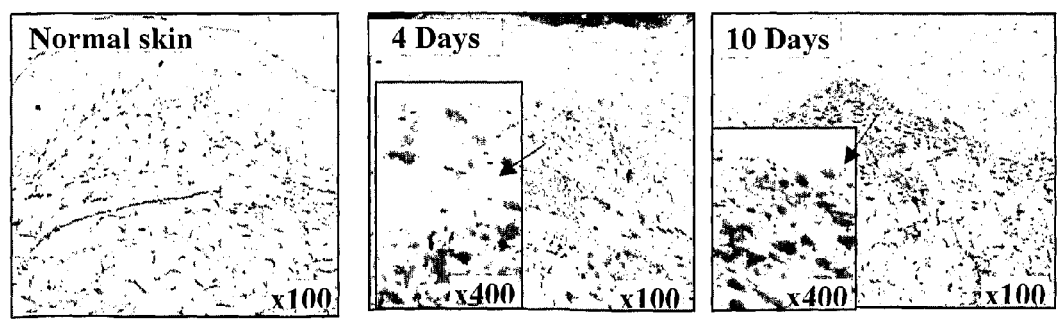

The pattern of CXCL12 expression in swine skin following a burn injury is similar. Four days post burn, CXCL12 was present in endothelium blood vessels and in scattered cells that accumulated in the papillary dermis. Ten days after injury, a strong expression of the chemokine was detected in blood vessels and in the accumulating fibroblast-like cell population in the papillary dermis normal skin stained for CXCL12, as is shown in FIG. 5C.

Figure 6A:
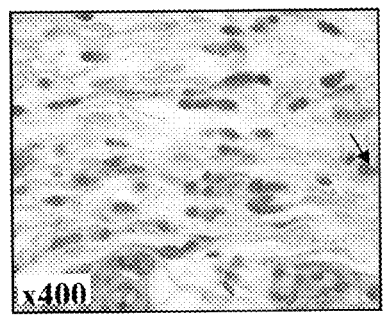
Figure 6B:
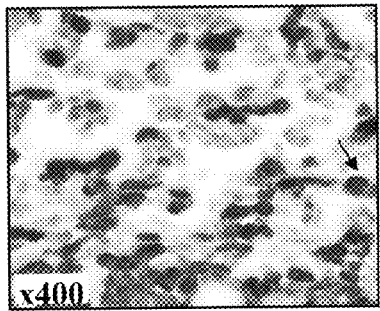
Figure 6C:
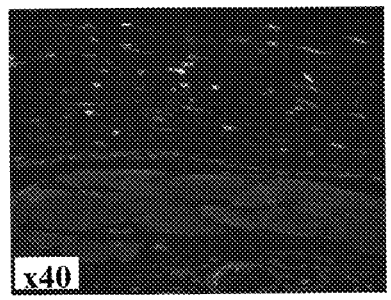
Figure 6D:
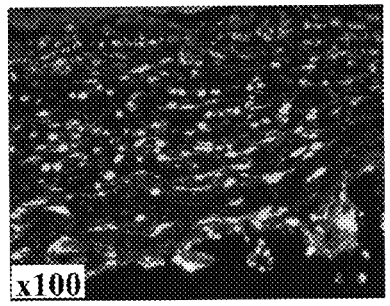
Figure 6E:
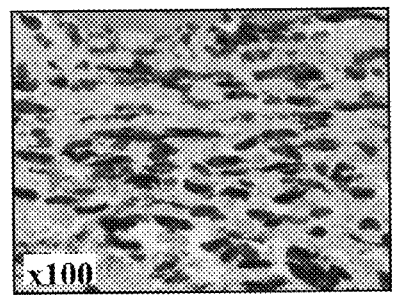
Figure 6F:
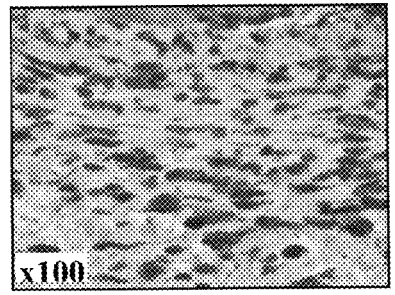
Figure 6G:
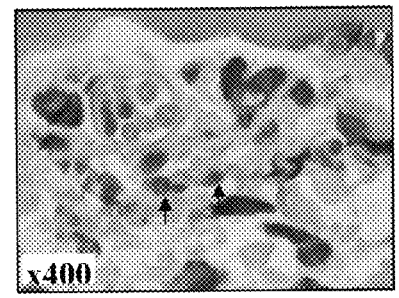
Figure 6H:
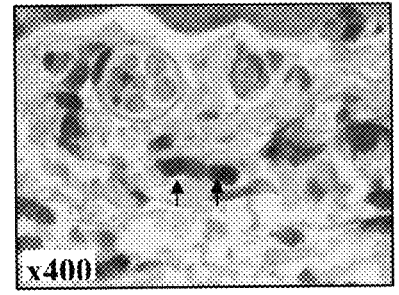

In order to identify the cells that expressed high levels of CXCL12, parallel sections from skin having burn injuries were stained for Vimentin and CXCL12. The majority of fibroblast-like cells were stained for both CXCL12 and Vimentin indicating that fibroblasts were the main cell type that expressed CXCL12 in the skin following burn injury (FIG. 6A, 6B). However, part of the cells that expressed CXCL12 did not express Vimentin. CXCL12 was shown to be expressed by human dendritic cells (DC) localized to the epidermis and the dermis. An excellent means to track monocyte subsets in the skin was through the use of mice bearing a GFP reporter knocked-in to the CX3CR1 chemokine receptor locus (Qu et al. 2004). The present inventors found that following injury, monocytes with a dendritic-like shape accumulated in the dermis and epidermis (FIG. 6C, 6D). Part of the monocyte/dendritic cells that expressed the GFP also expressed CXCL12 (FIG. 6E-H).

To further study the expression of CXCL12 and CXCR4 in the skin, primary skin fibroblasts and keratinocytes cultures were used. In agreement with the in vivo results presented herein, the inventors found that while the fibroblasts expressed the chemokine CXCL12 at the mRNA level, the keratinocytes did not. In contrast to CXCL12, keratinocytes, but not the fibroblasts, expressed the receptor CXCR4 (FIG. 7A). In order to verify these finding, an ELISA assay was used to check the production of CXCL12 by keratinocytes and fibroblasts. The results demonstrated that while keratinocytes did not express the chemokine CXCL12 at the protein level, fibroblasts did express and secrete CXCL12 (FIG. 7B) especially during the recovery of skin fibroblasts migrating into the wound area and accumulating in the dermis. In order to study the effect of wounding on CXCL12 expression by skin fibroblasts, a "scratching" assay was performed on confluent layers of human skin fibroblasts in vitro. Immunohistochemical staining of confluent human skin fibroblasts showed moderate CXCL12 expression. Two days following scratching, an increase in CXCL12 expression by cells adjacent to the affected area was detected. (FIG. 7D, 7E) Fibroblast monolayers were negatively stained with control antibody against cytokeratin (FIG. 7C).

Example 3

Inhibition of the CXCL12/CXCR4 Pathway Resulted in Reduced Eosinophil Accumulation and Improved Epithelialization In order to evaluate the effect of the CXCR4 antagonist 4F-benzoyl-TN14003 and neutralizing antibodies to the receptor on the recovery of rat skin, the inventors first tested their ability to inhibit the migration of rat lymphocytes in response to CXCL12. Migration assay was carried out on total rat lymphocytes separated by Ficoll gradient and their migrating ability to medium containing CXCL12 was examined. Lymphocytes were incubated with the CXCR4 antagonist 4F-benzoyl-TN14003, or an antibody against CXCR4 (10 µg/ml). Treatment of cells with 4F-benzoyl-TN14003 exerted a strong inhibitory effect, whereas treatment of cells with neutralizing antibodies to CXCR4 exerted moderate effect on the migration of cells in response to CXCL12 (FIG. 8).

Next, the inhibitory effect of CXCR4 antagonists on burn wound healing was examined (FIG. 9). Inhibitors were injected subcutaneously to the burned area at 0, 1 day, and 3 days (20 μg per injection), and animals were sacrificed 5 days post burn. Animals injected with the CXCR4 inhibitor 4F-benzoyl-TN14003 showed an increased epithelialization (FIG. 9). A small but not significant decrease in the PMN population in the dermis was observed (FIG. 10). However, a strong and significant inhibition in eosinophil accumulation in the dermis was found in the 4F-benzoyl-TN14003 and antibodies to CXCR4 treated groups (FIG. 11). In contrast to eosinophil accumulation, the accumulation of PMN cell population in the epidermis was not affected (FIG. 11). These results demonstrate a role for CXCR4/CXCL12 interaction in the migration of eosinophils to the skin in the process of epithelialization following burn infliction.

REFERENCES

1. Aiuti et al., J Exp Med 185: 111-120, 1997.
2. Nagasawa et al., Nature 382, 635-638, 1996.
3. Zou et al., Nature 393: 595-599, 1998.
4. Peled et al., Science 283, 845-848, 1999.
5. Askari et al., Lancet 362: 697-703, 2003.
6. Ceradini et al., Nat Med 10: 858-864, 2004.
7. Ponomaryov et al., J Clin Invest 106, 1331-1339, 2000.
8. Hitchon et al., Arthritis Rheum 46: 2587-2597, 2002.
9. Schioppa et al., J Exp Med 198: 1391-1402, 2003.
10. Staller et al., Nature 425: 307-311, 2003.
11. et al., An J Pathol 155: 1577-1586, 1999.
12. H. Tamamura et al. Org. Biomol. Chem 1, 3663, 2003.
13. M. Bodanszky and M. A. Ondetti, Peptide Synthesis, Interscience Publishers, New York, 1966.
14. Schroeder and Luebke, The Peptide, Academic Press, New York, 1965.
15. N. Izumiya, et. al., Peptide Synthesis, Basics and Practice, Maruzen, Tokyo, 1975.
16. H. Yajima and S. Sakakibara, Seikagaku-Jikken-Koza I, Protein Chemistry IV, Tokyo Kagakudojin, Tokyo, pp 205, 1977.
17. H. Yajima, Zoku-Iyakuhin-no-Kaihatsu, Vol. 14, Peptide Synthesis, Hirokawa Publishing Co., Tokyo, 1991.
18. Remington's Pharmaceutical Sciences, Mack Publishing Co., Easton, Pa.
19. Green et al., Proc Natl Acad Sci USA 76: 5665-5668, 1979.
20. Wald et al., Eur J Immunol 34: 1174-1164, 2004.
21. Iocono et al., Wound Repair Regen 8, 216-225, 2000.
22. Lack et al., Clin Pharmacol Ther. 77(5):427-36, 2005.
23. H. Tamamura et. al., Biochemical and Biophysical Research Commun., 253, 877-882, 1998.
24. Qu et al., J Exp Med. 200, 1231-1241, 2004.

SEQUENCE LISTING

```
<160> NUMBER OF SEQ ID NOS: 94

<210> SEQ ID NO 1
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATION
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 1

Arg Arg Xaa Cys Tyr Xaa Lys Xaa Pro Tyr Arg Xaa Cys Arg
1               5                   10

<210> SEQ ID NO 2
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
```

```
<222> LOCATION: (1)..(1)
<223> OTHER INFORMATION: N' ACETYLATION
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-citrulline
<220> FEATURE:
<221> NAME/KEY: MISC_FEATURE
<222> LOCATION: (12)..(12)
<223> OTHER INFORMATION: citrulline

<400> SEQUENCE: 2

Arg Arg Xaa Cys Tyr Arg Lys Xaa Pro Tyr Arg Xaa Cys Arg
1               5                   10

<210> SEQ ID NO 3
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-citrulline
<220> FEATURE:
<221> NAME/KEY: MISC_FEATURE
<222> LOCATION: (12)..(12)
<223> OTHER INFORMATION: citrulline

<400> SEQUENCE: 3

Arg Arg Xaa Cys Tyr Xaa Lys Xaa Pro Tyr Arg Xaa Cys Arg
1               5                   10

<210> SEQ ID NO 4
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-lysine
<220> FEATURE:
```

```
<221> NAME/KEY: MISC_FEATURE
<222> LOCATION: (11)..(12)
<223> OTHER INFORMATION: citrulline

<400> SEQUENCE: 4

Arg Arg Xaa Cys Tyr Xaa Lys Xaa Pro Tyr Xaa Xaa Cys Arg
1               5                   10

<210> SEQ ID NO 5
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' acetylated citrulline
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 5

Xaa Arg Xaa Cys Tyr Xaa Lys Xaa Pro Tyr Arg Xaa Cys Arg
1               5                   10

<210> SEQ ID NO 6
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' acetylated citrulline
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-citrulline
<220> FEATURE:
<221> NAME/KEY: MISC_FEATURE
<222> LOCATION: (12)..(12)
<223> OTHER INFORMATION: citrulline

<400> SEQUENCE: 6

Xaa Arg Xaa Cys Tyr Arg Lys Xaa Pro Tyr Arg Xaa Cys Arg
1               5                   10

<210> SEQ ID NO 7
<211> LENGTH: 14
<212> TYPE: PRT
<213> ORGANISM: Artificial
<220> FEATURE:
```

```
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED
<220> FEATURE:
<221> NAME/KEY: MISC_FEATURE
<222> LOCATION: (3)..(3)
<223> OTHER INFORMATION: N' ACETYLATED
<220> FEATURE:
<221> NAME/KEY: MISC_FEATURE
<222> LOCATION: (8)..(8)
<223> OTHER INFORMATION: D-citrulline
<220> FEATURE:
<221> NAME/KEY: MISC_FEATURE
<222> LOCATION: (11)..(12)
<223> OTHER INFORMATION: citrulline

<400> SEQUENCE: 7

Arg Arg Xaa Cys Tyr Arg Lys Xaa Pro Tyr Xaa Xaa Cys Arg
1               5                   10

<210> SEQ ID NO 8
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED citrulline
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (11)..(12)
<223> OTHER INFORMATION: citrulline

<400> SEQUENCE: 8

Xaa Arg Xaa Cys Tyr Arg Lys Xaa Pro Tyr Xaa Xaa Cys Arg
1               5                   10

<210> SEQ ID NO 9
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-citrulline
<220> FEATURE:
```

```
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: C' AMIDATED

<400> SEQUENCE: 9

Arg Arg Xaa Cys Tyr Xaa Lys Xaa Pro Tyr Arg Xaa Cys Arg
1               5                   10

<210> SEQ ID NO 10
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (11)..(12)
<223> OTHER INFORMATION: citrulline
<220> FEATURE:
<221> NAME/KEY: MISC_FEATURE
<222> LOCATION: (14)..(14)
<223> OTHER INFORMATION: C' AMIDATED

<400> SEQUENCE: 10

Arg Arg Xaa Cys Tyr Xaa Lys Xaa Pro Tyr Xaa Xaa Cys Arg
1               5                   10

<210> SEQ ID NO 11
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED citrulline
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline
```

-continued

```
<220> FEATURE:
<221> NAME/KEY: MISC_FEATURE
<222> LOCATION: (14)..(14)
<223> OTHER INFORMATION: AMIDATED

<400> SEQUENCE: 11

Xaa Arg Xaa Cys Tyr Xaa Lys Xaa Pro Tyr Arg Xaa Cys Arg
1               5                   10

<210> SEQ ID NO 12
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED citrulline
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-citrulline
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: C' AMIDATED

<400> SEQUENCE: 12

Xaa Arg Xaa Cys Tyr Arg Lys Xaa Pro Tyr Arg Xaa Cys Arg
1               5                   10

<210> SEQ ID NO 13
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-citrulline
<220> FEATURE:
<221> NAME/KEY: MISC_FEATURE
<222> LOCATION: (11)..(12)
<223> OTHER INFORMATION: citrulline
<220> FEATURE:
<221> NAME/KEY: MISC_FEATURE
<222> LOCATION: (14)..(14)
<223> OTHER INFORMATION: C' AMIDATED

<400> SEQUENCE: 13

Arg Arg Xaa Cys Tyr Arg Lys Xaa Pro Tyr Xaa Xaa Cys Arg
1               5                   10
```

-continued

```
<210> SEQ ID NO 14
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED citrulline
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (11)..(12)
<223> OTHER INFORMATION: citrulline
<220> FEATURE:
<221> NAME/KEY: MISC_FEATURE
<222> LOCATION: (14)..(14)
<223> OTHER INFORMATION: C' AMIDATED

<400> SEQUENCE: 14

Xaa Arg Xaa Cys Tyr Arg Lys Xaa Pro Tyr Xaa Xaa Cys Arg
1               5                   10

<210> SEQ ID NO 15
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: D-glutamic acid
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 15

Xaa Arg Xaa Cys Tyr Arg Lys Xaa Pro Tyr Arg Xaa Cys Arg
1               5                   10

<210> SEQ ID NO 16
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
```

```
<221> NAME/KEY: MISC_FEATURE
<222> LOCATION: (12)..(12)
<223> OTHER INFORMATION: citrulline

<400> SEQUENCE: 16

Arg Glu Xaa Cys Tyr Arg Lys Xaa Pro Tyr Arg Xaa Cys Arg
1               5                   10

<210> SEQ ID NO 17
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 17

Arg Arg Xaa Cys Tyr Glu Lys Xaa Pro Tyr Arg Xaa Cys Arg
1               5                   10

<210> SEQ ID NO 18
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 18

Arg Arg Xaa Cys Tyr Arg Glu Xaa Pro Tyr Arg Xaa Cys Arg
1               5                   10

<210> SEQ ID NO 19
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
```

```
<222> LOCATION: (12)..(12)
<223> OTHER INFORMATION: citrulline

<400> SEQUENCE: 19

Arg Arg Xaa Cys Tyr Arg Lys Xaa Pro Tyr Arg Xaa Cys Arg
1               5                   10

<210> SEQ ID NO 20
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 20

Arg Arg Xaa Cys Tyr Arg Lys Xaa Pro Tyr Glu Xaa Cys Arg
1               5                   10

<210> SEQ ID NO 21
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 21

Arg Arg Xaa Cys Tyr Arg Lys Xaa Pro Tyr Arg Xaa Cys Glu
1               5                   10

<210> SEQ ID NO 22
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
```

```
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: C' amidated

<400> SEQUENCE: 22

Arg Arg Xaa Cys Tyr Xaa Lys Xaa Pro Tyr Arg Xaa Cys Arg
1               5                   10

<210> SEQ ID NO 23
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: D-glutamic acid
<220> FEATURE:
<221> NAME/KEY: MISC_FEATURE
<222> LOCATION: (8)..(8)
<223> OTHER INFORMATION: D-citrulline
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: c' amidated

<400> SEQUENCE: 23

Arg Arg Xaa Cys Tyr Xaa Lys Xaa Pro Tyr Arg Xaa Cys Arg
1               5                   10

<210> SEQ ID NO 24
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: D-glutamic acid
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: c' amidated

<400> SEQUENCE: 24
```

```
Arg Arg Xaa Cys Tyr Xaa Lys Xaa Pro Tyr Arg Xaa Cys Arg
1               5                   10
```

<210> SEQ ID NO 25
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: D-glutamic acid
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: c' amidated

<400> SEQUENCE: 25

```
Xaa Arg Xaa Cys Tyr Xaa Lys Xaa Pro Tyr Arg Xaa Cys Arg
1               5                   10
```

<210> SEQ ID NO 26
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (10)..(10)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: c' amidated

<400> SEQUENCE: 26

```
Arg Arg Xaa Cys Tyr Xaa Lys Xaa Pro Xaa Arg Xaa Cys Arg
1               5                   10
```

```
<210> SEQ ID NO 27
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: D-glutamic acid
<220> FEATURE:
<221> NAME/KEY: MISC_FEATURE
<222> LOCATION: (14)..(14)
<223> OTHER INFORMATION: c' amidated

<400> SEQUENCE: 27

Arg Arg Xaa Cys Tyr Xaa Lys Xaa Pro Tyr Arg Xaa Cys Arg
1               5                   10

<210> SEQ ID NO 28
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED D-glutamic acid
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: c' amidated

<400> SEQUENCE: 28

Xaa Arg Xaa Cys Tyr Xaa Lys Xaa Pro Tyr Arg Xaa Cys Arg
1               5                   10

<210> SEQ ID NO 29
<211> LENGTH: 14
<212> TYPE: PRT
<213> ORGANISM: Artificial
<220> FEATURE:
```

-continued

```
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (10)..(10)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: c' amidated

<400> SEQUENCE: 29

Arg Arg Xaa Cys Tyr Xaa Lys Xaa Pro Xaa Arg Xaa Cys Arg
1               5                   10

<210> SEQ ID NO 30
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: D-glutamic acid
<220> FEATURE:
<221> NAME/KEY: MISC_FEATURE
<222> LOCATION: (14)..(14)
<223> OTHER INFORMATION: c' amidated

<400> SEQUENCE: 30

Arg Arg Xaa Cys Tyr Xaa Lys Xaa Pro Tyr Arg Xaa Cys Arg
1               5                   10

<210> SEQ ID NO 31
<211> LENGTH: 14
<212> TYPE: PRT
<213> ORGANISM: Artificial
```

```
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: c' amidated

<400> SEQUENCE: 31

Arg Arg Xaa Cys Tyr Xaa Lys Xaa Pro Tyr Arg Xaa Cys Arg
1               5                   10

<210> SEQ ID NO 32
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Guanyl-arginine
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: c' amidated

<400> SEQUENCE: 32

Xaa Arg Xaa Cys Tyr Xaa Lys Xaa Pro Tyr Arg Xaa Cys Arg
1               5                   10

<210> SEQ ID NO 33
<211> LENGTH: 14
<212> TYPE: PRT
<213> ORGANISM: Artificial
<220> FEATURE:
<223> OTHER INFORMATION: Entirely synthetic sequence not obtained from
      any organism
```

```
<220> FEATURE:
<221> NAME/KEY: MISC_FEATURE
<222> LOCATION: (1)..(1)
<223> OTHER INFORMATION: Tetramethylguanyl-arginine
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: c' amidated

<400> SEQUENCE: 33

Xaa Arg Xaa Cys Tyr Xaa Lys Xaa Pro Tyr Arg Xaa Cys Arg
1               5                   10

<210> SEQ ID NO 34
<211> LENGTH: 13
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Tetramethylguanyl-arginine
<220> FEATURE:
<221> NAME/KEY: MISC_FEATURE
<222> LOCATION: (2)..(2)
<223> OTHER INFORMATION: 3-((2-naphthyl) alanine
<220> FEATURE:
<221> NAME/KEY: MISC_FEATURE
<222> LOCATION: (5)..(5)
<223> OTHER INFORMATION: citrulline
<220> FEATURE:
<221> NAME/KEY: MISC_FEATURE
<222> LOCATION: (7)..(7)
<223> OTHER INFORMATION: D-glutamic acid
<220> FEATURE:
<221> NAME/KEY: MISC_FEATURE
<222> LOCATION: (11)..(11)
<223> OTHER INFORMATION: citrulline
<220> FEATURE:
<221> NAME/KEY: MISC_FEATURE
<222> LOCATION: (13)..(13)
<223> OTHER INFORMATION: c' amidated

<400> SEQUENCE: 34

Xaa Xaa Cys Tyr Xaa Lys Xaa Pro Tyr Arg Xaa Cys Arg
1               5                   10

<210> SEQ ID NO 35
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
```

```
-continued

<223> OTHER INFORMATION: 4-fluorobenzoyl-arginine
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: amidated

<400> SEQUENCE: 35

Xaa Arg Xaa Cys Tyr Xaa Lys Xaa Pro Tyr Arg Xaa Cys Arg
1               5                   10

<210> SEQ ID NO 36
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: 2-fluorobenzoyl-arginine
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: c' amidated

<400> SEQUENCE: 36

Xaa Arg Xaa Cys Tyr Xaa Lys Xaa Pro Tyr Arg Xaa Cys Arg
1               5                   10

<210> SEQ ID NO 37
<211> LENGTH: 13
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: 5-aminopentanoyl-arginine
<220> FEATURE:
<221> NAME/KEY: MISC_FEATURE
```

```
<222> LOCATION: (2)..(2)
<223> OTHER INFORMATION: 3-((2-naphthyl) alanine
<220> FEATURE:
<221> NAME/KEY: MISC_FEATURE
<222> LOCATION: (5)..(5)
<223> OTHER INFORMATION: citrulline
<220> FEATURE:
<221> NAME/KEY: MISC_FEATURE
<222> LOCATION: (7)..(7)
<223> OTHER INFORMATION: D-glutamic acid
<220> FEATURE:
<221> NAME/KEY: MISC_FEATURE
<222> LOCATION: (11)..(11)
<223> OTHER INFORMATION: citrulline
<220> FEATURE:
<221> NAME/KEY: MISC_FEATURE
<222> LOCATION: (13)..(13)
<223> OTHER INFORMATION: c' amidated

<400> SEQUENCE: 37

Xaa Xaa Cys Tyr Xaa Lys Xaa Pro Tyr Arg Xaa Cys Arg
1               5                   10

<210> SEQ ID NO 38
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: 2-desamino-arginyl
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: c' amidated

<400> SEQUENCE: 38

Xaa Arg Xaa Cys Tyr Xaa Lys Xaa Pro Tyr Arg Xaa Cys Arg
1               5                   10

<210> SEQ ID NO 39
<211> LENGTH: 13
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Guanyl-arginine
<220> FEATURE:
<221> NAME/KEY: MISC_FEATURE
<222> LOCATION: (2)..(2)
<223> OTHER INFORMATION: 3-((2-naphthyl) alanine
<220> FEATURE:
```

```
<221> NAME/KEY: MISC_FEATURE
<222> LOCATION: (5)..(5)
<223> OTHER INFORMATION: citrulline
<220> FEATURE:
<221> NAME/KEY: MISC_FEATURE
<222> LOCATION: (7)..(7)
<223> OTHER INFORMATION: D-glutamic acid
<220> FEATURE:
<221> NAME/KEY: MISC_FEATURE
<222> LOCATION: (11)..(11)
<223> OTHER INFORMATION: citrulline
<220> FEATURE:
<221> NAME/KEY: MISC_FEATURE
<222> LOCATION: (13)..(13)
<223> OTHER INFORMATION: c' amidated

<400> SEQUENCE: 39

Xaa Xaa Cys Tyr Xaa Lys Xaa Pro Tyr Arg Xaa Cys Arg
1               5                   10

<210> SEQ ID NO 40
<211> LENGTH: 13
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Succinyl-arginine
<220> FEATURE:
<221> NAME/KEY: MISC_FEATURE
<222> LOCATION: (2)..(2)
<223> OTHER INFORMATION: 3-((2-naphthyl) alanine
<220> FEATURE:
<221> NAME/KEY: MISC_FEATURE
<222> LOCATION: (5)..(5)
<223> OTHER INFORMATION: citrulline
<220> FEATURE:
<221> NAME/KEY: MISC_FEATURE
<222> LOCATION: (7)..(7)
<223> OTHER INFORMATION: D-glutamic acid
<220> FEATURE:
<221> NAME/KEY: MISC_FEATURE
<222> LOCATION: (11)..(11)
<223> OTHER INFORMATION: citrulline
<220> FEATURE:
<221> NAME/KEY: MISC_FEATURE
<222> LOCATION: (13)..(13)
<223> OTHER INFORMATION: c' amidated

<400> SEQUENCE: 40

Xaa Xaa Cys Tyr Xaa Lys Xaa Pro Tyr Arg Xaa Cys Arg
1               5                   10

<210> SEQ ID NO 41
<211> LENGTH: 13
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Glutaryl-arginine
<220> FEATURE:
<221> NAME/KEY: MISC_FEATURE
<222> LOCATION: (2)..(2)
<223> OTHER INFORMATION: 3-((2-naphthyl) alanine
<220> FEATURE:
<221> NAME/KEY: MISC_FEATURE
<222> LOCATION: (5)..(5)
<223> OTHER INFORMATION: citrulline
```

-continued

```
<220> FEATURE:
<221> NAME/KEY: MISC_FEATURE
<222> LOCATION: (7)..(7)
<223> OTHER INFORMATION: D-glutamic acid
<220> FEATURE:
<221> NAME/KEY: MISC_FEATURE
<222> LOCATION: (11)..(11)
<223> OTHER INFORMATION: citrulline
<220> FEATURE:
<221> NAME/KEY: MISC_FEATURE
<222> LOCATION: (13)..(13)
<223> OTHER INFORMATION: c' amidated

<400> SEQUENCE: 41

Xaa Xaa Cys Tyr Xaa Lys Xaa Pro Tyr Arg Xaa Cys Arg
1               5                   10

<210> SEQ ID NO 42
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: desaminoTMG-APA (formula IV in the
      specification)
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: c' amidated

<400> SEQUENCE: 42

Xaa Arg Xaa Cys Tyr Xaa Lys Xaa Pro Tyr Arg Xaa Cys Arg
1               5                   10

<210> SEQ ID NO 43
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: R-CH2 - formula (V) in the specification
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
```

```
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: c' amidated

<400> SEQUENCE: 43

Xaa Arg Xaa Cys Tyr Xaa Lys Xaa Pro Tyr Arg Xaa Cys Arg
1               5                   10

<210> SEQ ID NO 44
<211> LENGTH: 13
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (2)..(2)
<223> OTHER INFORMATION: 3-((2-naphthyl) alanine
<220> FEATURE:
<221> NAME/KEY: MISC_FEATURE
<222> LOCATION: (5)..(5)
<223> OTHER INFORMATION: citrulline
<220> FEATURE:
<221> NAME/KEY: MISC_FEATURE
<222> LOCATION: (7)..(7)
<223> OTHER INFORMATION: D-glutamic acid
<220> FEATURE:
<221> NAME/KEY: MISC_FEATURE
<222> LOCATION: (11)..(11)
<223> OTHER INFORMATION: citrulline
<220> FEATURE:
<221> NAME/KEY: MISC_FEATURE
<222> LOCATION: (13)..(13)
<223> OTHER INFORMATION: c' amidated

<400> SEQUENCE: 44

Arg Xaa Cys Tyr Xaa Lys Xaa Pro Tyr Arg Xaa Cys Arg
1               5                   10

<210> SEQ ID NO 45
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: tetramethylguanyl-arginine
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-citrulline
<220> FEATURE:
<221> NAME/KEY: MISC_FEATURE
<222> LOCATION: (12)..(12)
<223> OTHER INFORMATION: citrulline
<220> FEATURE:
```

```
<221> NAME/KEY: MISC_FEATURE
<222> LOCATION: (14)..(14)
<223> OTHER INFORMATION: C' AMIDATED

<400> SEQUENCE: 45

Xaa Arg Xaa Cys Tyr Xaa Lys Xaa Pro Tyr Arg Xaa Cys Arg
1               5                   10

<210> SEQ ID NO 46
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: 6-aminohexanoyl-arginine
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-citrulline
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: C' AMIDATED

<400> SEQUENCE: 46

Xaa Arg Xaa Cys Tyr Xaa Lys Xaa Pro Tyr Arg Xaa Cys Arg
1               5                   10

<210> SEQ ID NO 47
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: 6-aminohexanoyl-arginine
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 47

Xaa Arg Xaa Cys Tyr Arg Lys Xaa Pro Tyr Arg Xaa Cys Arg
1               5                   10

<210> SEQ ID NO 48
```

```
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: C' amidated

<400> SEQUENCE: 48

Arg Arg Xaa Cys Tyr Xaa Arg Xaa Pro Tyr Arg Xaa Cys Arg
1               5                   10

<210> SEQ ID NO 49
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: C' amidated

<400> SEQUENCE: 49

Arg Arg Xaa Cys Tyr Xaa Arg Xaa Pro Tyr Arg Xaa Cys Arg
1               5                   10

<210> SEQ ID NO 50
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
```

```
<221> NAME/KEY: MISC_FEATURE
<222> LOCATION: (1)..(1)
<223> OTHER INFORMATION: N' ACETYLATED
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: C' AMIDATED

<400> SEQUENCE: 50

Arg Arg Xaa Cys Tyr Xaa Lys Xaa Pro Tyr Arg Xaa Cys Arg
1               5                   10

<210> SEQ ID NO 51
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: N' ACETYLATED
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-citrulline
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: C' AMIDATED

<400> SEQUENCE: 51

Arg Arg Xaa Cys Tyr Arg Lys Xaa Pro Tyr Arg Xaa Cys Arg
1               5                   10

<210> SEQ ID NO 52
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: 4-fluorobenzoyl-arginine
<220> FEATURE:
<221> NAME/KEY: MISC_FEATURE
<222> LOCATION: (3)..(3)
<223> OTHER INFORMATION: 3-((2-naphthyl) alanine
```

```
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: C' AMIDATED

<400> SEQUENCE: 52

Xaa Arg Xaa Cys Tyr Xaa Lys Xaa Pro Tyr Arg Xaa Cys Arg
1               5                   10

<210> SEQ ID NO 53
<211> LENGTH: 15
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: 4-fluorobenzoyl-arginine
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (15)..(15)
<223> OTHER INFORMATION: NH-methyl group

<400> SEQUENCE: 53

Xaa Arg Xaa Cys Tyr Xaa Lys Xaa Pro Tyr Arg Xaa Cys Arg Xaa
1               5                   10                  15

<210> SEQ ID NO 54
<211> LENGTH: 15
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: 4-fluorobenzoyl-arginine
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
```

```
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (15)..(15)
<223> OTHER INFORMATION: NH-ethyl group

<400> SEQUENCE: 54

Xaa Arg Xaa Cys Tyr Xaa Lys Xaa Pro Tyr Arg Xaa Cys Arg Xaa
1               5                   10                  15

<210> SEQ ID NO 55
<211> LENGTH: 15
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: 4-fluorobenzoyl-arginine
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (15)..(15)
<223> OTHER INFORMATION: NH-isopropyl

<400> SEQUENCE: 55

Xaa Arg Xaa Cys Tyr Xaa Lys Xaa Pro Tyr Arg Xaa Cys Arg Xaa
1               5                   10                  15

<210> SEQ ID NO 56
<211> LENGTH: 15
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: 4-fluorobenzoyl-arginine
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
```

```
<222> LOCATION: (8)..(8)
<223> OTHER INFORMATION: D-glutamic acid
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (15)..(15)
<223> OTHER INFORMATION: tyramine residue

<400> SEQUENCE: 56

Xaa Arg Xaa Cys Tyr Xaa Lys Xaa Pro Tyr Arg Xaa Cys Arg Xaa
1               5                   10                  15

<210> SEQ ID NO 57
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 57

Ala Arg Xaa Cys Tyr Arg Lys Xaa Pro Tyr Arg Xaa Cys Arg
1               5                   10

<210> SEQ ID NO 58
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 58

Arg Arg Xaa Cys Tyr Ala Lys Xaa Pro Tyr Arg Xaa Cys Arg
1               5                   10

<210> SEQ ID NO 59
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
```

```
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 59

Arg Arg Xaa Cys Tyr Arg Ala Xaa Pro Tyr Arg Xaa Cys Arg
1               5                   10

<210> SEQ ID NO 60
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-alanine
<220> FEATURE:
<221> NAME/KEY: MISC_FEATURE
<222> LOCATION: (12)..(12)
<223> OTHER INFORMATION: citrulline

<400> SEQUENCE: 60

Arg Arg Xaa Cys Tyr Arg Lys Xaa Pro Tyr Arg Xaa Cys Arg
1               5                   10

<210> SEQ ID NO 61
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 61

Arg Arg Xaa Cys Tyr Arg Lys Xaa Ala Tyr Arg Xaa Cys Arg
1               5                   10

<210> SEQ ID NO 62
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
```

```
<220> FEATURE:
<221> NAME/KEY: MISC_FEATURE
<222> LOCATION: (8)..(8)
<223> OTHER INFORMATION: 3-((2-naphthyl) alanine
<220> FEATURE:
<221> NAME/KEY: MISC_FEATURE
<222> LOCATION: (12)..(12)
<223> OTHER INFORMATION: citrulline

<400> SEQUENCE: 62

Arg Arg Xaa Cys Tyr Arg Lys Xaa Pro Ala Arg Xaa Cys Arg
1               5                   10

<210> SEQ ID NO 63
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 63

Arg Arg Xaa Cys Tyr Arg Lys Xaa Pro Tyr Ala Xaa Cys Arg
1               5                   10

<210> SEQ ID NO 64
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: citrulline
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 64

Xaa Arg Xaa Cys Tyr Arg Lys Xaa Pro Tyr Arg Xaa Cys Arg
1               5                   10

<210> SEQ ID NO 65
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
```

-continued

```
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 65

Arg Arg Xaa Cys Tyr Xaa Lys Xaa Pro Tyr Arg Xaa Cys Arg
1               5                   10

<210> SEQ ID NO 66
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: C' AMIDATED

<400> SEQUENCE: 66

Arg Arg Xaa Cys Tyr Xaa Lys Xaa Pro Tyr Arg Xaa Cys Arg
1               5                   10

<210> SEQ ID NO 67
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (7)..(7)
<223> OTHER INFORMATION: citrulline
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline
```

```
<400> SEQUENCE: 67

Arg Arg Xaa Cys Tyr Arg Xaa Xaa Pro Tyr Arg Xaa Cys Arg
1               5                   10

<210> SEQ ID NO 68
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-citrulline
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: C' AMIDATED

<400> SEQUENCE: 68

Arg Arg Xaa Cys Tyr Xaa Lys Xaa Pro Tyr Arg Xaa Cys Arg
1               5                   10

<210> SEQ ID NO 69
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-lysine
<220> FEATURE:
<221> NAME/KEY: MISC_FEATURE
<222> LOCATION: (12)..(12)
<223> OTHER INFORMATION: citrulline

<400> SEQUENCE: 69

Arg Arg Xaa Cys Tyr Arg Lys Xaa Pro Tyr Arg Xaa Cys Arg
1               5                   10

<210> SEQ ID NO 70
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
```

```
<221> NAME/KEY: MISC_FEATURE
<222> LOCATION: (6)..(6)
<223> OTHER INFORMATION: citrulline
<220> FEATURE:
<221> NAME/KEY: MISC_FEATURE
<222> LOCATION: (8)..(8)
<223> OTHER INFORMATION: D-citrulline
<220> FEATURE:
<221> NAME/KEY: MISC_FEATURE
<222> LOCATION: (12)..(12)
<223> OTHER INFORMATION: citrulline

<400> SEQUENCE: 70

Arg Arg Xaa Cys Tyr Xaa Lys Xaa Pro Tyr Arg Xaa Cys Arg
1               5                   10

<210> SEQ ID NO 71
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (3)..(3)
<223> OTHER INFORMATION: 3-((2-naphthyl) alanine
<220> FEATURE:
<221> NAME/KEY: MISC_FEATURE
<222> LOCATION: (8)..(8)
<223> OTHER INFORMATION: D-citrulline
<220> FEATURE:
<221> NAME/KEY: MISC_FEATURE
<222> LOCATION: (12)..(12)
<223> OTHER INFORMATION: citrulline

<400> SEQUENCE: 71

Arg Arg Xaa Cys Tyr Arg Lys Xaa Pro Tyr Arg Xaa Cys Arg
1               5                   10

<210> SEQ ID NO 72
<211> LENGTH: 27
<212> TYPE: DNA
<213> ORGANISM: Artificial
<220> FEATURE:
<223> OTHER INFORMATION: PCR primer

<400> SEQUENCE: 72
agctgttggc tgaaaaggtg gtctatg                                        27

<210> SEQ ID NO 73
<211> LENGTH: 26
<212> TYPE: DNA
<213> ORGANISM: Artificial
<220> FEATURE:
<223> OTHER INFORMATION: PCR primer

<400> SEQUENCE: 73
gcgcttctgg tggcccttgg agtgtg                                         26

<210> SEQ ID NO 74
<211> LENGTH: 22
<212> TYPE: DNA
<213> ORGANISM: Artificial
<220> FEATURE:
<223> OTHER INFORMATION: PCR primer

<400> SEQUENCE: 74
atgaacgcca aggtcgtggt cg                                             22
```

```
<210> SEQ ID NO 75
<211> LENGTH: 19
<212> TYPE: DNA
<213> ORGANISM: Artificial
<220> FEATURE:
<223> OTHER INFORMATION: PCR primer

<400> SEQUENCE: 75
tgttgttgtt cttcagccg                                                19

<210> SEQ ID NO 76
<211> LENGTH: 22
<212> TYPE: DNA
<213> ORGANISM: Artificial
<220> FEATURE:
<223> OTHER INFORMATION: PCR primer

<400> SEQUENCE: 76
atgaacgcca aggtcgtggt cg                                            22

<210> SEQ ID NO 77
<211> LENGTH: 20
<212> TYPE: DNA
<213> ORGANISM: Artificial
<220> FEATURE:
<223> OTHER INFORMATION: PCR primer

<400> SEQUENCE: 77
cgggtcaatg cacacttgtc                                               20

<210> SEQ ID NO 78
<211> LENGTH: 20
<212> TYPE: DNA
<213> ORGANISM: Artificial
<220> FEATURE:
<223> OTHER INFORMATION: PCR primer

<400> SEQUENCE: 78
ccctggactt cgagcaagag                                               20

<210> SEQ ID NO 79
<211> LENGTH: 20
<212> TYPE: DNA
<213> ORGANISM: Artificial
<220> FEATURE:
<223> OTHER INFORMATION: PCR primer

<400> SEQUENCE: 79
tctccttctg catcctgtcg                                               20

<210> SEQ ID NO 80
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derivatized at the N-terminal, or is a hydrogen
      atom
<220> FEATURE:
<221> NAME/KEY: MISC_FEATURE
<222> LOCATION: (1)..(14)
<223> OTHER INFORMATION: L-amino acid or D-amino acid
<220> FEATURE:
```

```
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derivatized at the N-terminal,
      Xaa is Arg or Glu, and when Xaa of (1) is a hydrogen atom, Xaa is
      Arg or Glu which may be derivatized at the N-terminal
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is Arg, Lys, citrulline or Glu.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derivatized at the C-terminal.

<400> SEQUENCE: 80

Xaa Xaa Xaa Cys Tyr Xaa Xaa Xaa Xaa Xaa Xaa Xaa Cys Xaa
1               5                   10

<210> SEQ ID NO 81
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Xaa is an arginine, citrulline, alanine or
      glutamic acid residue which may be derivatized at N-terminal, or
      Xaa is deleted
<220> FEATURE:
<221> NAME/KEY: MISC_FEATURE
<222> LOCATION: (1)..(14)
<223> OTHER INFORMATION: L-amino acid or D-amino acid
<220> FEATURE:
```

```
<221> NAME/KEY: MISC_FEATURE
<222> LOCATION: (2)..(2)
<223> OTHER INFORMATION: When Xaa of (1) is Arg, citrulline, Ala or Glu
      which may be derived at the N-terminal, Xaa is Arg or Glu, and
      when Xaa of (1) is deleted, Xaa is Arg or Glu which may be derived
      at the N-terminal
<220> FEATURE:
<221> NAME/KEY: MISC_FEATURE
<222> LOCATION: (3)..(3)
<223> OTHER INFORMATION: Xaa is an aromatic amino acid residue.
<220> FEATURE:
<221> NAME/KEY: DISULFID
<222> LOCATION: (4)..(13)
<223> OTHER INFORMATION: Cys at 4-position and Cys at 13-position may be
      linked by a disulfid bond.
<220> FEATURE:
<221> NAME/KEY: MISC_FEATURE
<222> LOCATION: (6)..(6)
<223> OTHER INFORMATION: Xaa is an arginine, citrulline, alanine or
      glutamic acid residue
<220> FEATURE:
<221> NAME/KEY: MISC_FEATURE
<222> LOCATION: (7)..(7)
<223> OTHER INFORMATION: Xaa is an arginine, citrulline, alanine, lysine
      or glutamic acid residue
<220> FEATURE:
<221> NAME/KEY: MISC_FEATURE
<222> LOCATION: (8)..(8)
<223> OTHER INFORMATION: Xaa is a lysine, alanine, citrulline or
      glutamic acid residue
<220> FEATURE:
<221> NAME/KEY: MISC_FEATURE
<222> LOCATION: (9)..(9)
<223> OTHER INFORMATION: Xaa is a proline or alanine residue
<220> FEATURE:
<221> NAME/KEY: MISC_FEATURE
<222> LOCATION: (10)..(10)
<223> OTHER INFORMATION: Xaa is a tyrosine, alanine or glutamic acid
      residue
<220> FEATURE:
<221> NAME/KEY: MISC_FEATURE
<222> LOCATION: (11)..(11)
<223> OTHER INFORMATION: Xaa is an arginine, citrulline or glutamic acid
      residue
<220> FEATURE:
<221> NAME/KEY: MISC_FEATURE
<222> LOCATION: (12)..(12)
<223> OTHER INFORMATION: Xaa is a citrulline or glutamic acid residue
<220> FEATURE:
<221> NAME/KEY: MISC_FEATURE
<222> LOCATION: (14)..(14)
<223> OTHER INFORMATION: Xaa is an arginine or glutamic acid residue
      which may be derivatized at C-terminal

<400> SEQUENCE: 81

Xaa Xaa Xaa Cys Tyr Xaa Xaa Xaa Xaa Xaa Xaa Xaa Cys Xaa
1               5                   10

<210> SEQ ID NO 82
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Xaa is Glu which may be derivatized at the
      N-terminal, or is a hydrogen atom
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
```

```
<223> OTHER INFORMATION: When Xaa of (1) is Glu which may be derivatized
      at the N-terminal, Xaa is Arg or Glu, and when Xaa of (1) is a
      hydrogen atom, Xaa is Arg or Glu which may be derivatized at the
      N-terminal.
<220> FEATURE:
<221> NAME/KEY: MISC_FEATURE
<222> LOCATION: (3)..(3)
<223> OTHER INFORMATION: Xaa is an aromatic amino acid residue.
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg.
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is citrulline, Glu, Arg or Lys.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derivatized at the C-terminal.

<400> SEQUENCE: 82

Xaa Xaa Xaa Cys Tyr Xaa Xaa Xaa Xaa Xaa Xaa Xaa Cys Xaa
1               5                   10

<210> SEQ ID NO 83
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derivatized at the N-terminal, or is a hydrogen
      atom
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (3)..(3)
```

```
<223> OTHER INFORMATION: Xaa is an aromatic amino acid residue.
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is Arg, Lys, citrulline or Glu.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derived at the C-terminal.

<400> SEQUENCE: 83

Xaa Glu Xaa Cys Tyr Xaa Xaa Xaa Xaa Xaa Xaa Xaa Cys Xaa
1               5                   10

<210> SEQ ID NO 84
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derivatized at the N-terminal, or is a hydrogen
      atom
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derivatized at the N-terminal,
      Xaa is Arg or Glu, and when Xaa of (1) is a hydrogen atom, Xaa is
      Arg or Glu which may be derivatized at the N-terminal
<220> FEATURE:
<221> NAME/KEY: MISC_FEATURE
<222> LOCATION: (3)..(3)
```

```
<223> OTHER INFORMATION: Xaa is an aromatic amino acid residue
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is Arg, Lys, citrulline or Glu.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derivatized at the C-terminal.

<400> SEQUENCE: 84

Xaa Xaa Xaa Cys Tyr Glu Xaa Xaa Xaa Xaa Xaa Xaa Cys Xaa
1               5                   10

<210> SEQ ID NO 85
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derivatized at the N-terminal, or is a hydrogen
      atom
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derivatized at the N-terminal,
      Xaa is Arg or Glu, and when Xaa of (1) is a hydrogen atom, Xaa is
      Arg or Glu which may be derivatized at the N-terminal
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: DISULFID
<222> LOCATION: (4)..(13)
<223> OTHER INFORMATION: Cys at 4-position and Cys at 13-position may
```

-continued

```
      form a disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is Arg, Lys, citrulline or Glu.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derivatized at the C-terminal.

<400> SEQUENCE: 85

Xaa Xaa Xaa Cys Tyr Xaa Xaa Glu Xaa Xaa Xaa Xaa Cys Xaa
1               5                   10

<210> SEQ ID NO 86
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derivatized at the N-terminal, or is a hydrogen
      atom
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derivatized at the N-terminal,
      Xaa is Arg or Glu, and when Xaa of (1) is a hydrogen atom, Xaa is
      Arg or Glu which may be derivatized at the N-terminal
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
```

```
                                    Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is Arg, Lys, citrulline or Glu.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derivatized at the C-terminal.

<400> SEQUENCE: 86

Xaa Xaa Xaa Cys Tyr Xaa Xaa Xaa Xaa Glu Xaa Xaa Cys Xaa
1               5                   10

<210> SEQ ID NO 87
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derivatized at the N-terminal, or is a hydrogen
      atom
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derivatized at the N-terminal,
      Xaa is Arg or Glu, and when Xaa of (1) is a hydrogen atom, Xaa is
      Arg or Glu which may be derivatized at the N-terminal
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
```

```
                                Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (12)..(12)
<223> OTHER INFORMATION: Xaa is Arg, Lys, citrulline or Glu.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derivatized at the C-terminal.

<400> SEQUENCE: 87

Xaa Xaa Xaa Cys Tyr Xaa Xaa Xaa Xaa Xaa Glu Xaa Cys Xaa
1               5                   10

<210> SEQ ID NO 88
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derivatized at the N-terminal, or is a hydrogen
      atom
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derivatized at the N-terminal,
      Xaa is Arg or Glu, and when Xaa of (1) is a hydrogen atom, Xaa is
      Arg or Glu which may be derivatized at the N-terminal
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg or Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
```

```
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is Arg, Lys, citrulline or Glu.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derivatized at the C-terminal.

<400> SEQUENCE: 88

Xaa Xaa Xaa Cys Tyr Xaa Xaa Xaa Xaa Xaa Xaa Xaa Cys Xaa
1               5                   10

<210> SEQ ID NO 89
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derivatized at the N-terminal, or is a hydrogen
      atom
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derivatized at the N-terminal,
      Xaa is Arg or Glu, and when Xaa of (1) is a hydrogen atom, Xaa is
      Arg or Glu which may be derivatized at the N-terminal
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
```

```
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is Arg, Lys or Glu.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derivatized at the C-terminal.

<400> SEQUENCE: 89

Xaa Xaa Xaa Cys Tyr Xaa Xaa Xaa Xaa Xaa Xaa Xaa Cys Xaa
1               5                   10

<210> SEQ ID NO 90
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
      Glu which may be derivatized at the N-terminal, or is a hydrogen
      atom
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
      citrulline, Ala or Glu which may be derivatized at the N-terminal,
      Xaa is Arg or Glu, and when Xaa of (1) is a hydrogen atom, Xaa is
      Arg or Glu which may be derivatized at the N-terminal
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
```

-continued

```
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is Arg, Lys, citrulline or Glu.
<220> FEATURE:
<221> NAME/KEY: MISC_FEATURE
<222> LOCATION: (14)..(14)
<223> OTHER INFORMATION: Xaa is Glu, Lys or citrulline which may be
      derivatized at the C-terminal.

<400> SEQUENCE: 90

Xaa Xaa Xaa Cys Tyr Xaa Xaa Xaa Xaa Xaa Xaa Xaa Cys Xaa
1               5                   10

<210> SEQ ID NO 91
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Xaa is Arg, Ala or Citrulline
<220> FEATURE:
<221> NAME/KEY: MISC_FEATURE
<222> LOCATION: (3)..(3)
<223> OTHER INFORMATION: Xaa is Trp or naphtylalanine
<220> FEATURE:
<221> NAME/KEY: MISC_FEATURE
<222> LOCATION: (6)..(6)
<223> OTHER INFORMATION: Xaa is Arg, Ala or Citrulline
<220> FEATURE:
<221> NAME/KEY: MISC_FEATURE
<222> LOCATION: (7)..(7)
<223> OTHER INFORMATION: Xaa is Lys, Ala or Citrulline
<220> FEATURE:
<221> NAME/KEY: MISC_FEATURE
<222> LOCATION: (8)..(9)
<223> OTHER INFORMATION: These positions represent a dipeptide selected
      from: D-lysyl-proline, D-alanyl-proline, D-lysyl-alanine and
      D-citrullyl-proline
<220> FEATURE:
<221> NAME/KEY: MISC_FEATURE
<222> LOCATION: (10)..(10)
<223> OTHER INFORMATION: Xaa is Tyr or Ala
<220> FEATURE:
<221> NAME/KEY: MISC_FEATURE
<222> LOCATION: (11)..(11)
<223> OTHER INFORMATION: Xaa is Arg, Ala or Citrulline
<220> FEATURE:
<221> NAME/KEY: MISC_FEATURE
<222> LOCATION: (12)..(12)
<223> OTHER INFORMATION: Xaa is Citrulline

<400> SEQUENCE: 91

Xaa Arg Xaa Cys Tyr Xaa Xaa Xaa Xaa Xaa Xaa Xaa Cys Arg
1               5                   10
```

```
<210> SEQ ID NO 92
<211> LENGTH: 13
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Arg, Lys, Ala, ornithine, citrulline, any
      N-alpha-substituted derivative of these amino acids, or not
      present
<220> FEATURE:
<221> NAME/KEY: MISC_FEATURE
<222> LOCATION: (3)..(3)
<223> OTHER INFORMATION: Any aromatic amino acid
<220> FEATURE:
<221> NAME/KEY: MISC_FEATURE
<222> LOCATION: (6)..(7)
<223> OTHER INFORMATION: Each position independently represents Arg,
      Lys, Ala, ornithine or citrulline
<220> FEATURE:
<221> NAME/KEY: MISC_FEATURE
<222> LOCATION: (8)..(8)
<223> OTHER INFORMATION: D-citrulline, D-alanine, citrulline or alanine
<220> FEATURE:
<221> NAME/KEY: MISC_FEATURE
<222> LOCATION: (9)..(9)
<223> OTHER INFORMATION: Tyr, Phe, Ala, naphthylalanine or citrulline
<220> FEATURE:
<221> NAME/KEY: MISC_FEATURE
<222> LOCATION: (10)..(10)
<223> OTHER INFORMATION: Arg, Lys, Ala, ornithine or citrulline
<220> FEATURE:
<221> NAME/KEY: MISC_FEATURE
<222> LOCATION: (11)..(11)
<223> OTHER INFORMATION: citrulline
<220> FEATURE:
<221> NAME/KEY: MISC_FEATURE
<222> LOCATION: (13)..(13)
<223> OTHER INFORMATION: Lys or Arg; a carboxyl group may be amidated

<400> SEQUENCE: 92

Xaa Arg Xaa Cys Tyr Xaa Xaa Xaa Xaa Xaa Xaa Cys Xaa
1               5                   10

<210> SEQ ID NO 93
<211> LENGTH: 14
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Arg, Lys, Ala, ornithine, citrulline, any
      N-alpha-substituted derivative of these amino acids, or not
      present
<220> FEATURE:
<221> NAME/KEY: MISC_FEATURE
<222> LOCATION: (1)..(14)
<223> OTHER INFORMATION: this sequence is structured with the proviso
      that either of the amino acid residues at positions 1, 6, 7, 10,
      11 and 14 is Ala or citrulline
<220> FEATURE:
<221> NAME/KEY: MISC_FEATURE
<222> LOCATION: (3)..(3)
<223> OTHER INFORMATION: Any aromatic amino acid
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
```

```
<222> LOCATION: (6)..(7)
<223> OTHER INFORMATION: Each position independently represents Arg,
      Lys, Ala, ornithine or citrulline
<220> FEATURE:
<221> NAME/KEY: MISC_FEATURE
<222> LOCATION: (8)..(9)
<223> OTHER INFORMATION: D-orn-pro, pro-D-orn, D-lys-pro, pro-D-lys,
      D-arg-pro, pro-D-arg, D-cit-pro, D-cit-ala, D-ala-cit, pro-D-cit,
      gly-orn, orn-gly, gly-lys, lys-gly, gly-arg, arg-gly, gly-cit,
      cit-gly, D-ala-pro or D-lys-ala
<220> FEATURE:
<221> NAME/KEY: MISC_FEATURE
<222> LOCATION: (10)..(10)
<223> OTHER INFORMATION: Tyr, Phe, Ala, naphthylalanine or citrulline
<220> FEATURE:
<221> NAME/KEY: MISC_FEATURE
<222> LOCATION: (11)..(11)
<223> OTHER INFORMATION: Arg, Lys, Ala, ornithine or citrulline
<220> FEATURE:
<221> NAME/KEY: MISC_FEATURE
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: Lys or Arg; a carboxyl group may be amidated

<400> SEQUENCE: 93

Xaa Arg Xaa Cys Tyr Xaa Xaa Xaa Xaa Xaa Xaa Xaa Cys Xaa
1               5                   10

<210> SEQ ID NO 94
<211> LENGTH: 18
<212> TYPE: PRT
<213> ORGANISM: Artificial
<220> FEATURE:
<223> OTHER INFORMATION: Entirely synthetic sequence not obtained from
      any organism
<220> FEATURE:
<221> NAME/KEY: MISC_FEATURE
<222> LOCATION: (1)..(1)
<223> OTHER INFORMATION: Arg, Lys, Ala, ornithine, citrulline, any
      N-alpha-substituted derivative of these amino acids, or not
      present
<220> FEATURE:
<221> NAME/KEY: MISC_FEATURE
<222> LOCATION: (1)..(18)
<223> OTHER INFORMATION: this sequence is structured with the proviso
      that either of the amino acid residues at positions 1, 6, 7, 14,
      15 and 18 is Ala or citrulline
<220> FEATURE:
<221> NAME/KEY: MISC_FEATURE
<222> LOCATION: (3)..(3)
<223> OTHER INFORMATION: Any aromatic amino acid
<220> FEATURE:
<221> NAME/KEY: DISULFID
<222> LOCATION: (4)..(17)
<223> OTHER INFORMATION: Cys at 4-position and Cys at 17-position may
      form a disulfid bond.
<220> FEATURE:
<221> NAME/KEY: MISC_FEATURE
<222> LOCATION: (6)..(7)
<223> OTHER INFORMATION: Each position independently represents Arg,
      Lys, Ala, ornithine or citrulline
<220> FEATURE:
<221> NAME/KEY: MISC_FEATURE
<222> LOCATION: (8)..(8)
<223> OTHER INFORMATION: Ala, Val, Leu, Ile, Ser, Cys or Met
<220> FEATURE:
<221> NAME/KEY: DISULFID
<222> LOCATION: (8)..(13)
<223> OTHER INFORMATION: when positions 8 and 13 are Cys, they may form
      a disulfide bond
<220> FEATURE:
<221> NAME/KEY: MISC_FEATURE
<222> LOCATION: (9)..(9)
<223> OTHER INFORMATION: Any aromatic amino acid
```

```
<220> FEATURE:
<221> NAME/KEY: MISC_FEATURE
<222> LOCATION: (10)..(10)
<223> OTHER INFORMATION: Arg, Lys, Ala, ornithine or citrulline
<220> FEATURE:
<221> NAME/KEY: MISC_FEATURE
<222> LOCATION: (12)..(12)
<223> OTHER INFORMATION: Tyr, Phe, Trp, Ala, Val, Leu, Ile, Ser, Cys or
      Met
<220> FEATURE:
<221> NAME/KEY: MISC_FEATURE
<222> LOCATION: (13)..(13)
<223> OTHER INFORMATION: Ala, Val, Leu, Ile, Ser, Cys or Met
<220> FEATURE:
<221> NAME/KEY: MISC_FEATURE
<222> LOCATION: (16)..(16)
<223> OTHER INFORMATION: citrulline

<400> SEQUENCE: 94

Xaa Arg Xaa Cys Tyr Xaa Xaa Xaa Xaa Xaa Gly Xaa Xaa Xaa Xaa Xaa
1               5                   10                  15

Cys Xaa
```

The invention claimed is:

1. A method of promoting wound healing in a subject in need thereof, comprising administering to the subject a pharmaceutical composition comprising as an active ingredient a therapeutically effective amount of a CXCR4 inhibitor wherein said CXCR4 inhibitor is a peptide having the amino acid sequence set forth in any one of SEQ ID NOS: 1-68 and 70-71, wherein the wound is a partial thickness dermal wound.

2. The method of claim 1, wherein the peptide is selected from the group consisting of SEQ ID NOS: 1-3, 9, 45, 46, 50-56, 65, 66, 68, 70 and 71.

3. The method of claim 1, wherein the peptide is selected from the group consisting of SEQ ID NOS: 3, 9, 45, 46, 68 and 70.

4. The method of claim 1, wherein the peptide is selected from the group consisting of SEQ ID NOS: 1, 50, 52, 65 and 66.

5. The method of claim 1, wherein the peptide is selected from the group consisting of SEQ ID NOS: 53-56.

6. The method of claim 1, wherein the peptide is SEQ ID NO:65.

7. The method of claim 1, wherein the peptide is SEQ ID NO: 52.

8. The method of claim 1, wherein the wound is a dermal burn.

9. The method of claim 1 for the reduction of scarring in said subject.

10. The method of claim 1, wherein said subject is in need of improved epithelialization.

11. The method of claim 1, wherein said subject is need of inhibited fibrosis.

12. The method of claim 1 wherein the pharmaceutical composition is administered to said subject in a manner selected from the group consisting of: topically, intralesionally, transdermally, subcutaneously, intravenously, intrarectally and orally.

13. The method of claim 1, wherein the composition is a topical pharmaceutical composition.

14. The method of claim 1, wherein the composition consists essentially of said CXCR4 inhibitor.

15. The method of claim 13, wherein the composition consists essentially of said CXCR4 inhibitor.

16. A method of treating wounds in a subject in need thereof, comprising administering to the subject a pharmaceutical composition comprising as an active ingredient a therapeutically effective amount of a CXCR4 inhibitor, wherein said CXCR4 inhibitor is a peptide having the amino acid sequence set forth in any one of SEQ ID NOS: 1-68 and 70-71, and wherein the wounds are selected from the group consisting of burn wounds, pressure sores, venous stasis ulcers and diabetic ulcers.

17. The method of claim 10 wherein said subject is in need of improved epithelialization and inhibited fibrosis.

18. The method of claim 10 wherein said subject is in need of reduced scarring.

* * * * *